(12) United States Patent
Hirsh

(10) Patent No.: US 7,657,306 B2
(45) Date of Patent: Feb. 2, 2010

(54) NON-INVASIVE METHOD AND DEVICE TO MONITOR CARDIAC PARAMETERS

(76) Inventor: Robert Hirsh, 208 Sycamore St., Merion, PA (US) 19066

( * ) Notice: Subject to any disclaimer, the term of this patent is extended or adjusted under 35 U.S.C. 154(b) by 387 days.

(21) Appl. No.: 11/266,122

(22) Filed: Nov. 3, 2005

(65) Prior Publication Data

US 2006/0064026 A1    Mar. 23, 2006

Related U.S. Application Data

(62) Division of application No. 09/999,125, filed on Oct. 31, 2001, now Pat. No. 7,054,679.

(51) Int. Cl.
*A61B 5/0428* (2006.01)

(52) U.S. Cl. .................. 600/513; 600/526

(58) Field of Classification Search ............ 600/513
See application file for complete search history.

(56) References Cited

U.S. PATENT DOCUMENTS

| | | | |
|---|---|---|---|
| 4,203,451 A | 5/1980 | Panico | 128/672 |
| 4,677,984 A | 7/1987 | Sramek | |
| 4,960,128 A * | 10/1990 | Gordon et al. | 600/490 |
| 5,103,828 A | 4/1992 | Sramek | |
| 5,181,517 A | 1/1993 | Hickey | |
| 5,211,177 A | 5/1993 | Chesney et al. | |
| 5,309,917 A | 5/1994 | Wang et al. | |
| 5,368,040 A | 11/1994 | Carney | |
| 5,497,778 A | 3/1996 | Hon | |
| 6,090,047 A * | 7/2000 | Kass et al. | 600/485 |
| 6,440,078 B1 | 8/2002 | Curiel et al. | |
| 6,471,646 B1 * | 10/2002 | Thede | 600/301 |
| 6,939,303 B2 | 9/2005 | Curiel | |
| 6,994,675 B2 | 2/2006 | Sharrock | |
| 7,054,679 B2 | 5/2006 | Hirsh | |
| 2006/0167363 A1 | 7/2006 | Osypka et al. | |

FOREIGN PATENT DOCUMENTS

WO    WO 92 06633    4/1992

(Continued)

OTHER PUBLICATIONS

Nakagaware et al., "A portable instrument for non-invasive monitoring of beat-by-beat cardiovascular haemodynamic parameters based on the volume-compensation and electrical-admittance method" *Medical and Biological Engineering and Computing*, vol. 38, No. 1, Jan. 2000.

(Continued)

*Primary Examiner*—Kennedy J Schaetzle
(74) *Attorney, Agent, or Firm*—Knoble Yoshida & Dunleavy, LLC

(57) ABSTRACT

A method of and a device for non-invasively measuring the hemodynamic state of a subject or a human patient involve steps and units of non-invasively measuring cardiac cycle period, electrical-mechanical interval, mean arterial pressure, and ejection interval and converting the measured electrical-mechanical interval, mean arterial pressure and ejection interval into the cardiac parameters such as Preload, Afterload and Contractility, which are the common cardiac parameters used by an anesthesiologist. The converted hemodynamic state of a patient is displayed on a screen as a three-dimensional vector with each of its three coordinates respectively representing Preload, Afterload and Contractility. Therefore, a medical practitioner looks at the screen and quickly obtains the important and necessary information.

25 Claims, 37 Drawing Sheets

FOREIGN PATENT DOCUMENTS

WO    WO 92/11805    7/1992

OTHER PUBLICATIONS

Sramek, B.B., "Physiologic Chart for Rapid Identification of Causes of Abnormal Haemodynamics", *Annals of the Academy of Medicine*, vol. 23, No. 6, Nov. 1, 1994 pp. 26-32.

Huemer, et al., "Influence of positive end-expiratory pressure on right and left ventricular performance assessed by Doppler two-dimensional echocardiography", *Chest*, vol. 106, No. 1, Jul. 1004, pp. 67-73.

Harada et al., "Principle of a noninvasive method of measuring maximum pressure change with respect to time of the left ventricle theory and experiments", *Heart and Vessels*, vol. 3, No. 1, 1987, pp. 25-32.

Campbell et al., "A comparison of cardiac rate-pressure product and pressure-rate quotient with Holter monitoring in patients with hypertension and cardiovascular disease: a follow-up report" *Oral Surgery, Oral Medicine, Oral Pathology, Oral Radiology and Endodontics*, vol. 84, No. 2, Aug. 1997, pp. 125-128.

Minerva Anestesiologiica, Italy, Jun. 1990, vol. 56, No. 6, pp. 199-205.

Adler et al., "Time to dp/dt/sub/max reflects both inotropic and chronotropic properties of cardiac contraction: a conscious dog study" *Physiological Measurement*, Nov. 1996, vol. 17, No. 4, pp. 2878-295.

Welham et al., The first derivative of the transthoracic electrical impedance as as index of changes in myocardial contractility in the intact anaesthetized dog *Intensive Care Medicine*, vol. 4, No. 1, Jan. 1978, p. 44.

Klein, G., M.D.; Emmerich, M., M.D.; Clinical Evaluation of Non-invasive Monitoring Aortic Blood Flow, (ABF) by a Transesophageal Echo-Doppler-Device; Anesthesiology 1998; V89 No. 3A: A953.

Wallace, A.W., M.D., PhD, et al.; Endothracheal Cardiac output Monitor; Anesthesiology 2000;V92; pp. 178-189.

Braunwald, E. M.D., ed.; Heart Disease, A Textbook of Cardiovascular Medicine; Fourth Edition; Philadelphia, W.B. Saunders Company; 1992; p. 420.

Braunwald, E. M.D., ed.; Heart Disease, A Textbook of Cardiovascular Medicine; Fourth Edition; Philadelphia, W.B. Saunders Company; 1992; p. 431.

Connors, A.F. Jr., M.D.,et al.; The Effectiveness of Right Heart Catherization in the Initial Care of the Critically Ill Patients; J. Amer. Med. Assn., 1996; 276:889-897.

Dalen, J.E. Bone R.C.: Is It Time to Pull the Pulmonary Catheter? J. Amer. Med. Assn., 1996; 276:916-8.

European Patent Office Extended Search Report dated Jun. 20, 2008 for related EP Application No. 08100922.7.

Christine Berton and Bernard Cholley: "Equipment review: New techniques for cardiac output measurement oesophageal Doppler, Fick principle using carbon dioxide, and pulse contour analysis", Critical Care, Biomed Central Ltd., London, GB, vol. 6., No. 3, Apr. 25, 2002, pp. 216-221.

Hett D. A. et al., "Non-invasive cardiac output monitoring", Current Anesthesia and Critical Care, Churchill Livingstone, London, GB, vol. 14, No. 4, Aug. 1, 2003, pp. 187-191.

English Translation of JP Office Action dated Dec. 12, 2008 for related JP Application No. 2003-539529.

Yoshizawa et al., "A Noninvasive Estimation Tool for Cardiac Function (Emax PVA)", Anthology of papers regarding Bionics and Physiology Symposium, Japan, Oct. 13, 2000, 15th, pp. 189-192.

* cited by examiner

NON-INVASIVE METHOD AND DEVICE TO MONITOR CARDIAC PARAMETERS

This is a divisional of prior application Ser. No. 09/999,125 filed on Oct. 31, 2001, now U.S. Pat. No. 7,054,679 under 37 CFR 1.53(b)

BACKGROUND OF THE INVENTION

1. Field of the Invention

The present invention relates to a non-invasive method and device to monitor cardiac parameters.

2. Description of the Prior Art

At the present time anesthetics, (drugs which induce loss of sensation) are often used for surgical operations. A general anesthetic generally causes a progressive depression of the central nervous system and induces the patient to lose consciousness. In contrast, a local anesthetic affects sensation at the region where it is applied.

Generally, prior to the operation, the patient is anesthetized by a specialized medical practitioner ("anesthesiologist") who administers one or more volatile liquids or gases such as nitrous oxide, halothane, isoflurane, sevoflurane, desflurane, and etc. Alternatively, non-volatile sedative-hypnotic drugs such as pentothal, propofol, and etomidate may are administered by injection or intravenous infusion. Opioid analgesics like morphine, fentanyl, or sufenanil may likewise be administered by injection or infusion, to relieve pain by raising the pain sensation threshold.

Some of the objectives of a correctly administered general anesthetic are as follows: Firstly, the patient should be sufficiently anesthetized so that his/her movements are blocked. If the patient's movements are not sufficiently blocked, the patient may begin to "twitch" (involuntary muscle reflexes) during the operation, which may move or disturb the operating field that is an area being operated. Such blockage of movement occurs with a paralysis of the central nervous system after the sensory cortex is suppressed. The paralysis sequentially affects the basal ganglia, the cerebellum and then the spinal cord. The medulla, which controls respiratory, cardiac and vasomotor centers, is depressed by the anesthetic in a dose dependent fashion. When respiration is completely depressed by the anesthetic, it must be performed for the patient by the anesthesiologist, using either a rubber bag, or automatic ventilator.

Secondly, the patient should be sufficiently unconscious so as to feel no pain and be unaware of the operation. Patients have sued for medical malpractice because they felt pain during the operation or were aware of the surgical procedure. Once unconsciousness has been achieved, powerful depolarizing and non-depolarizing muscle relaxant drugs can be given to assure a quiescent undisturbed operating field for the surgeon.

Thirdly, the anesthesia should not be administered in an amount so as to lower blood pressure to the point where blood flow to the brain may be reduced to a dangerous extent to cause cerebral ischemia and hypoxia. The dangerous extent is generally below 50 mm Hg for mean arterial pressure (MAP). For example, if the blood pressure is too low for over 10 minutes, the patient may not regain consciousness. This critical pressure will vary with the patient's medical condition. In patients with hypertension, for example, the critical pressure below which injury can occur, is elevated.

A skilled anesthesiologist may monitor the vital signals such as breathing, heart rate, and blood pressure of the patient to determine if more or less anesthetic is required. Often, the anesthesiologist looks into the patient's eyes to determine the extent of the dilation of the pupils as an indication of the level or depth of the effect of the anesthesia. The depth is also called "plane of anesthesia." However, there may be a number of problems with such complete reliance on the skill and attention of the anesthesiologist. In modern practice, the eyes are frequently taped shut to avoid abrasion or ulceration of the cornea of the eye. Since some operations may be prolonged for 10 to 15 hours, the attention of the anesthesia nurse or anesthesiologist may flag or fail. Therefore, it is important to provide a simple method to monitor the patient's state of the cardiovascular system.

The state or performance of the cardiovascular system can be described in terms of hemodynamic parameters. One such parameter is the cardiac output (CO). Much effort has been invested in non-invasive methods to measure the CO. (See Klein, G., M.D., Emmerich, M., M.D., Clinical Evaluation of Non-invasive Monitoring Aortic Blood Flow, (ABF) by a Transesophageal Echo-Doppler-Device. Anesthesiology 1998; V89 No. 3A: A953; Wallace, A. W., M.D, Ph.D., et.al., Endotracheal Cardiac Output Monitor, Anesthesiology 2000; 92:178-89). But the cardiac output is just a summary parameter or a final common result of many possible hemodynamic states. In clinical practice, fluid administration and vasoactive drug infusion therapy are not directed to changing the CO per se. Rather, they are directed to the CO's component parameters such as the heart rate (HR) and the Stroke Volume (SV). The relation among the HR, the SV and the CO is given by $$CO = HR[SV] \qquad \text{Eq. 1}$$

The SV, in turn, is a function of three constituent parameters. The Preload (P) measures the "tension" in cardiovascular muscle at end diastole. The Afterload (A) measures the "resistance" to the blood outflow from the left ventricle. The Contractility (C) measures the rate of rising of the "strain" in cardiovascular muscle. SV increases with increasing P and C and decreases with increasing A. (See Braunwald, E., M.D., ed., Heart Disease, A Textbook of Cardiovascular Medicine, Fourth Edition, Philadelphia, W.B. Saunders Company, 1992, p. 420). In other words, the following relation holds.

$$SV = f(P,A,C) \qquad \text{Eq. 2}$$

where f ( ) is a predetermined function.

One way of looking at Eq. 2 is to understand that SV is a function of a vector in a three dimensional space. This vector is just (P,A,C). The axes of the vector space are mutually perpendicular and include P, A, and C. By Eq. 1, CO is linearly proportional to SV by the factor of HR. We can therefore understand that HR is scalar and operates on a vector in a three dimensional, hemodynamic vector space, H. Substituting Eq. 2 in Eq. 1, we have $$CO = HR[f(P,A,C)] \qquad \text{Eq. 3}$$

Every possible hemodynamic state in a given system is represented by a unique point in the (P,A,C) space and is scaled by HR. There is a subset of points within H, that are compatible with life. The subject is a physiologic hemodynamic vector subspace that we can call P. P is wholly contained in H. If we can track the position of the hemodynamic vector in this hemodynamic vector space, that is, follow its trajectory, then we can have fairly complete knowledge of what the effects of pharmacologic and fluid therapy are during the perioperative period. We can titrate fluids and diruetics, pressors and afterload reducers, anesthetics, inotropes and negative inotropes against a change in the position of the vector and its relative projection onto each of the three mutually perpendicular axes.

Preload, Afterload, and Contractility have been traditionally assessed by invasive methods. Preload has been approximated by Pulmonary Capillary Wedge Pressure (PCWP), which is measured with a Swan-Ganz pulmonary artery balloon-tipped catheter that is wedged into the pulmonary arterial circulation. Preload has also been approximated by measuring the area of the left ventricle image at end-diastole with 2-D echocardiography. Afterload has been approximated using the Swan-Ganz catheter to perform thermodilution cardiac output measurements, and measurements of Mean Arterial Pressure (MAP) and Central Venous Pressure (CVP) to calculate the Systemic Vascular Resistance. This is done in analogy with Ohm's law for electrical resistance. In clinical practice, Contractility is approximated as the cardiac ejection fraction. This requires the methods of nuclear medicine or 2D echocardiography. Alternatively, Contractility is approximated as the maximum rate of rise of left ventricular pressure (P) in systole. This is just the maximum value of the first derivative of pressure with respect to time during systolic ejection. That is, the approximation is dP/dt max. (See Braunwald, E., M.D., ed., Heart Disease, A Textbook of Cardiovascular Medicine, Fourth Edition, Philadelphia, W.B. Saunders Company, 1992, p. 431). Measuring dP/dt max requires catheterization of the left ventricle. This hazardous and arrythmogenic procedure is usually reserved for the cardiac catheterization lab.

Swan-Ganz catheters are invasive. Invasion is the occasion of clinical mischief. Most experienced clinicians understand this in a visceral way. Pulmonary artery rupture, hemo-pneumothorax, pulmonary infarcts, bacterial endocarditis, large vein thrombosis, and intraventricular knotting are just a few of the well-known complications that result from using this device. Some authors have advocated a moratorium on their use, believing that the risks outweigh the benefits. (see Connors, A. F. Jr., M.D., et. al., The Effectiveness of Right Heart Catherization in the Initial Care of the Critically Ill Patients, J. Amer. Med. Assn., 1996; 276:889-897; Dalen, J. E., Bone R. C.: Is It Time to Pull the Pulmonary Catheter? J. Amer. Med. Assn., 1996; 276:916-8). 2-D transesophageal echocardiography devices are prohibitively expensive. They also require specialized image interpretation skills. They are still minimally invasive. Likewise, the methods of Nuclear Medicine are expensive, requiring a cyclotron to produce specialized radiopharmaceuticals and specialized image interpretation skills. Moreover, Nuclear Ejection Fractions cannot be done continuously and in real time. They can be used to assess baseline cardiac function. They cannot be used to titrate fluid therapy and drug infusions from moment to moment.

Newer technologies have emerged such as the Hemosonic device from Arrow International (see Klein, G., M.D., Emmerich, M., M.D., Clinical Evaluation of Non-invasive Monitoring Aortic Blood Flow, (ABF) by a Transesophageal Echo-Doppler-Device. Anesthesiology 1998; V89 No. 3A: A953). This minimally invasive device uses a trans-esophageal Doppler placed in the esophagus and one-dimensional A-mode echocardiograph. The Doppler measures velocity of blood in the descending aorta while the A-mode ultrasound is used to measure the descending aortic diameter in real time. Integrating blood velocity times aortic diameter over the ejection interval gives the stroke volume. Stroke volume times heart rate gives cardiac output. Dividing cardiac output into the Mean Arterial Pressure gives Systemic Vascular Resistance. Measuring peak blood acceleration gives Contractility. Because the device measures blood flow in the descending aorta, it ignores blood flow to the head and both arms. Thus, it ignores about 30% of the total cardiac output and cannot measure Preload. Because the device sits in the thoracic esophagus, it cannot be used on people who are awake.

If it were possible to approximate Preload, Afterload, and Contractility using non-invasive means or equipment which is already ubiquitous and relatively inexpensive, then many more patients on whom invasive monitors and 2D echocardiography devices are not currently used, could benefit from hemodynamic monitoring without its high costs and high risks. This possibility includes many pediatric patients, renal patients, pregnant patients, and cardiac patients presenting for non-cardiac surgery. The above described non-invasive hemodynamic monitoring on a beat-to-beat basis would represent a great improvement in the state of the art, resulting in significant reductions in the cost of care and in perioperative morbidity.

There is a need for a low-cost, low risk, non-invasive metric against which a wide array of cardiovascular support drug administrations and infusions can be adjusted, in order to optimize the condition of patients with a wide variety of cardiovascular medical conditions, within the constraints of said conditions and illnesses. Because of its low-cost, low-risk character, it should render possible the non-invasive clinical monitoring of a wide range of cardiovascular illness, in the operating room and intensive care unit, and also from locations outside the traditional operating room theater and critical care units. It should allow clinicians to pinpoint and quantify the component causes of acute decompensations in chronic cardiovascular illness, and to use this information to modify therapy in such a way as to prevent frequent, costly hospitalization.

Accordingly, there is a need to provide apparatuses and methods for continuously and accurately providing real-time information relating to cardiac output in the form of volume blood flow based upon non-invasive measurements. There is also a need to provide apparatuses and associated methods for monitoring cardiac output which results in a reduced likelihood of an undetected catastrophic event. Additionally, there is a need to provide a method for monitoring cardiac output in which the risk of infection is eliminated or significantly reduced.

Accordingly, it is an objective of the present invention to provide devices and methods for detecting, assessing the cardiac timing of, grading, and diagnosing a variety of vascular and arrhythmia conditions.

It is another objective of the present invention to provide devices and methods for non-invasively monitoring the hemodynamic state of a patient and providing approximate information on the Preload, Afterload and Contractility.

It is to be noted that the scope of this invention is not simply in the sphere of anesthesia, but in the totality of medicine, including outpatient, ambulatory, and critical care medicine. For example, it solves the problem of optimizing fluid administration and the use of diuretics and inotropes (like digitalis) and afterload reducers, like the vasodilator Captopril, in patients with Congestive Heart Failure (CHF). Too little fluid, and the cardiac output becomes insufficient to perfuse vital organs like the brain, heart, and kidney, resulting in organ failure and death. Too much fluid, and the pumping capacity of the compromised left heart is overwhelmed, allowing fluid to back up into the lungs, causing a diffusion barrier to oxygenation. Fluid welling up in the lungs effectively causes the patient to drown. In this circumstance, patients need to be hospitalized, intubated, and ventilated in an ICU. By adjusting the diuretic dose against the Preload, or its analogue, and by adjusting the Digitalis dose against the contractility, and adjusting the Captopril dose against the SVR or its analogue, you can keep someone with CHF out of the hospital for longer periods of time, saving both money and grief.

SUMMARY OF THE INVENTION

In a first aspect, the present invention provides a system for retrofitting existing non-invasive cardiac parameter measuring devices to generate invasive cardiac analogues, including; an interface unit for receiving predetermined non-invasive cardiac parameters into a plurality of the invasive cardiac analogues based upon a set of predetermined conversion equations, wherein the conversion unit outputs the predetermined invasive cardiac analogues including preload as denoted by P, afterload as denoted by A and contractility as denoted by C.

DETAILED DESCRIPTION OF THE PREFERRED EMBODIMENTS

Figure 1:
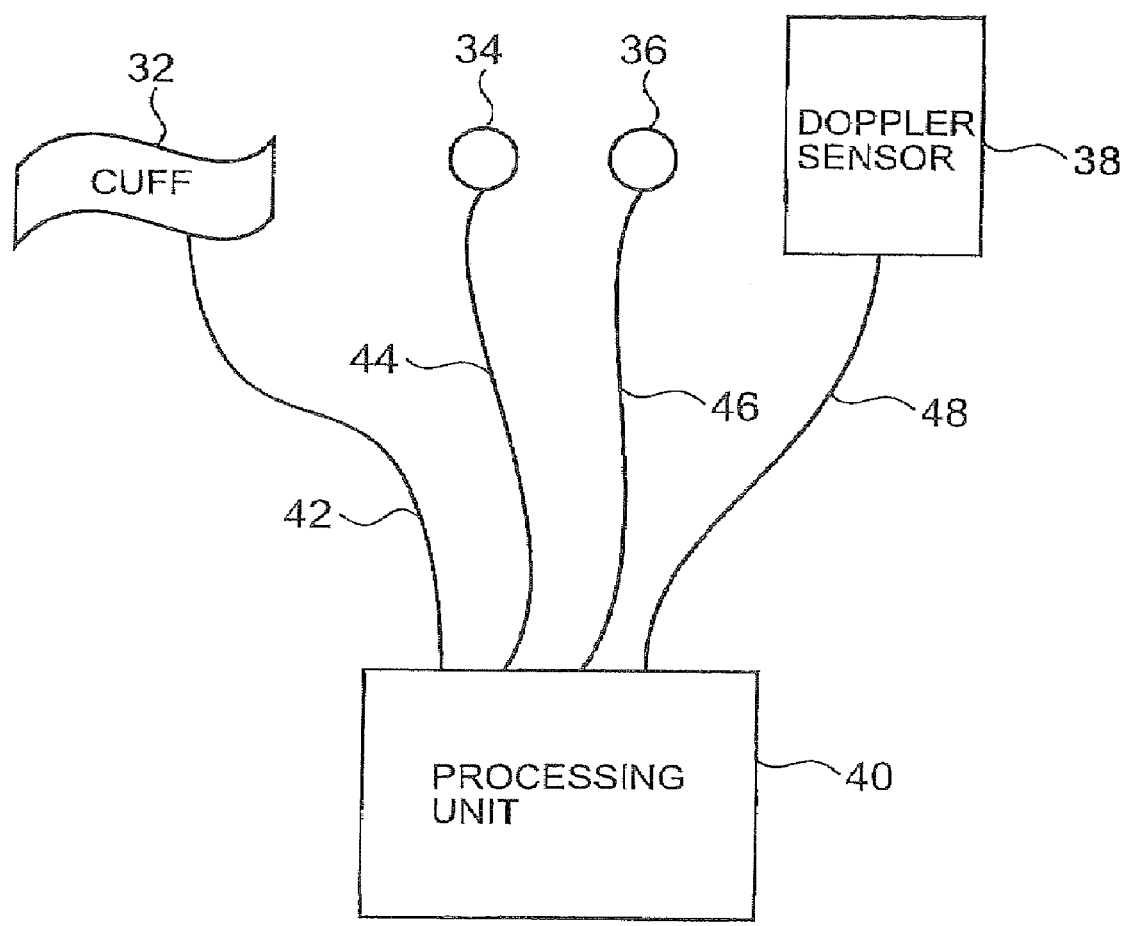
FIG. 1 is a diagram illustrating one preferred embodiment of the device for non-invasively monitoring a patient's cardiac parameters according to the present invention.

Left Ventricular End-Diastolic Pressure (LVEDP), Systemic Vascular Resistance (SVR) and the Maximum Rate of Rise of Left Ventricular Pressure (dp/dtmax) are respectively clinically useful indices and invasive cardiac analogues of or approximations to Preload, Afterload and Contractility. Even though these respective pairs of cardiac parameters are not perfectly linear with respect to one another, they are monotonically increasing with respect to each other. Therefore, LVEDP, SVR and dP/dtmax are also cardiac parameters that are responsive to cardiac medicines such as fluids and diruetics, pressors and afterload reducers, anesthetics, inotropes and negative inotropes. That is precisely why clinicians can rely on LVEDP, SVR and dp/dtmax to administer the proper dosage of medicines for further controlling these parameters and therefore for adjusting the state of hemodynamics of the patient.

In addition, it is an accepted tenet of physiology that a complete description of the functional state of the heart is given by four parameters. They are the heart rate, the LVEDP, the SVR, and dP/dtmax. (See Braunwald, E., M.D., ed., Heart Disease, A Textbook of Cardiovascular Medicine, Fourth Edition, Philadelphia, W.B. Saunders Company, 1992, p. 374-82). The last three of these, which determine the stroke volume, has been typically obtained only at the cost of invasion of the patient.

By making the appropriate substitutions for Preload, Afterload, and Contractility, we can rewrite Eqs. 2 and 3 respectively as, $$SV=f(LVEDP,SVR,dP/dtmax) \quad \text{Eq. 4, and}$$

$$CO=HR[f(LVEDP,SVR,dP/dtmax)] \quad \text{Eq. 5}$$

Therefore, the state of a hemodynamic system is substantially described based upon the above four parameters. Three of these parameters constitute a vector in a three-dimensional vector space, H'. The axes of H' are LVEDP, SVR, and dP/dt max with appropriate units. A function 'f' of this vector determines the stroke volume, SV. The fourth parameter, the heart rate HR operates linearly as a scalar on the vector to determine the cardiac output, CO.

In a first aspect, the present invention provides a non-invasive method of monitoring a patient's first plurality of cardiac parameters responsive to medicines, measuring non-invasively a second plurality of cardiac parameters and converting the second plurality of cardiac parameters into the first plurality of cardiac parameters that are directly responsive to external medicines.

In a preferred embodiment of the present invention, the first plurality of cardiac parameters are LVEDP, SVR, and dP/dtmax, which are directly responsive to cardiac medicines such as fluids and diruetics, pressors and afterload reducers, anesthetics, inotropes and negative inotropes. More preferably, the first plurality of cardiac parameters further include heartrate (HR). The second plurality of cardiac parameters is non-invasively measured directly using proper instrumentation. The second plurality of non-invasively measured parameters includes mean arterial pressure (MAP), the Ejection Interval (EI) and Electrical-Mechanical Interval (E-M). More preferably, the second plurality of non-invasively measured parameters further includes Heart Rate (HR), which together with MAP, EI and E-M substantially gives a complete description of the function state of the heart.

EI is the time interval during which systolic ejection takes place. It starts when the aortic valve opens and ends when it closes. If an ordinary Doppler ultrasound device is placed over the suprasternal notch near the ascending aorta, inspection of the frequency vs. time curve will yield the EI. Also, since the time from mitral valve closure to aortic valve opening in systole is small compared to the Ejection Interval, the interval from the first heart sound to the second heart sound measured using a stethoscope or phonocardiogram is optionally a useful approximation to the EI.

E-M is defined by the time between two specific events, an electrical event and a mechanical event. The electrical event is an event detectable on the EKG, which initiates ventricular contraction. The electrical event can be the Q-wave, the R-wave or the S-wave. In each case, Q, R or S is respectively defined as a point in time when the Q-wave, the R-wave or the S-wave reaches a particular point such as a maximum, a minimum or other predetermined point on the wave. The event is optionally a ventricular pacing spike.

In some arrhythmias, like ventricular tachycardia with a pulse, there IS no Q-wave (or R-wave, or S-wave). Therefore, another embodiment of 'E' of the E-M interval is to look at the EKG waveform defining ventricular depolarization, differentiate it twice with respect to time, and define the point in time at which the electrical depolarization wave accelerates maximally upward as 'E'. This would allow for the definition of an E-M interval in those instances where there is no recognizable Q, R, or S wave, i.e. when the patient is in extremis. For instance, in ventricular tachycardia, the waveform looks like a rapid sine wave. This alternative embodiment of 'E' may also turn out to be a practically more accurate way to determine E-M by more accurately defining 'E', to within narrower tolerances. The main point, is to find and accurately define a physiologically identical time point in all possible EKG ventricular depolarization cycles, which are then compared to one another to create consistent usable E-M intervals.

The mechanical event is a palpable consequence of ventricular contraction. It is related to the electrical event and lags the electrical event in time. The upstroke of the arterial trace from an indwelling arterial catheter qualifies as a mechanical event, and so does the instant at which the upward acceleration of the arterial pressure trace is at maximum. In other words, a mechanical event occurs at the instant of maximum value of the second derivative of pressure with respect to time. If the arterial blood pressure (ABP) is given by A(t), then the mechanical event is given by A"(t)max or A"max for simplicity. Therefore, in one embodiment, the E-M interval (E-M) is further defined as Q-A"max, R-A"max or S-A"max.

If we place a Doppler device over a major artery such as the ascending thoracic aorta near the sternal notch, then the instant of flow velocity upstroke with the onset of systole qualifies as a mechanical event. If Doppler detected flow is given by F(t), then the instant at which the acceleration in flow is maximum or F"(t) max is also, a useful mechanical event. Therefore, in another embodiment, the E-M interval (E-M) is defined as Q-F"(t)max, R-F"(t)max or S-F"(t)max.

A useful mechanical event is also obtained from the upstroke of the optical plethysmographic curve using a pulse oximeter placed on a patient's finger, toe, nose or earlobe. Similarly, the instant of maximum upward acceleration of the plethysmographic curve (PM(t)) is a clinically useful mechanical event. In one embodiment, the mechanical event is defined as the instant at which the PM(t) curve hits a minimum prior to the detection of flow. Alternatively, the mechanical event is defined as the instant at which PM(t) curve accelerates maximally upward as flows become rapid. Differentiating the PM(t) curve twice with respect to time give us the PM"(t). The instant at which PM"(t) reaches a maximum value, following the Q-wave (or its substitutes) defines a Q-PM"(t)max interval, which is a further embodiment of the E-M interval (E-M).

The onset of the first heart sound, representing the closure of the mitral valve optionally likewise serves as a useful mechanical event. The instant of maximum amplitude of the first heart sound is optionally used as a mechanical event as well. It matters little which event is used to define the E-M interval according to the current invention. By analogy, the E-M interval is like the interval between a flash of lightning and a clap of thunder. It matters only that we use the same one consistently when making comparative judgments.

A particular mechanical event is detected using a physiologic sensor developed at Empirical Technologies Corp to define the E-M interval. This technology uses a fiberoptic device that sits over the radial artery and vibrates with the arrival of the pulse wave. The vibration of the fiberoptic element due to the arterial pulse wave affects the transmission of a beam of light inside.

Another embodiment detects the mechanical event by placing a fiberoptical seismometer device over a large artery to measure the displacement of the arterial wall transverse to the direction of blood flow. The displacement of the arterial wall transverse to the direction of blood flow with respect to time t is defined as TD(t). By analogy, an E-M interval is defined as Q-TD"(t)max. TD"(t)max is the time when TD"(t), which is the double differentiate of TD(t), reaches its maximum value.

Using the interval between the trough of the Q-wave on EKG and the upstroke of the arterial pressure wave in a major artery, the Q-A interval (one type of E-M interval), the quantification of myocardial Contractility was first described in a letter to the editor of the Lancet by Jackson, in 1974. (see Jackson, D. M., M.D, A Simple Non-Invasive Technique for Measuring Cardiac Contractility, [Letter]. Lancet 1974; ii:1457). Using human volunteers, he plotted the decrease in the Q-A interval from baseline at one-minute intervals, while infusing isoproteranol. As the infusion came to equilibrium, he described a linear decrease in the Q-A interval with respect to time. He then doubled the rate of the infusion and obtained a further linear decrease in the Q-A interval over time. Of interest, at the lower rate of isoproteranol infusion, the Q-A interval significantly decreased in comparison to baseline while the heart rate changed relatively little. This showed that the decreased Q-A interval was due to an increase in the inotropic state of the myocardium and not due to an increase in the heartrate. He also described a positive correlation between dP/dtmax and the decrease in the Q-A interval in anesthetized beagle dogs with left ventricular catheters. He affirmed this correlation using five different agents, all of which have an effect on the inotropic state of the myocardium, thiopental, calcium, isoproteranol, norepineprine and digitalis.

In another letter to the editor of the Lancet two months later, Rodbard (see Rodbard, S., Measuring Cardiac Contractility, [Letter]. Lancet 1975; I: 406-7) indicated that he had used Jackson's approach for at least a decade earlier particularly in the diagnosis and evaluation of hyperthyroid and hypothyroid states. Rodbard described the measurement of the interval from the Q-wave to the Korotkoff sound over a major artery, the Q-Korotkoff interval (Q-K interval) as well as using a Doppler ultrasound device placed over a major artery to generate a Doppler frequency shift versus time curve (D(t)) to measure the Q-D(t) interval (or Q-D interval).

In contrast, according to the present invention, a more preferred mechanical event is defined by D"(t)max, the time t at which D"(t) reaches maximum value following the peak of the Q-wave or its substitute. Similarly, D"(t) is derived by differentiating D(t) twice against time t.

In general, by differentiating a physiologic function M such as A(t), PM(t), F(t), TD(t) or D(t) twice to obtain the time of a useful mechanical event, an improved accuracy of E-M is achieved. In a preferred embodiment, the mechanical event of E-M is defined as E-M"max, where M"max is defined at the time when M", which is obtained by double differentiating the physiologic function M against time t, reaches a particular maximum.

The shorter the E-M interval is, the greater the Contractility of the myocardium becomes. The relation between Q-A, Q-K or Q-D interval and Contractility or dp/dtmax has long been in the public domain. (see Cambridge, D., Whiting, M., Evaluation of the Q-A interval as an Index of Cardiac Contractility in Anesthetized Dogs: Responses to Changes in Cardiac Loading and Heart Rate. Cardiovascular Research 1986; 20: 444-450). However, as will be disclosed later, the E-M interval is not only correlated with Contractility but also is used to correlate with other cardiac parameters which are responsive to medicines.

In summary, cardiac output and cardiac state of a patient are correlated to HR, EI, MAP and E-M, which are the second plurality of cardiac parameters that are non-invasively measured in a direct manner. Therefore, we arrive the following equations, where CO is linear to HR.

$$CO = HR[f(EI, MAP, E-M)], \qquad \text{Eq. 6}$$

$$SV = f(EI, MAP, E-M) \qquad \text{Eq. 7}$$

The above relations are mathematically and logically equivalent to the relations among the invasively measured quantities (P, A, C) or its equivalents (LVEDP, SVR, dP/dtmax).

A first three-dimensional non-invasive vector space M with three mutually perpendicular axes EI, MAP and E-M is constructed even though it is not directly responsive to the external medicines. For every point in the invasive hemodynamic vector space H', there exists exactly one corresponding point in the non-invasive hemodynamic vector space M. Moreover, every point in the non-invasive hemodynamic vector space M has an image in the invasive hemodynamic vector space H'. In the language of linear algebra, there is a mathematical mapping from the non-invasive hemodynamic vector space M to the invasive hemodynamic vector space H' in a 'one-to-one' and corresponding manner. Therefore, in one aspect, the present invention demonstrates there is a one-to-one correlation between the non-invasive hemodynamic vector space M and the invasive hemodynamic vector space H'.

A particular hemodynamic state vector in the (EI, MAP, E-M) space does not directly show the equivalents or analogues of the invasive parameters, such as (P, A, C) or (LVEDP, SVR, dP/dtmax). In order to get to an analogue vector in the (P, A, C) or (LVEDP, SVR, dP/dtmax) space from the non-invasively measured vector in the (EI, MAP, E-M) space, a predetermined transformation on the (EI, MAP, E-M) vector is needed. Therefore, the first aspect of the present invention is directed to a correlation between the above described two vectors or a method of converting a vector in the (EI, MAP, E-M) space into an equivalent vector in the (P, A, C) or (LVEDP, SVR, dP/dtmax) space. This conversion may be implemented in many different forms such as a computer program residing on a computer.

In one preferred embodiment of the transformation method according to the present invention, the transformation is accomplished by multiplying the (EI, MAP, E-M) vector by a diagonal matrix as shown below. Let x be a vector in the non-invasive hemodynamic space M of the form (EI, MAP, E-M). Let A be the diagonal matrix shown below. If we represent x vertically as a column vector, we can multiply it by the matrix A such that Ax=b, where b is a vector of the form ((EI*MAP*E-M), (MAP*E-M), 1/(E-M)), that is approximately equivalent to (LVEDP, SVR, dP/dtmax), and a first embodiment of the first plurality of cardiac parameters responsive to external medicines as being demonstrated in the equation below.

$$\begin{pmatrix} MAP*(E-M) & 0 & 0 \\ 0 & E-M & 0 \\ 0 & 0 & 1/(E-M)^2 \end{pmatrix} \begin{pmatrix} EI \\ MAP \\ (E-M) \end{pmatrix} =$$

$$(EI*MAP*(E-M), MAP*(E-M), 1/(E-M))$$

The above operation of multiplying the vector by a matrix linearly transforms the vector x into the vector b. Vector b constitutes a new vector space N or a second Non-invasive Space whose axes are responsive to external medicines as being verified below. The three mutually perpendicular axes of the vector space N are EI*MAP*E-M, MAP*E-M, and 1/E-M. The first axis, (EI*MAP*E-M) is linearly proportional to the LVEDP to a first approximation. The second axis, (MAP*E-M) is linearly proportional to SVR to a first approximation. The third axis, (1/E-M) is linearly proportional to the natural logarithm of dP/dtmax or ln(dP/dtmax) to a first approximation. These relations are summarized as follows:

$$LVEDP = k1(EI*MAP*E-M) + c1 \qquad \text{Eq.8}$$

$$SVR = k2(MAP*E-M) + c2 \qquad \text{Eq.9}$$

$$\ln(dP/dt)max = k3(1/E-M) + c3 \qquad \text{Eq.10}$$

Solving Eq. 10 for dP/dt max, $$dP/dtmax = Z[\exp(k3/E-M)], \text{ where } Z = \exp(c3) \qquad \text{Eq. 11}$$

where k1, k2, k3, and c1, c2, c3 are empirical proportionality constants.

Eqs. 8 through 11 are true only to a first approximation. That is because while the left hand members of Eqs. 8 through 10 do increase monotonically with respect to the right hand members, the increases may not be perfectly linear with respect to one-another. As the patient deviates further from the physiologic norm, the size of the non-linearity increases. This is because the relations between the left and right hand members of Eqs. 8 through 10 are more subtly exponential than linear. So within an arbitrarily large neighborhood of a given physiologic point, the tangent to the subtle exponential curve gives a reasonably good approximation. However, since they are monotonically increasing with respect to one-another, they are practically useful in controlling proper medicine administration. (EI*MAP*E-M), (MAP*E-M) and (1/E-M) are used to judge the changes in the Preload, Afterload, and Contractility due to fluid and drug administration.

In addition to generating a data stream of hemodynamic state vectors describing Preload, Afterload, and Contractility on a beat-to-beat basis, the method of the present invention also yields a similar data stream about Stroke Volume, SV. SV is a function of only two of the non-invasive quantities, the Ejection Interval, (EI) and the E-M interval (E-M). In other words, the following equation expresses the relation $$SV = f(EI, E-M) \qquad \text{Eq.12}$$

Let the average rate of outflow of blood from the Left Ventricle during the ejection interval be Fei in cc/sec. Then by definition, the following relation exists.

$$Fei = SV/EI \qquad \text{Eq.13}$$

Based on the experimental results disclosed in the present invention, Fei is empirically and linearly proportional to the transcendental number $e^{1/E-M}$. The quantity 1/E-M is the time rate at which electromechanical transduction and elastic propagation of the pulse wave or analogous mechanical events occur. So we can write, $$Fei = k4 * \exp(1/E-M) + c4 \qquad \text{Eq.14}$$

Where k4 and c4 are empirical proportionality constants.

Solving Eq.13 for SV, we have $$SV = EI * Fei \qquad \text{Eq.15}$$

Substituting for Fei using Eq. 14, Eq. 15 becomes $$SV = EI * [k4 * \exp(1/E-M) + c4] \qquad \text{Eq.16 or}$$

$$SV \propto EI * [\exp(1/E-M)] \qquad \text{Eq. 16a}$$

Where "∝" means "proportional to." There are alternative formulations of SV such as the length or norm of the vector sum of two orthogonal vectors. One of the two orthogonal vectors is a function of EI, and the other is a function of (E-M).

In a second embodiment, the diastolic filling interval (DI) is used to replace EI. The correlation is improved between (DI, MAP, E-M), which is of the second plurality of non-invasively measured cardiac parameters and (LVEDP, SVR, dP/dtmax) or (P, A, C), which is the first plurality of invasive cardiac parameters in a second embodiment. In diastole, the left ventricular pressure is an exponential function of left ventricular volume, and this relation holds at any point during the diastolic filling interval including end-diastole. Therefore, LVEDP is an exponential function of Left Ventricular End Diastolic Volume (LVEDV).

To a reasonable approximation, $$DI = T - EI \qquad \text{Eq. 17}$$

where T is the time period of the cardiac cycle. T is easily obtained in a non-invasive manner by measuring the time interval between R-waves in the EKG and is linearly proportional to the reciprocal of the heart rate, HR in beats per minute. That is, $$T = (1/HR)*60 \text{ sec/min} \qquad \text{Eq. 18}$$

The above approximation ignores the time required for isovolumic contraction and relaxation. However, since the two intervals are relatively small fractions of any cardiac cycle, the approximation is useful.

A more accurate measure of DI is optionally obtained using a 1 MHz Doppler ultrasound device placed on the surface of the patient's chest just over the left ventricle. Diastolic filling has a characteristic low velocity blood flow that causes an analogously low Doppler frequency shift. The duration of the characteristic low frequency Doppler shift substantially serves as an accurate measure of DI. DI starts when the mitral valve opens, and it ends when the mitral valve slams shut. An ordinary stethoscope or phonocardiogram generally indicates when DI ends as marked by the first heart sound, the 'lub' of the two sounds 'lub-dub'. In patients with certain pathology, an opening snap of the mitral valve is audible in the stethoscope. Perhaps a phonocardiogram shows when the mitral valve opens in most patients. Alternatively, the above described fiberoptic sensor that is placed upon the precordium of the chest serves as a low cost 'seismometer' to measure the duration of the low frequency vibrations by diastolic filing in the amplitude of the fiberoptic light signal. The Doppler device is more expensive but has the advantage for obese patients. Therefore, the correlation between (DI, MAP, E-M) and (LVEDP, SVR, dP/dtmax) or (P, A, C) is defined by the following equations in the preferred embodiment:

$$\text{LVEDP} = k1'((T-\text{EI})*\text{MAP}*\text{E-M}) + c1' \qquad \text{Eq. 19}$$

$$\text{SVR} = k2'(\text{MAP}*\text{E-M}) + c2' \qquad \text{Eq. 20}$$

$$\ln(dP/dt)\max = k3'(1/\text{E-M}) + c3' \qquad \text{Eq. 21}$$

where k1', k2', k3', c1', c2' and c3' are constant for a particular patient.

Other hemodynamic parameters being equal, the longer the time interval over which the left ventricle fills, the higher its end-diastolic volume and pressure becomes. That is, the longer DI is, the higher the LVEDP becomes. If the EI by itself varies in a useful way with LVEDP, this is due to a law of physiology relating EI to DI in the steady state. EI by itself has no primary causal relation to LVEDP since it is defined by two events that occur in the cardiac cycle after the left ventricle has finished filling. The quantity DI=T−EI is logically, temporally and physiologically prior to the LVEDP. EI by itself is logically, temporally and physiologically posterior to LVEDP.

Using the above described correlation, we now have real-time and non-invasive measures to be used to express Preload, Afterload, Contractility, Stroke Volume, Heartrate, Cardiac Output, and Average Ejection Outflow Rate. From the foregoing equations, it is relatively simple to derive useful expressions for Left Ventricular Ejection Fraction, whose units are dimensionless, Left Ventricular Stroke Work in units of Joules, and Left Ventricular Power in Watts.

The existence of the correlation between the first plurality of cardiac parameters and the second plurality of cardiac parameters is verified by using the method of converting the second plurality of non-invasive cardiac parameters into the first plurality of cardiac parameters that are measured independently and invasively. The methods of measuring the first plurality of non-invasive cardiac parameters are well known to person skilled in the art. The following are exemplary methods.

Using the averaged waveforms, LVEDP is obtained by inspecting of the LVP(t) waveform and looking for the value of LVEDP just prior to the rapid increase in LVP due to systole. Contractility is obtained by differentiating the LVP(t) curve with respect to time, and recording the maximum value of the first derivative during systolic ejection, dP/dtmax. Afterload, which is approximated by Systemic Vascular Resistance (SVR) is obtained by the known formula (see Kaplan, J. A., M.D., Cardiac Anesthesia, Philadelphia, W.B. Saunders Company, 1993, p. 63)

$$SVR = \frac{(MAP - CVP)*80}{CO} \qquad \text{Eq. 22}$$

where MAP is the Mean Arterial Pressure in mmHg, and CVP is the Central Venous Pressure in mmHg. CO is the cardiac output in liters/minute. It is obtained using the thermodilution technique, with a Swan-Ganz catheter thermistor connected to a digital temperature vs. time curve integrator. The constant having a value of 80 is used to convert mmHg/(liter/min) into dyne*sec*cm$^{-5}$. CVP was recorded by hand from the monitor at each steady state as with MAP. HR, the heart rate/min, is obtained by measuring the period of the averaged EKG, taking its reciprocal and then multiplying by 60 sec/min. The HR is divided into CO to get the Stroke Volume (SV).

To create the non-invasive hemodynamic state vectors, the following approach is used. To measure the Ejection Interval, the LVP and Arterial Blood Pressures (ABP) are graphed simultaneously. The ABP trace is moved backwards in time until the LVP equals the Diastolic Arterial Blood Pressure. This moment in time marks the opening of the aortic valve. The curves are followed until they intersect again. This latter point marks the closure of the aortic valve. The Ejection Interval (EI) is just the time from opening to closing of the aortic valve. The Mean Arterial Pressure (MAP) is simply read from the monitor display. Alternatively, the ABP waveform is integrated over the cardiac period, and then the integral is divided by the period to get MAP, denoted MAPc. It does not make a significant difference which approach was used. As indicated previously, EI is easily obtained with an acoustic Doppler device placed in the suprasternal notch, over the ascending aorta. MAP is easily obtained using a blood pressure cuff and a (DINAMAP). These devices are ubiquitous and relatively inexpensive.

Therefore, in another aspect, the present invention provides a system to monitor a patient's cardiac parameters which are responsive to medicines with the use of a cuff, at least two electrodes from an EKG instrument, means to measure EI, and a processing means to convert the non-invasively measured cardiac parameters into invasive cardiac parameter analogues which are responsive to medicines.

FIG. 1 is a diagram illustrating one preferred embodiment of the system for non-invasively monitoring a patient's cardiac parameters according to the present invention. The system 30 in FIG. 1 includes a cuff 32, two electrodes 34 and 36, a Doppler sensor 38 to measure EI and a processing unit 40 to process the signals from the cuff 32, the electrodes 34 and 36, and the Doppler sensor 38. The cuff 32, the electrodes 34 and 36, and the Doppler sensor 38 are respectively connected to the processing unit 40 via electrical connections 42, 44, 46 and 48. The connections 42, 44, 46 and 48 might be the common electrical wires. Alternatively, the connections 42, 44, 46 and 48 might be wireless connections. The wireless connections such as infrared connection and microwave connection are well known to person skilled in the art. The system 30 is optionally manufactured to be portable. When the system 30 is used to measure or monitor a patient, the cuff 32 is attached to the patient's arm or other appropriate body parts while the electrodes 34 and 36 are attached to the outer skin in the patient's chest area with a predetermined distance between the electrode 34 and the electrode 36. Furthermore, the Doppler sensor 38 is placed in the suprasternal notch over the ascending aorta or over the carotid artery. The processing unit 40 controls the frequency of data acquisition and analysis and outputs the cardiac parameters of the patient. The output parameters are used by a medical practitioner to determine the patient's cardiac state and performance. That is, the medical practitioner determines whether or not any additional medicine is needed, and he/she also determines the type and amount of necessary medicines.

Figure 2:
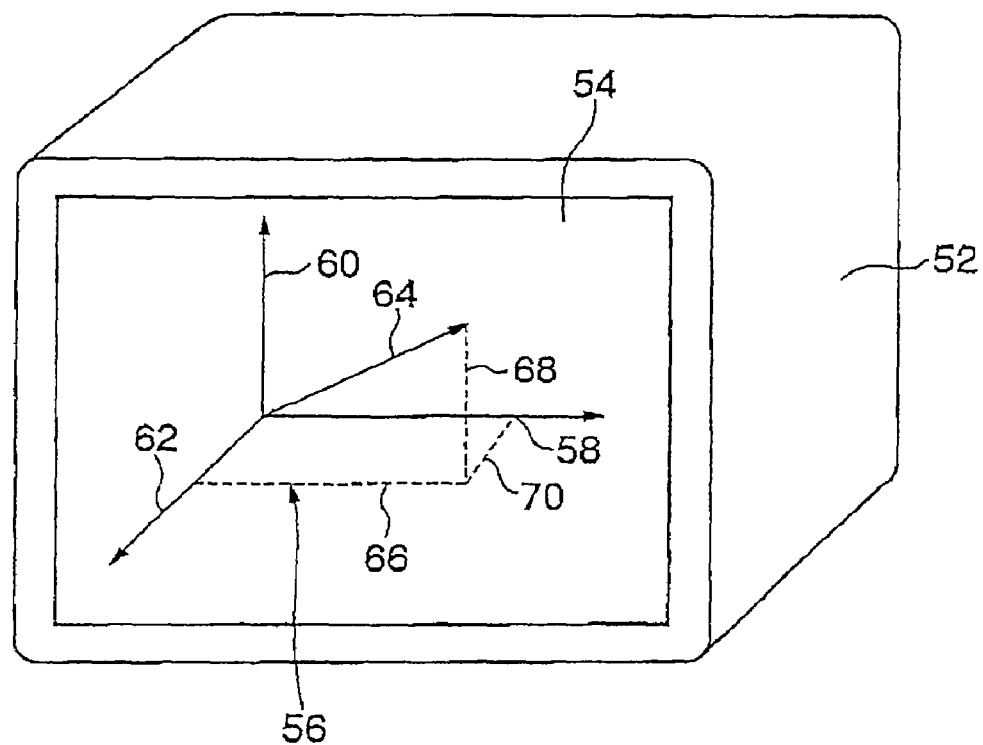
FIG. 2 is a diagram illustrating the first embodiment of the display of a hemodynamic state according to the present invention.

More preferably, the system of the present invention further includes a monitoring device which displays the output cardiac parameters on a screen as a three dimensional vector. One preferred embodiment of the display according to the current invention is illustrated by a diagram as shown in FIG. 2. The monitor 52 has a screen 54, which shows a three dimensional space 56 defined by the three dimensional axes 58, 60 and 62. The three dimensions 58, 60 and 62 respectively represent Preload, Afterload and Contractility or their equivalents based upon either invasive or non-invasive measurements. All the cardiac parameters are shown in the three dimensional space 56 as a vector 64. The projections 66, 68 and 70 of the vector 64 on the axes 58, 60 and 62 respectively represent the patient's Preload, Afterload and Contractility. The three dimensional graph on the screen allows a clinician to process a great deal of hemodynamic information at one glance. The display substantially improves vigilance in cardiovascular monitoring in the perioperative period.

Figure 3A:
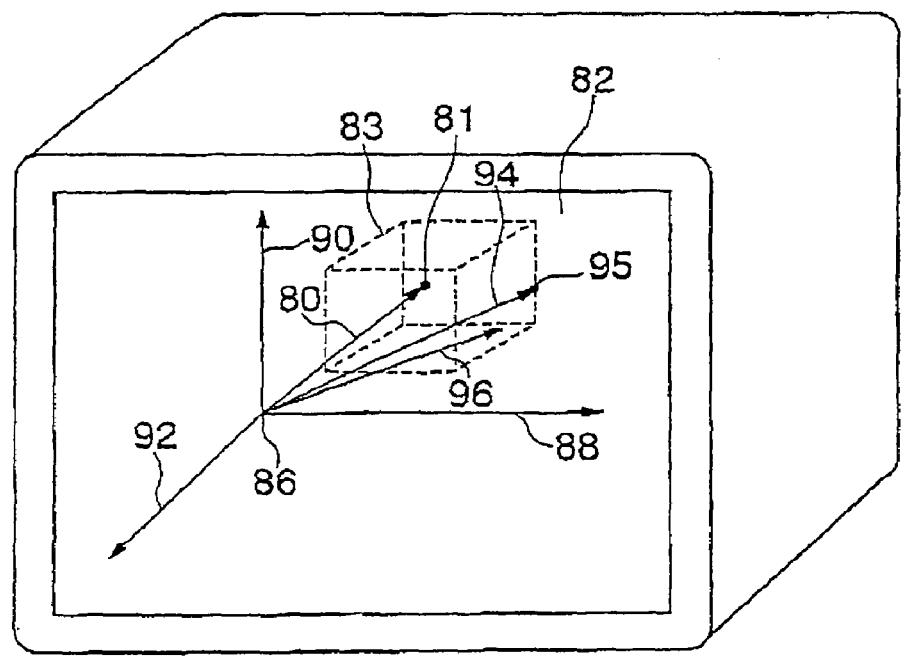
FIG. 3A is a diagram illustrating the second embodiment of the display of a hemodynamic state according to the present invention.

Even more preferably, as shown in FIG. 3A, in another preferred embodiment of the display according to the current invention, the system displays a vector 80 on the screen 82 that represents a 'safe' or 'normal' hemodynamic state or space. For instance, after the patient is sedated but before the surgery begins, the safe hemodynamic state is determined. By seeing how the vector 94 moves in real time relative to the norm vector 80, the operator or the clinician easily and visually perceives subtle changes in the patient's hemodynamic profile. The vector 94 is represented in computer graphics as a ray emanating from the origin 86. The projection of the vector 94 onto the Preload axis 88, Afterload axis 90, and the Contractility axis 92 are optionally made distinct in different colors. Likewise, the three components of the norm vector 80 are also optionally marked to create a basis of visual comparison. A parallel vector 96 in a contrasting color is overlaid upon the hemodynamic state vector 94. The length of the parallel vector 96 represents the size of the cardiac output which is the product of the stroke volume and the heart rate.

Optionally, in FIG. 3A, a box or a safety zone 83 is drawn on the screen 82 with the center of the box at the end point 81 of vector 80. Each edge of the box 83 is either parallel or perpendicular to the axes 88, 90 and 92. The length of the edges that are parallel to the Preload axis 88 represents the safe range of the patient's Preload. By the same token, the length of the edges that are parallel to the Afterload axis 90 and the Contractility axis 92 respectively represents the safe range of the patient's Afterload and Contractility. Therefore, as long as the end point 95 of the vector 94 is within the safe zone box 83, the vital cardiac parameters are considered to be within a predetermined acceptable range. On the other hand, if the end point 95 exits the box 83, an appropriate action such as infusion of a suitable medicine is needed so as to cause the end point 95 enter the box 83.

Figure 3B:
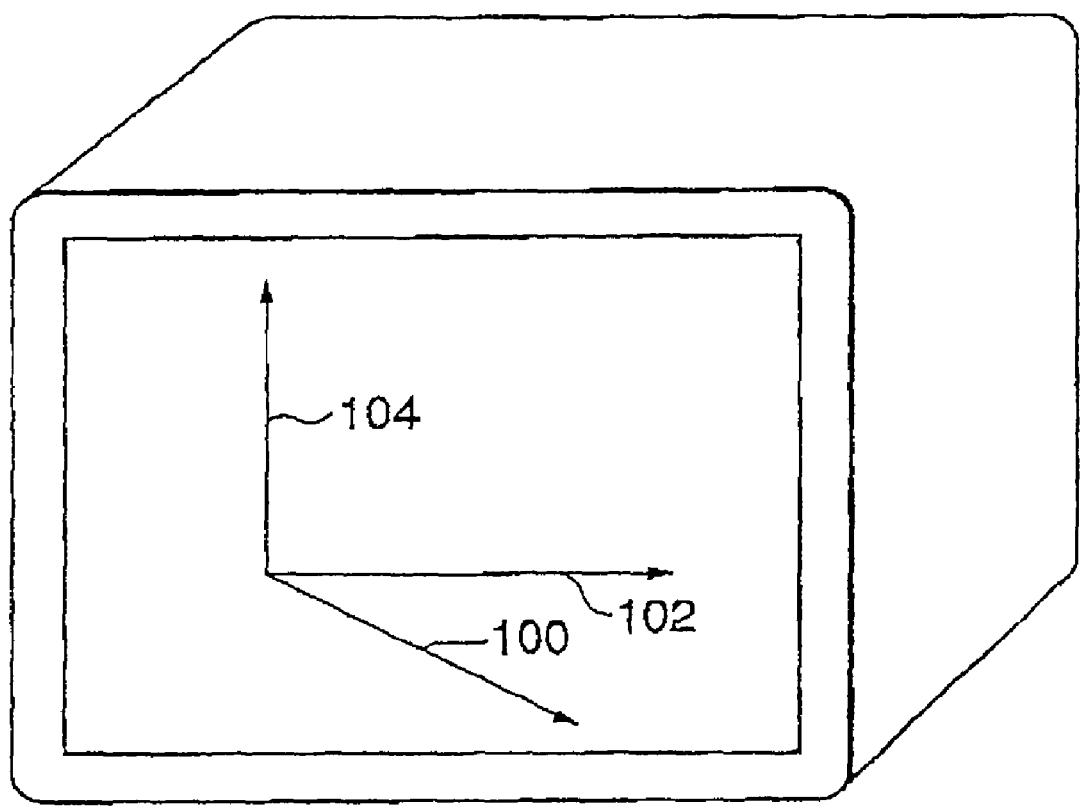
FIG. 3B is a diagram illustrating the third embodiment of the display of a hemodynamic state according to the present invention.

The deviation of the hemodynamic state vector from a physiological norm is indicative of an amount of physiological stress. The degree of physiological stress or deviation is defined by a vector cross product between the 'Normal' vector 100 and the Hemodynamic State Vector 102, and a vector 104 represents the vector cross product as shown in FIG. 3B. The vector cross product is a product of the length of the 'Normal' vector 100, the length of the Hemodynamic State Vector 102 and the sine of the angle between the two vectors. It has a direction of a line perpendicular to the plane that is defined by the original 'normal' vector 100 and the hemodynamic state vector 102. It also has an up or down sign relative to the above plane as given by the right hand rule.

The longer the length of the vector cross product 104, the more serious the patient's problem is. The length of the vector cross product is just the square root of the dot product of the vector cross product with itself. This quantity is just a scalar. As this length of the vector cross product exceeds a set of predetermined thresholds, a corresponding alarm or alert is optionally given to an operator or a clinician. Additional axes involving the oxygen saturation, the end-tidal carbon dioxide and the patient's temperature are alternatively combined in real time to create a multidimensional vector cross product. Other axes could be added as needed or as new modalities of monitoring are developed such as the processed EEG monitor (BIS) to gauge the depth of anesthesia. Obviously, vector spaces in excess of three dimensions are not easily displayed on a screen. But the length of the multidimensional vector cross product is easily displayed and is properly called a continuous Vital Function Scale. Arbitrarily large deviations from the norm alert the clinician to immediately correct the situation before the patient's life is threatened. The above described displays 2, 3A and 3B afford the clinician more time by providing the relevant cardiac data to rectify the problem. As the length of the vector cross product increases, the clinician is at least visually alerted as to the level of deviation from the norm.

Furthermore a computer program is implemented to quickly point the clinician's attention to which system or component of the multidimensional vector is a source of the problem so as to save precious seconds and to allow more time for a critical intervention. The above feature has strong implications for patient safety. The above displays 2, 3A and 3B also substantially reduce the level of skill needed to recognize the problem. In addition to the clinicians, some technicians who have not had the benefit of a medical school education would quickly be able to understand the significance of the information in the displays 2, 3A and 3B. The reduced skill level requirement is precisely because the system does not require arcane anatomic image or physiological waveform interpretation skills. The above described preferred embodiments are likely to be used with a short learning curve by anyone who can read a graph. Such an easy to learn system such as the displays 2, 3A and 3B also has implications for lowering the cost of health care.

Depending on how the hemodynamic state vector moves, various vasoactive agents are brought to bear upon the problem so as to move the patient's hemodynamics back toward the norm. Agents such as phenylephrine, nitroglycerine, nitroprusside, dopamine, dobutamine and esmolol are likely to help to stabilize sick patients undergoing the highly variable stresses of surgery. Vasoactive drug infusions are currently underutilized because not enough patients have the full metal jacket invasive cardiovascular monitoring that is needed to benefit from them. The system according to the present invention increases the wider usage of the easily adjustable vasoactive drugs that are now only routinely used during cardiac surgery.

Furthermore, the real-time hemodynamic data stream is used to control the vasoactive infusion pumps and the level of anesthesia itself via an appropriate computer program. For exemplary applications, the monitoring system of the present invention is placed at a patient's home and is made to communicate via the Internet to a website from which his or her physician downloads the patient's hemodynamic profile. Furthermore, the system is optionally made small enough to be worn by the patient. The monitored information is stored in the wearable system for over a 24 hour or longer period. The system of the present invention is alternatively used in the management of out patients with high blood pressure or congestive heart failure. The system allows the frequent adjustments of cardiac medications without the need for a patient visit. By allowing frequent and rapid dosage adjustments, the system prevents patients with congestive heart failure from being hospitalized for an acute decompensation. The above prevention capability would avoid enormous expenditures associated with hospitalization including intubation and ventilation of the patients in critical care units and management of their fluids with Swan-Ganz catheters. Alternatively, patients with cardiomyopathy and severe congestive heart failure also benefit from the system according to the current invention to adjust home dobutamine infusions while they await cardiac transplant.

Renal dialysis patients are similarly helped by the above described technology. For example, Preload of a renal dialysis patient at home is remotely monitored by a clinician while in his office via the Internet. The renal dialysis patient's hemodynamic profile is assessed non-invasively during dialysis. The information is used to manage p.o. fluid intake, restriction, and I.V. fluid administration. The information is also used by the renal dialysis patient himself to adjust his fluid intake in much the same way that a diabetic patient monitors his glucose level and adjusts his insulin dose and carbohydrate intake.

The measurement system is calibrated against itself, based upon using a vector arbitrarily designated as 'Norm' by the clinician when he observes the patient to be in no acute distress. Alternatively, the system undergoes a two or three point calibration against invasive measurements made by a cardiologist during cardiac catheterization. Catheterization is undergone only by the sickest patients to see if they are candidates for coronary artery stent placement, angioplasty, valve surgery, coronary artery bypass grafting or heart transplant. Once the calibration is made for a particular patient between the invasive measures and the non-invasive measures of cardiac function, it is reasonable that the calibration will persist for many years until the patient's anatomy significantly changes. The use of the current invention would radically decrease the cost of long term management of patients with severe cardiac disease who have had cardiac surgery. They would not need subsequent invasive measurements to get the hemodynamic information which is vital to their management. They can visit their doctors via the Internet using the methods such as telemedicine. It is an advantage that this measurement system significantly expands the scope of the patient services via telemedicine.

Figure 4A:
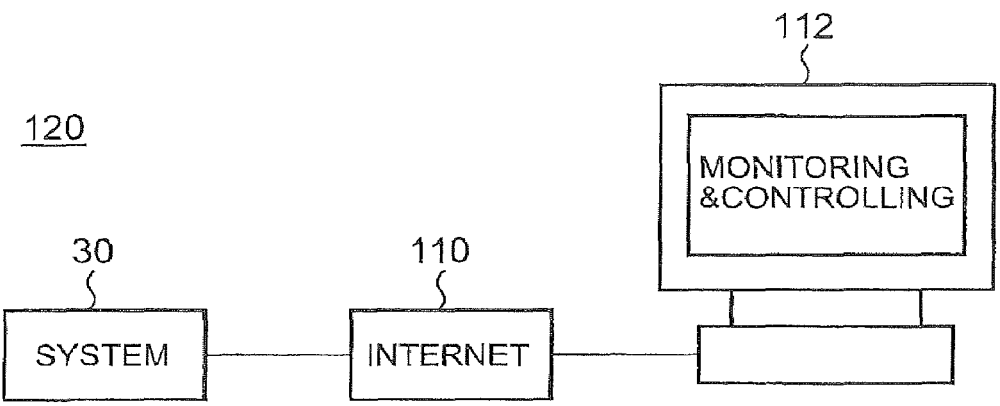
FIG. 4A is a diagram illustrating a first preferred embodiment of the system for performing telemedicine according to the current invention.
Figure 4B:
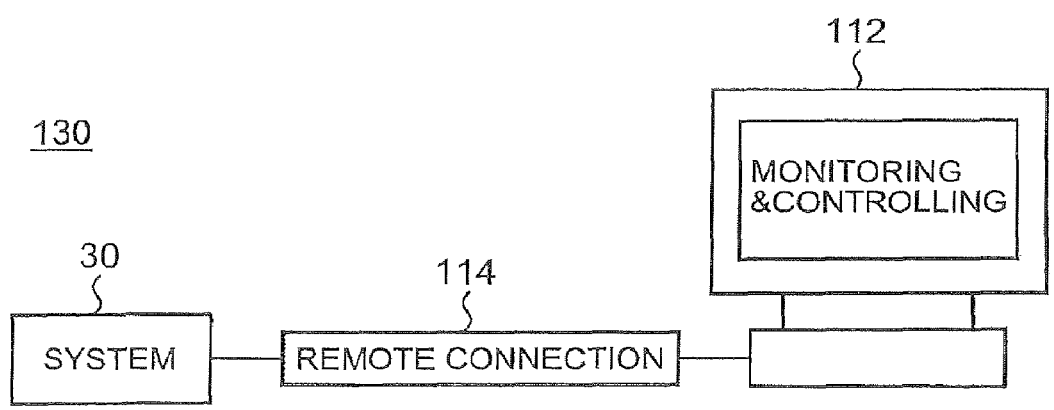
FIG. 4B is a diagram illustrating a second preferred embodiment of the system for performing telemedicine according to the current invention.

FIGS. 4A and 4B are diagrams illustrating preferred embodiments of the systems 120 and 130 for performing telemedicine according to the current invention. In FIG. 4A, one preferred embodiment of the system 30 according to the current invention as shown in FIG. 1 is connected to a monitoring and controlling unit 112 via the Internet network 110. For example, the system 30 is remotely located at a patient's home in order to non-invasively measure the patient's cardiac parameters while the monitoring and controlling unit 112 is located at a medical practitioner's office. Based upon the measurement results, the practitioner monitors the patient's cardiac conditions and optionally controls the system 30 to acquire additional information. In FIG. 4B, the system 30 of the present invention as shown in FIG. 1 is connected to a monitoring and controlling unit 112 via a remote connection device 114 via a dedicated or shared cable, a wireless telecommunication line or other suitable connection. The system 130 of FIG. 4B operates in a similar way as the system 120 of FIG. 4A.

The system of the present invention is used to detect an early warning sign of ischemia in a patient. With ischemia, there is a decrease in Contractility and a consequent increase in Preload as the heart tries to maintain cardiac output by moving up on the Starling curve, which a well know relationship between the Cardiac Output and Preload. Then, there is a reflex increase in the Afterload. The above attempt allows the body to maintain perfusion to vital organs in the face of a decreased cardiac output. These events form a recognizable profile in time with a signature time course. The system of the present invention likely recognizes the above constellation of events in real time by correlating the ischemia event with the non-invasively measured parameters and alerts clinicians of the presence and the extent of ischemic events. Among many possible correlations between ischemia and the non-invasively measured parameters, two useful aspects of the correlations are illustrated in the discussions below. Because decreases in Contractility with ischemia are prior to EKG changes in time, clinicians will have more lead-time to diagnose and treat life threatening ischemic episodes preceding myocardial infarction. Based upon the above early diagnosis, it is useful to have a nitroglycerine drip in hand in such circumstances. It is even more useful to have a physiologic real-time measurement to provide an end-point to which the nitroglycerine drip is titrated. Ultimately by preventing myocardial infarctions, the current invention helps saving the lives of potentially ischemic patients.

The present invention provides a device such as an interface which retrofits the existing hospital monitor units to monitor cardiac parameters in a non-invasive manner. The retrofit device of the present invention includes a means to measure EI and a processing means to convert the non-invasively measured results into cardiac parameters which are responsive to medicines. In one preferred embodiment of the retrofit system according to the current invention, blood pressure cuff and the EKG are used. Some other currently available devices carry out the non-invasive measurement of blood pressure by measuring the electromechanically transduced pulse wave at the wrist. Such a device could be used in the present system as well to measure MAP. Such a device is manufactured by MEDWAVE, 4382 Round Lake Road West, St. Paul Minn. 55112-3923, It sits on the wrist, on the radial artery, and non-invasively creates a pressure vs. time curve, which would yield MAP as well as 'M' of the E-M interval. The device is completely non-invasive, and its output is visually identical to what can be obtained form an indwelling, invasive arterial catheter pressure trace. The non-invasive measurement data is sent to the processing device via the interface unit for converting the data into a predetermined format.

In a more preferred embodiment, the fiberoptic sensor mentioned above, is placed over a large artery and yields information on MAP based upon using the amplitude of low frequency components of the signal. Therefore, the fiberoptic sensor is optionally used not only to provide a MAP datastream but also to detect the mechanical event M that defines the E-M interval in time. If the sensor were placed over a large artery near the heart such as the carotid artery or ascending aorta, duration of the vibrating signal is used to measure the ejection interval, EI. Now the fiberoptic device gives us information on MAP and the event M in the (E-M) interval. In that case, the only component required to create the non-invasive hemodynamic state vectors to provide the cardiac parameters which are responsive to medicines is an EKG. In another aspect, the present invention provides a cardiac parameters monitoring system including a fiberoptic sensor and an EKG. This monitoring package is so lightweight that it is worn, so inexpensive that it is disposable, and so mechanically sturdy that it is used in the trenches of the emergency room or the battlefield.

In another aspect, the present invention provides a method or system for graphically summarizing an entire anesthetic by plotting the trajectory of the non-invasive hemodynamic state vector at regular time intervals. Alternatively, the trajectory is continuously for record-keeping purposes and review. Using a three-dimensional graph whose axes are non-invasive analogues of P, A, and C in the x, y, and z axes, the entire course of an anesthetic or an intensive care unit episode, can be reviewed and understood at one glance. Preferably, the method of graphically showing and overlaying heartrate information along the non-invasive hemodynamic trajectory is used. For example, each data point further includes heart rate representation in color along a continuous spectrum from red to blue, wherein blue denotes low heartrates, while red denotes high heart rates.

In another aspect, the present invention provides a method or system for creating a non-invasively derived record of the anesthetic management, an intensive care unit stay, or outpatient cardiovascular disease management interval. In the event of an untoward event or bad outcome, a reviewer is empowered to go back and identify the time evolution of specific efficient component causes of said untoward event or bad outcome, since the reviewer is now armed with specific time dependent measures of (HR, P, A, C) for improving patient safety and quality of care by allowing for more precise diagnosis than the present state of the art.

In addition to providing useful parametric information on myocardial function based only on non-invasive measurements from the patients who require acute medical care, all of the above systems are also applicable to the cardiovascular fitness industry, the life insurance industry, and the health maintenance organization (HMO) industry to monitor their patients' or clients' wellness. For example, using the non-invasive method described here, it is possible to determine the percentage increase in cardiac output that occurs, relative to baseline when at rest, following a prescribed, standardized amount of physical work, such as dictated by the Bruce Protocol, for a patient on a treadmill. Such information, obtained easily and at virtually zero risk to the patient, may have useful predictive value as an index of cardiac reserve, in predicting mortality following major surgery, or in predicting mortality due to cardiovascular illness. In particular, a higher percentage increase in cardiac output resulting from a given amount of exercise is a higher index of aerobic cardiac fitness. It could be used by the insurance industry to adjust their life insurance premiums on an individual basis, without requiring all clients to undergo cardiac catheterization. Likewise, it could be used by fitness enthusiasts to quantify their progress in the gym, and by the less enthusiastic, to exercise only exactly as much and as often, as is absolutely necessary. To further confirm and verify the robustness of the correlations illustrated above, experiments were conducted on two subjects. The procedure and results of those experiments are discussed below.

Experimentation

Experiments were performed on two female pigs (Pig 1 and Pig 2) on separate occasions. The pigs were given general anesthesia with Isoflurane, Oxygen and Fentanyl. They were intubated and mechanically ventilated. The pigs were monitored using an EKG, a femoral arterial line, and a Swan-Ganz Thermodilution Pulmonary Arterial Catheter. A capnograph was used to measure end-tidal carbon dioxide. An esophageal thermistor was used to measure body temperature. A pulse oximeter was used to measure oxygen saturation. In addition, a catheter was placed over a needle, through the anterior chest wall, into the Left Ventricle. Fluoroscopic guidance was used to place the catheter. Intravenous contrast and pressure readings were used to confirm the presence of the catheter tip in the Left Ventricle.

Three vasoactive agents were used to create a broad range of possible hemodynamic states. They are dobutamine, to increase Contractility, nitroglycerine to reduce Preload and Afterload, and phenylephrine to increase Afterload. One agent was infused at a time by a calibrated infusion pump at varying rates. At each infusion rate, the system was allowed to come to equilibrium, and a hemodynamic steady state was created. In the first pig experiment, 18 different hemodymanic states were created with Pig 1. In the second pig experiment, 15 hemodynamic steady states were created with Pig 2. Once steady state was achieved, the ventilator was turned off to eliminate respiratory variation. At each steady state, the data was digitized and recorded on a laptop floppy disk. For Pig 1, data was averaged over 60 seconds. For pig 2, data was averaged over 30 seconds. At each hemodynamic steady state and over each data acquisition interval, the waveforms were averaged to create an "average" waveform that represented the data over the acquisition interval. Each waveform was arbitrarily synchronized to begin with the S-wave on the EKG. At the conclusion of the data acquisition interval, 5 separate thermodilution cardiac outputs were measured using 10 cc of saline at room temperature. These were averaged to get an average cardiac output, in liters/minute. The protocol for drug infusion rates is shown in the following table.

Drug Infusion Protocol

| Experiment # | Drug | Concentration | Rate, cc/hr |
|---|---|---|---|
| Pig #1 | | | |
| 1 | No drug infusion | | |
| 2 | Dobutamine | 1000 micrograms/cc | 5 |
| 3 | Dobutamine | 1000 micrograms/cc | 10 |
| 4 | Dobutamine | 1000 micrograms/cc | 15 |
| 5 | Dobutamine | 1000 micrograms/cc | 10 |
| 6 | Dobutamine | 1000 micrograms/cc | 20 |
| 7 | Dobutamine | 1000 micrograms/cc | 30 |
| 8 | No drug infusion | | |
| 9 | Nitroglycerine | 200 micrograms/cc | 3 |
| 10 | Nitroglycerine | 200 micrograms/cc | 10 |
| 11 | Nitroglycerine | 200 micrograms/cc | 100 |
| 12 | Nitroglycerine | 200 micrograms/cc | 200 |
| 13 | Nitroglycerine | 200 micrograms/cc | 500 |
| 14 | No drug infusion | | |
| 15 | Phenylephrine | 40 micrograms/cc | 20 |
| 16 | Phenylephrine | 40 micrograms/cc | 40 |
| 17 | Phenylephrine | 40 micrograms/cc | 80 |
| 18 | Phenylephrine | 40 micrograms/cc | 120 |

-continued

| Experiment # | Drug | Concentration | Rate, cc/hr |
|---|---|---|---|
| Pig #2 | | | |
| 1 | No drug infusion | | |
| 2 | No drug infusion. | Pig given 1 liter of crystalloid for hydration. | |
| 3 | Phenylephrine | 40 micrograms/cc | 20 |
| 4 | Phenylephrine | 40 micrograms/cc | 60 |
| 5 | Phenylephrine | 40 micrograms/cc | 90 |
| 6 | Phenylephrine | 40 micrograms/cc | 200 |
| 7 | Phenylephrine | 40 micrograms/cc | 300 |
| 8 | No drug infusion | | |
| 9 | Dobutamine | 1000 micrograms/cc | 5 |
| 10 | Dobutamine | 1000 micrograms/cc | 10 |
| 11 | Dobutamine | 1000 micrograms/cc | 15 |
| 12 | Dobutamine | 1000 micrograms/cc | 20 |
| 13 | Dobutamine | 1000 micrograms/cc | 30 |
| 14 | No drug infusion | | |
| 15 | Nitroglycerine | 200 micrograms/cc | 50 |
| 16 | | | |

To create the invasive hemodynamic state vectors, the following approach was used. Using the averaged waveforms, LVEDP was obtained by inspection of the LVP(t) waveform to look for the value of LVEDP just prior to the rapid increase in LVP due to systole. Contractility was obtained by differentiating the LVP(t) curve with respect to time and recording the maximum value of the first derivative during systolic ejection, dP/dtmax. Afterload that is approximated by Systemic Vascular Resistance (SVR) was obtained by the usual formula (see Kaplan, J. A., M.D., Cardiac Anesthesia, Philadelphia, W.B. Saunders Company, 1993, p. 63)

$$SVR = \frac{(MAP - CVP) * 80}{CO} \quad \text{Eq. 22}$$

where MAP is the Mean Arterial Pressure in mmHg, and CVP is the Central Venous Pressure in mmHg. CO is the cardiac output in liters/minute. The above constant having a value of 80 is used to convert mmHg/(liter/min) into dyne*sec*cm$^{-5}$. CVP was recorded by hand from the monitor at each steady state as was MAP. The heart rate (HR) per minute was obtained by measuring the period of the averaged EKG, taking its reciprocal, and then multiplying by 60 sec/min. The HR was divided into the CO to get the Stroke Volume (SV). Based upon the above parameters, the invasive hemodynamic state vectors were derived.

To create the non-invasive hemodynamic state vectors, the following approach was used. To measure the Ejection Interval, the LVP and Arterial Blood Pressures (ABP, or A(t)) were graphed simultaneously. The ABP trace was moved backwards in time until the LVP equaled the Diastolic ABP. This moment in time marked the opening of the aortic valve. The curves were followed until they intersected again. The latter point marked the closure of the aortic valve. The Ejection Interval, EI is just the time from opening to closure of the aortic valve. MAP was simply read from the monitor display. Alternatively, the ABP waveform was integrated over the cardiac period, and then the integral was divided by the period to get MAP. It did not make a significant difference which approach was used. As indicated previously, EI is easily obtained with an acoustic Doppler device placed in the suprastemal notch over the ascending aorta. MAP is also easily obtained by a blood pressure cuff optionally with a DINAMAP, which is a well known blood pressure measuring device. The above devices are ubiquitous and relatively inexpensive.

The E-M interval (more specifically Q-A interval) was measured in two ways. In the first pig experiment, the interval between the Q-wave on EKG and the upstroke of the ABP was measured. In the second pig, the Q-A interval measurement was not possible due to noise in the diastolic baseline arterial pressure trace. To compensate for the inability to define 'A' of the Q-A interval, the curve of ABP was smoothed and differentiated twice. In the differentiated curve, the moment of maximum upward acceleration in ABP, A"max, clearly rose above the noise. When the same method was used on the data from the first pig, the linear transformation worked as well or better. While it can be argued that the use of an indwelling arterial catheter is not 'non-invasive', several inexpensive and non-invasive methods to define the 'M' event at the end of the E-M interval exist.

Incidentally, data processing and graphing were done using Microcal ORIGIN. (see Origin, Data Analysis and Technical Graphics, Microcal Software Inc., One Roundhouse Plaza, Northampton, Mass., 01060).

In a first embodiment of the present invention, LVEDP, SVR and dP/dtmax are correlated to the non-invasively measured results according to the above Eqs. 8, 9 and 10. The processing results or conclusions based on the above correlations are described below. There are close correlations between the invasively measured parameters and the non-invasively derived parameters based upon the above described correlation methods according to the present invention.

Figure 5:
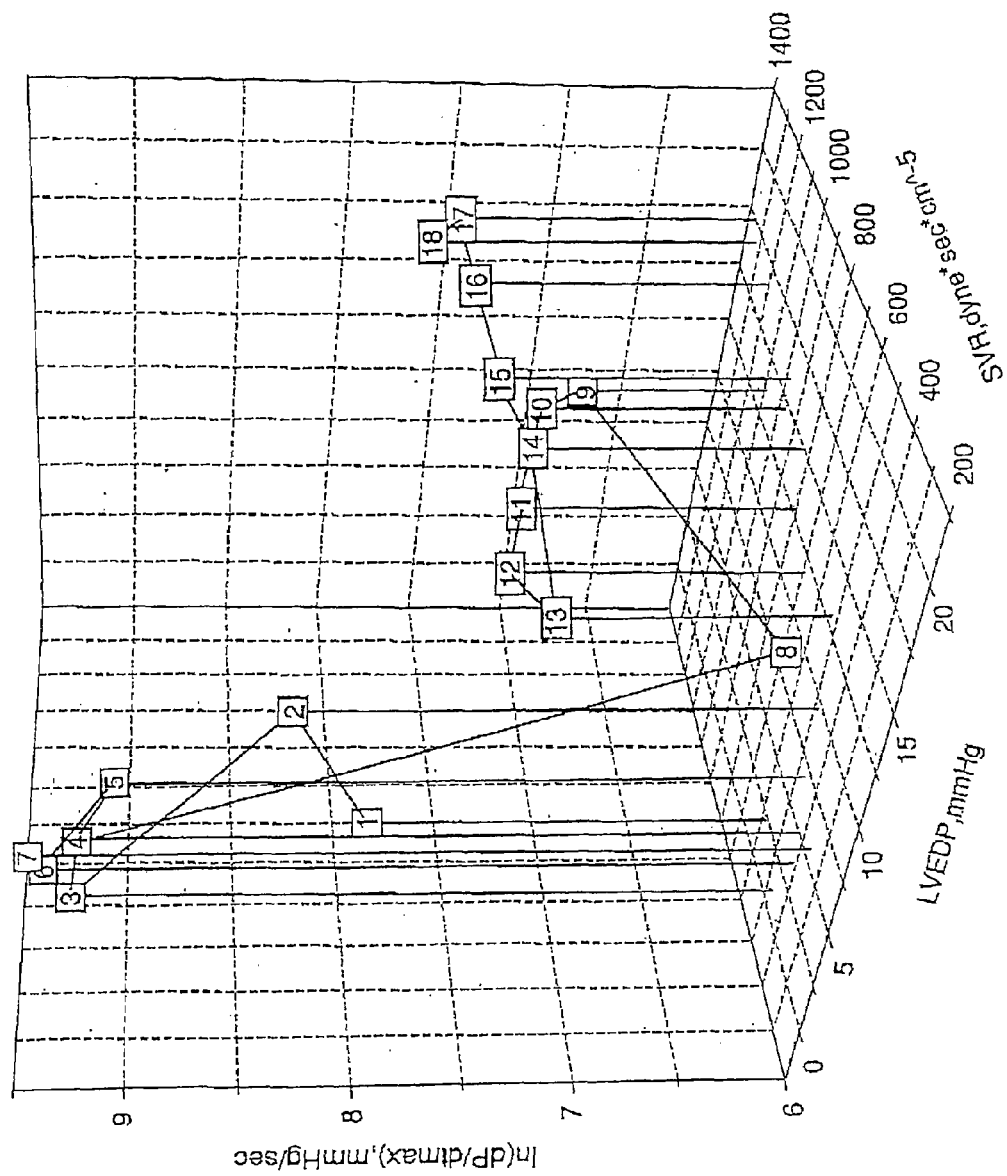
FIG. 5 is a graph illustrating an invasive hemodynamic vector space for a first subject according to the first embodiment of the present invention.
Figure 6:
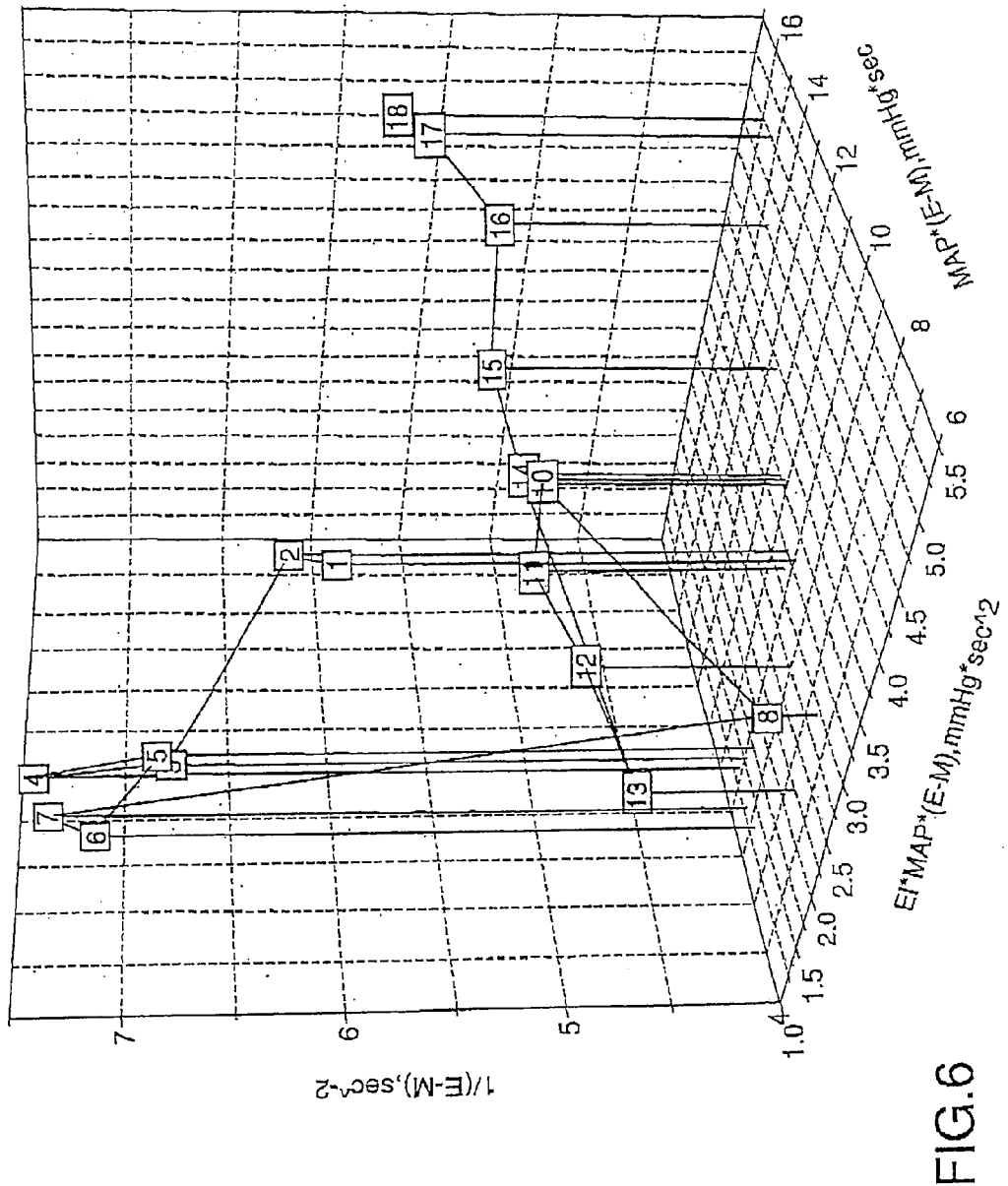
FIG. 6 is a graph illustrating a non-invasive hemodynamic vector space for the first subject according to the first embodiment of the present invention.

FIG. 5 shows the results measured by the above described invasive method for Pig 1 while FIG. 6 shows the results derived from the results measured by the above described non-invasive method for Pig 1. FIG. 5 shows the Invasive Hemodynamic Vector Space, H' (LVEDP, SVR, dP/dtmax) in pig 1. FIG. 6 shows the same 18 hemodynamic steady states in the Non-Invasive Hemodynamic Vector space, N. The three mutually perpendicular axes of N are given as [EI*MAP*(Q-A"max), MAP*(Q-A"max), 1/Q-A"max)] and, mapped to [x, y, z]. With Pig 1, there is real homology between the trajectory of the vector from the origin to the point in space that denotes each hemodynamic state in both alternative sets of axes. From experiments 1 through 7, Contractility increases while LVEDP tends to decrease with increasing infusions of dobutamine. A 'crash' occurs between experiments 7 and 8 when the dobutamine is turned off after very fast infusions. Both the LVEDP and the SVR decrease between experiments 9 through 13 as the nitroglycerine infusion is increased. The SVR and LVEDP steadily increase as the phenylephrine infusion is increased among the baseline experiment 14 to experiment 18. Interestingly, Contractility varies only a little between experiments 9 through 18. No dobutamine was infused between experiments 9 and 18. All of these events are mirrored from the Invasive Vector Space H' to the Non-invasive Vector Space N. Empirically, one sees a 'one-to-one' mathematical mapping between the two vector spaces as described in Eqs. 4 through 11.

Figure 7:
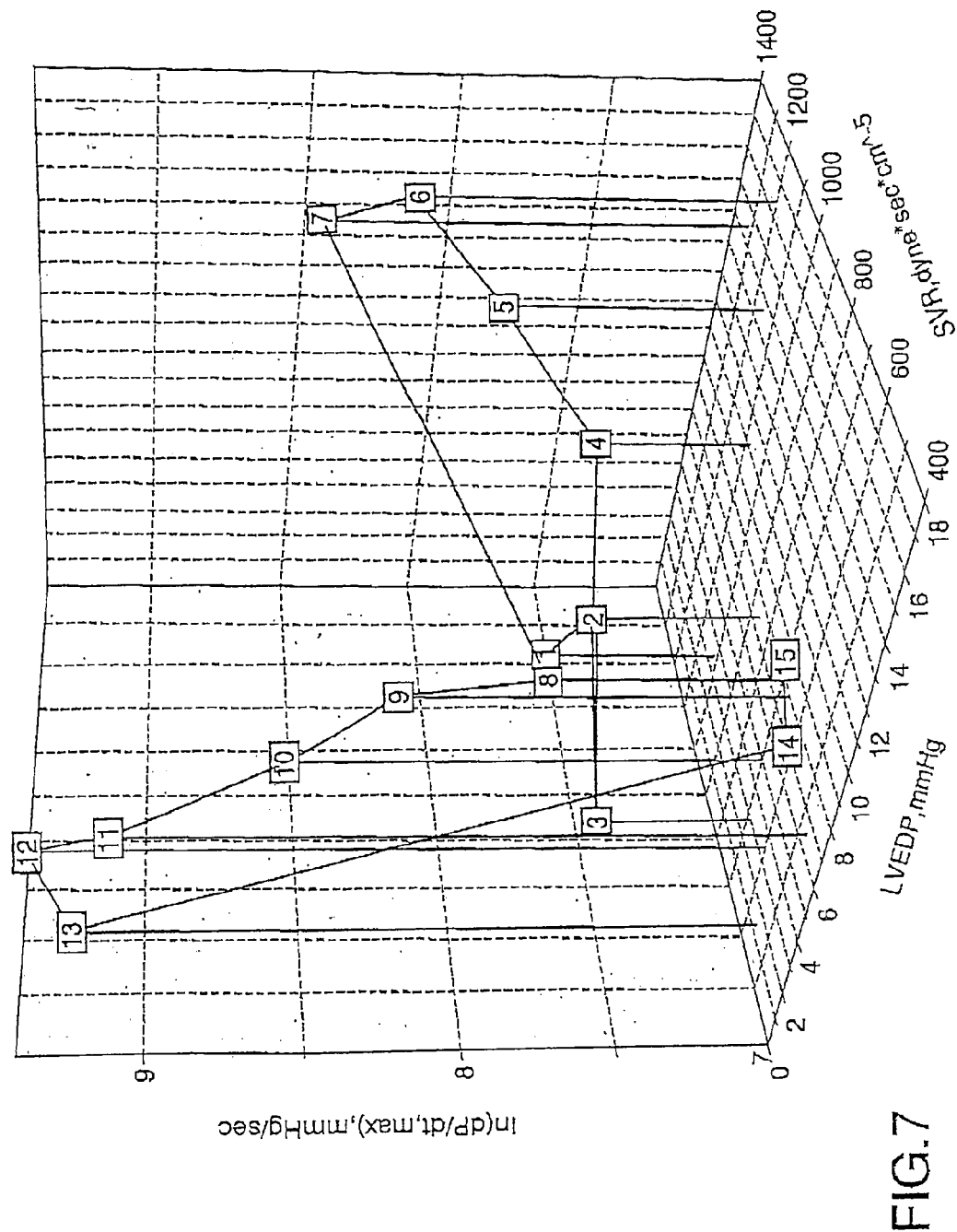
FIG. 7 is a graph illustrating an invasive hemodynamic vector space for a second subject according to the first embodiment of the present invention.
Figure 8:
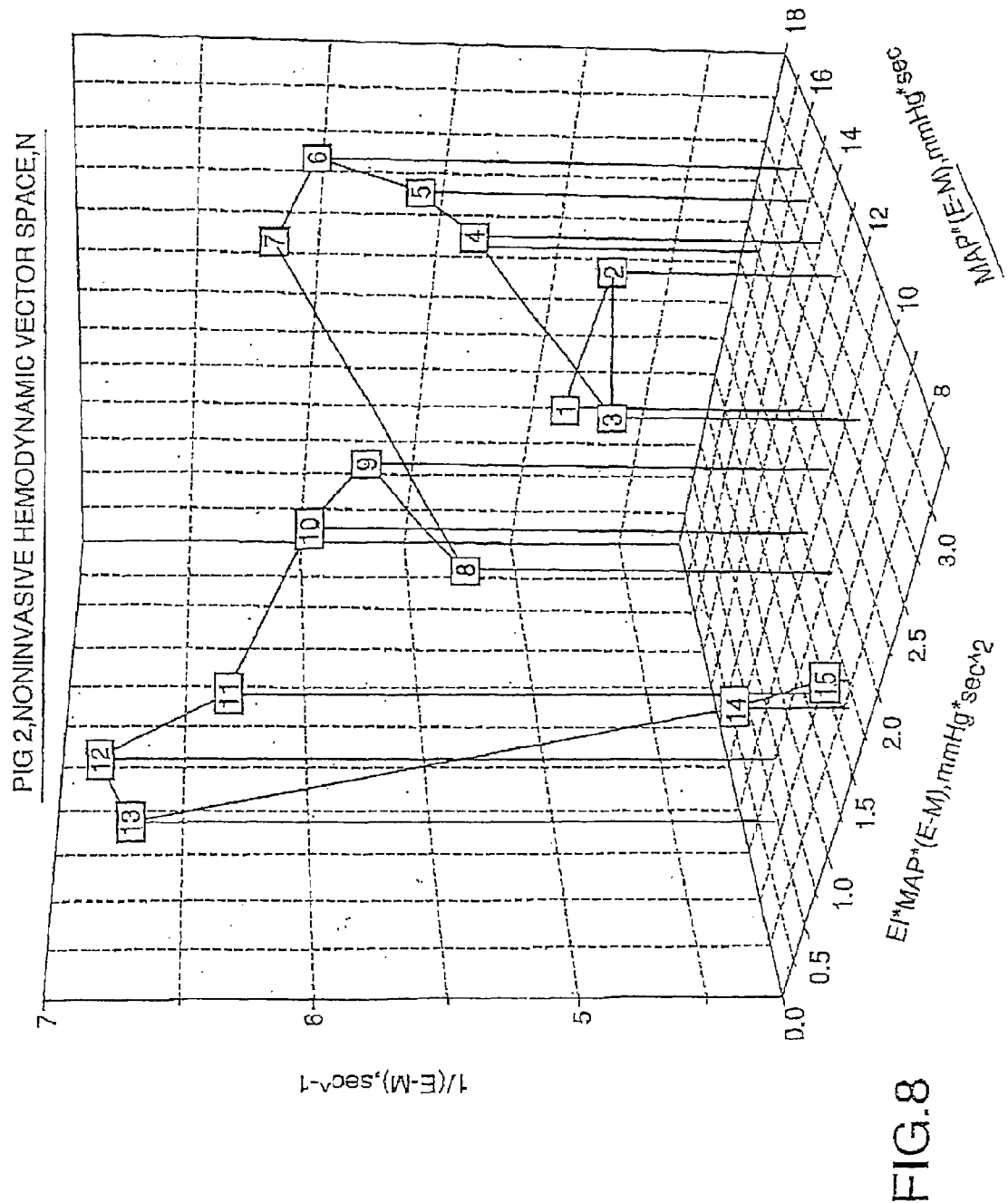
FIG. 8 is a graph illustrating a non-invasive hemodynamic vector space for the second subject according to the first embodiment of the present invention.

FIG. 7 shows the results measured by the above described invasive method above for Pig 2, while FIG. 8 shows the results derived from the results measured by the above described non-invasive method for Pig 2. FIG. 7 shows the Invasive Vector Space, H' in Pig 2. Using the vasoactive drug infusions, Pig 2 is taken on a trajectory through Invasive Hemodynamic Space that stops at fifteen distinct steady states. FIG. 8 shows the same fifteen hemodynamic steady states in the Non-Invasive Hemodynamic Vector space, N.

The three mutually perpendicular axes of N are given as [EI*MAP*(Q-A"max), MAP*(Q-A"max), 1/Q-A"max)], mapped to [x, y, z]. LVEDP increases, and SVR decreases with fluid repletion of one liter of crystalloid between states 1 and 2. Contractility does not budge with fluid administration. The change is mirrored in the Non-invasive Vector Space N. As the phenylephrine infusion is gradually increased between states 4 and 7, the SVR and LVEDP dramatically increase. Contractility modestly increases. From state 7 to 8, the phenylephrine is turned off, and there is a dramatic decrease in LVEDP and SVR. This is also well reflected in N. Now the dobutamine is turned on and gradually increased from states 9 to 13. Contractility significantly increases while LVEDP decreases. This is consistent with the well known functions of dobutamine as a cardiac medicine. (see Gilman, A., Goodman L., The Pharmacological Basis of Therapeutics, Seventh Ed., New York, Macmillan, 1985, p. 163). Between states 13 and 14, there is a crash as the dobutamine is turned off. Contractility rapidly decreases as the dobutamine is metabolized while LVEDP goes up.

During all these hemodynamic states of Pig 2, there is the striking homology between FIGS. 7 and 8. It is as though the hemodynamic state vectors were moving in two parallel universes. One universe is with information obtained with great risk, cost, and considerable pain while the other universe is with information obtained with no risk, low cost, and painlessly.

Figure 9:
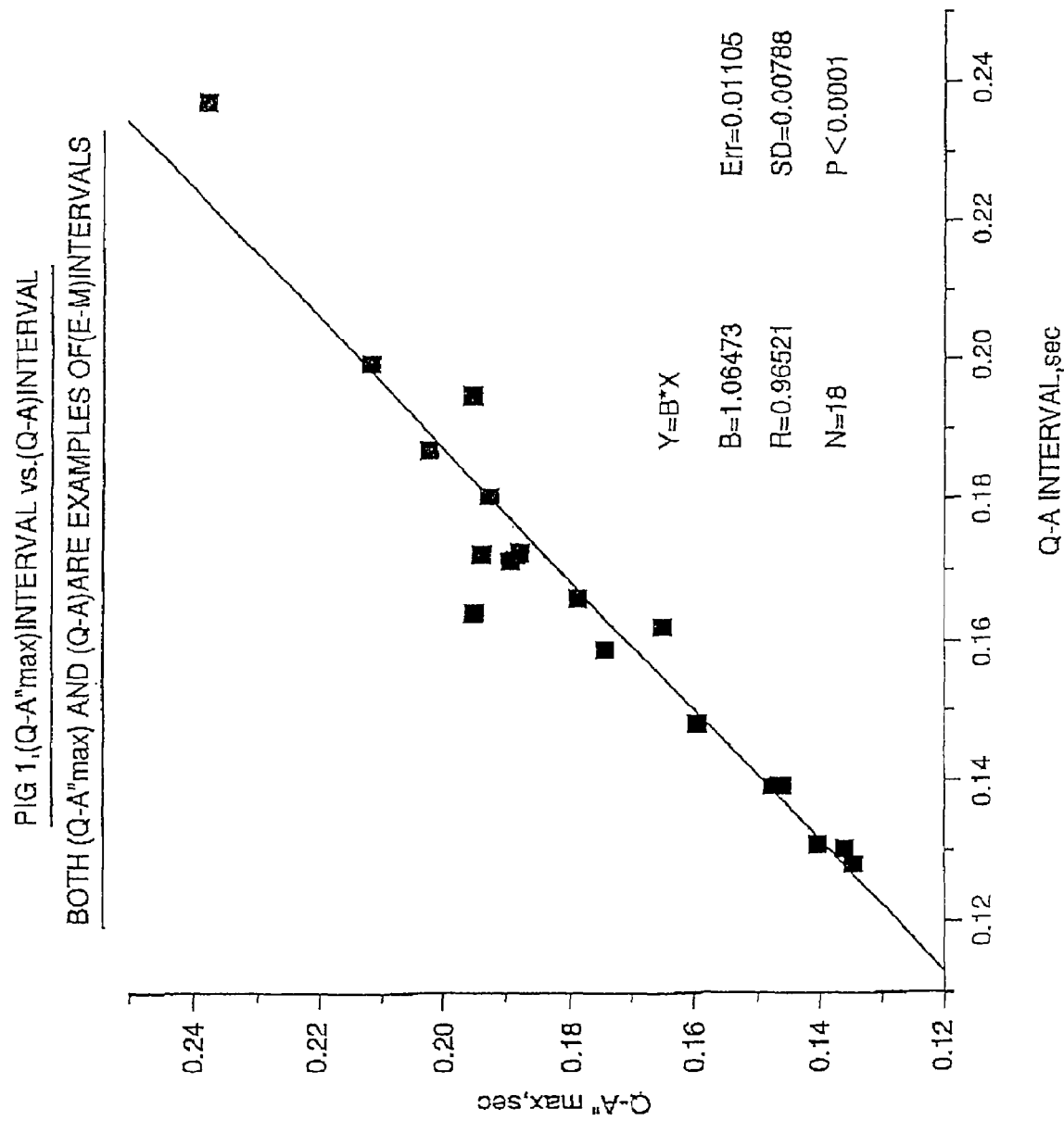
FIG. 9 is a graph illustrating (Q-A"max) Interval vs. (Q-A) Interval for the first subject according to the first embodiment of the present invention.

To further demonstrate the validity of the correlations that are derived by the preferred method of the present invention, the correlations are verified in the following figures and discussions. FIG. 9 represents the (Q-wave) to (femoral arterial pressure wave, upward acceleration maximum) interval or (Q-A"max) as a function of (Q-A), the interval between the Q-wave on EKG and the time of the femoral arterial pressure wave upstroke. A"max occurs at the maximum value of the second derivative of pressure with respect to time. Both the arterial upstroke and the instant of maximal upward pressure acceleration occur after the onset of systole. A"max always occurs after A since the pressure wave must bottom out before it maximally accelerates. Inspection of FIG. 9 shows that (Q-A"max) is greater than (Q-A) by a factor of 1.065 with an error of 1%. The correlation coefficient between these two measures of Contractility is 0.965. The above correlation strongly indicates that the two intervals (Q-A) and (Q-A"max) are just different species of the genus (E-M) and moreover that they are practically interchangeable. (Q-A) was described in the Lancet in 1974. (Q-A"max) has the advantage that it is easily and accurately determinable when there is noise in the baseline. Noisy baselines are part of the natural history of operating rooms. Therefore, another aspect of the present invention provides a method to determine the non-invasively measured cardiac parameters using Q-A"max.

Figure 10:
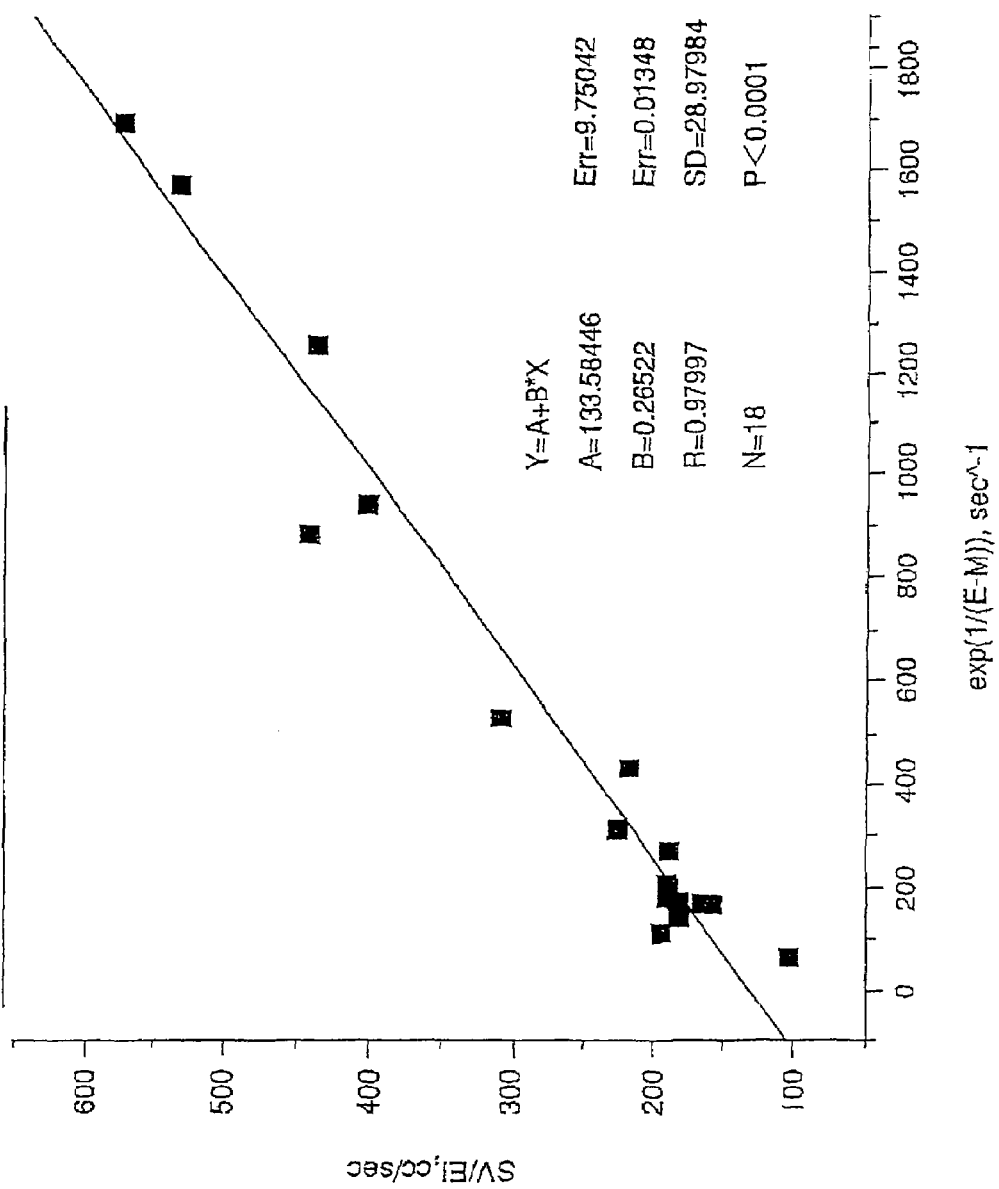
FIG. 10 is a graph illustrating average left ventricular ejection interval outflow rate as a function of the E-M interval for the first subject according to the first embodiment of the present invention.
Figure 11:
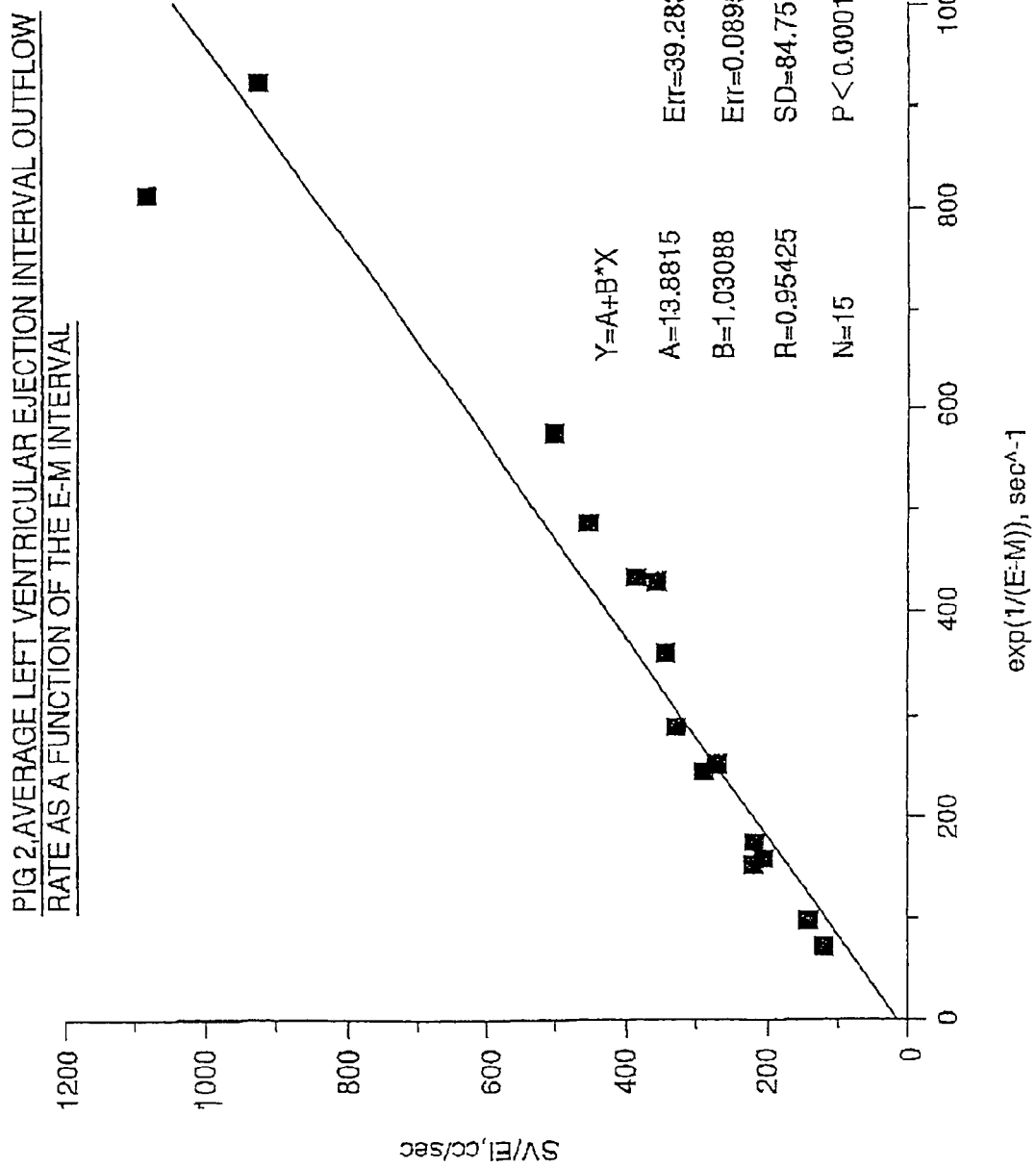
FIG. 11 is a graph illustrating average left ventricular ejection interval outflow rate as a function of the E-M interval for the second subject according to the first embodiment of the present invention.

FIGS. 10 and 11 show the relation between the average rate of left ventricular outflow and the (E-M) interval. In both figures, the (E-M) interval used is the (Q-A"max) interval. The average rate of left ventricular (LV) outflow is just the Stroke Volume (SV) divided by the Ejection Interval (EI) by definition. This yields a quantity, SV/EI, whose units are in cc/sec. FIGS. 10 and 11 respectively describe the above relation for Pig 1 and Pig 2. It is clear that, in both cases, the average systolic ejection outflow rate is linearly proportional to 'e' raised to the power of the reciprocal of the E-M interval. In Pig 1, the linear correlation coefficient is 0.98. In Pig 2, the linear correlation coefficient is 0.95. Therefore, it is another aspect of the present invention to provide a correlation between SV/EI and E-M interval, which equals to Q-A"max.

Figure 12:
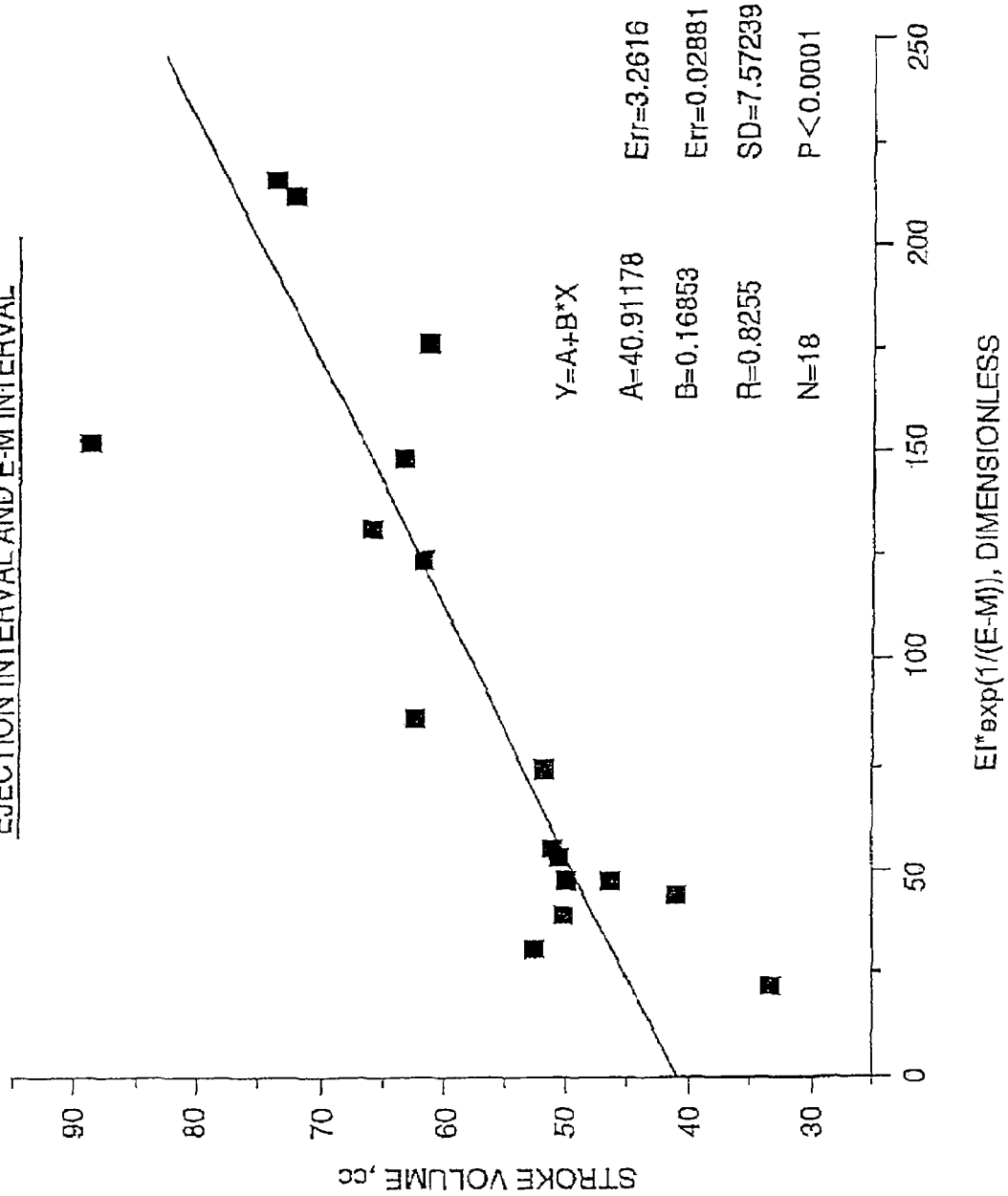
FIG. 12 is a graph illustrating stroke volume as a function of ejection interval and E-M interval for the first subject according to the first embodiment of the present invention.
Figure 13:
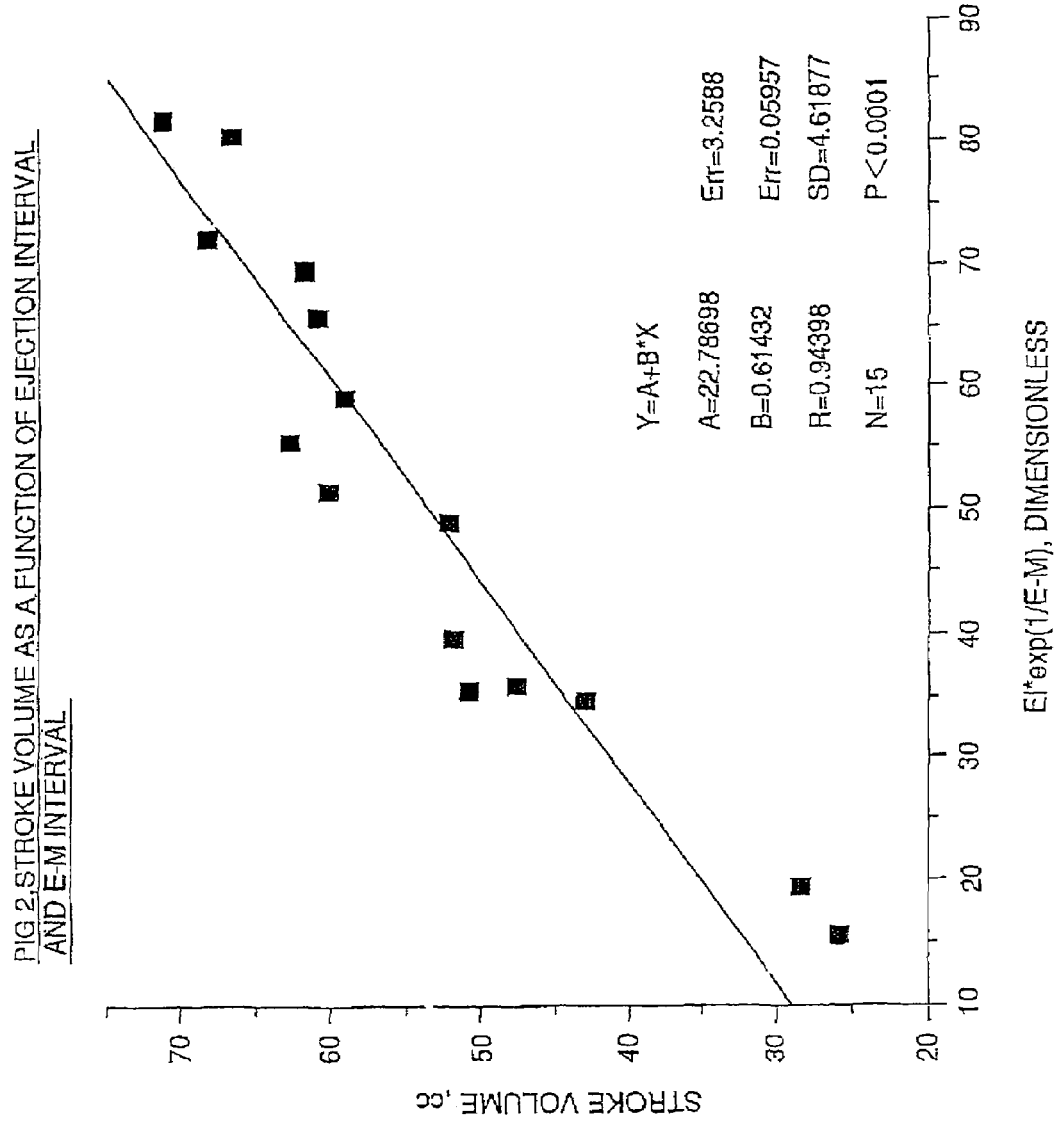
FIG. 13 is a graph illustrating stroke volume as a function of ejection interval and E-M interval for the second subject according to the first embodiment of the present invention.

In FIGS. 12 and 13, the previously described relation is solved for the Stroke Volume (SV). If we can predict the average left ventricular outflow rate, SV/EI on the basis of the (E-M) interval, then multiplying both sides of the equation by EI will give us a quantity which will track in a useful way with SV. FIG. 12 is a plot of Stroke Volume against EI*exp(1/E-M) in Pig 1. FIG. 13 is the same plot of the data from Pig 2. In both plots, the (Q-A"max) interval was used for the (E-M) interval. Pig 1 data yields a linear correlation coefficient of 0.825. Pig 2 data yields a linear correlation coefficient of 0.944. Significantly, the product literature for Hemosonic esophageal Doppler device indicates that its Cardiac Output measurements correlate with thermodilution measurements with a linear correlation coefficient of 0.80. At least one investigator indicated the correlation at 0.90 (see Klein, G., M.D., Emmerich, M., M.D., Clinical Evaluation of Non-invasive Monitoring Aortic Blood Flow, (ABF) by a Transesophageal Echo-Doppler-Device. Anesthesiology 1998; V89 No. 3A: A953, op. cit.). The Hemosonic manual indicates that CO determined by the device is accurate to ±15%.

Correlations between Parameters in One Dimension

In addition to the excellent correlation between the vector of the invasively measured hemodynamic states and the vector of the non-invasively measured hemodynamic states, the correlations between each parameter of invasively measured hemodynamic states and its respective non-invasive counterpart are demonstrated separately in the following discussions.

Figure 14:
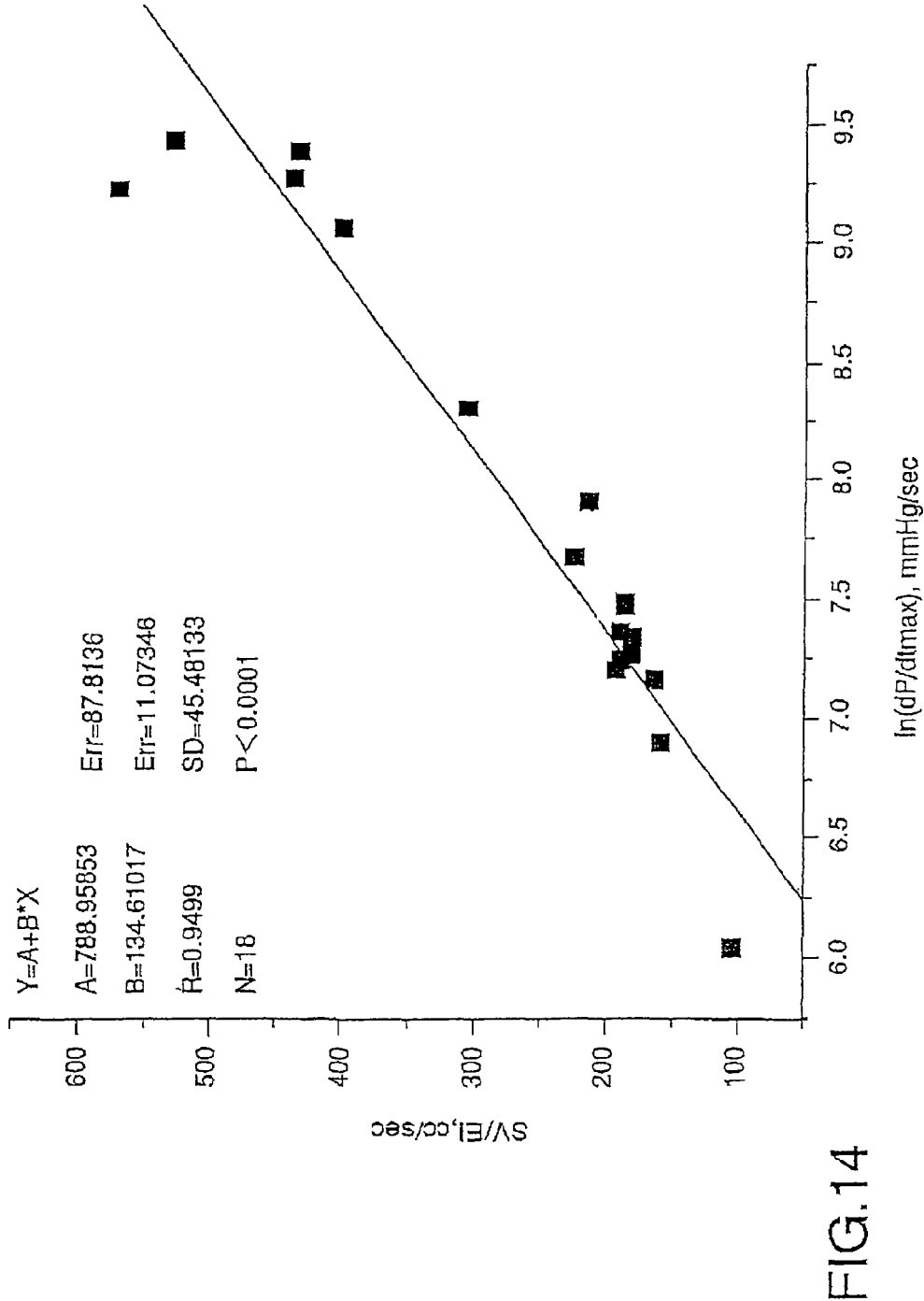
FIG. 14 is a graph illustrating average systolic outflow rate vs. Contractility for the first subject according to the first embodiment of the present invention.
Figure 15:
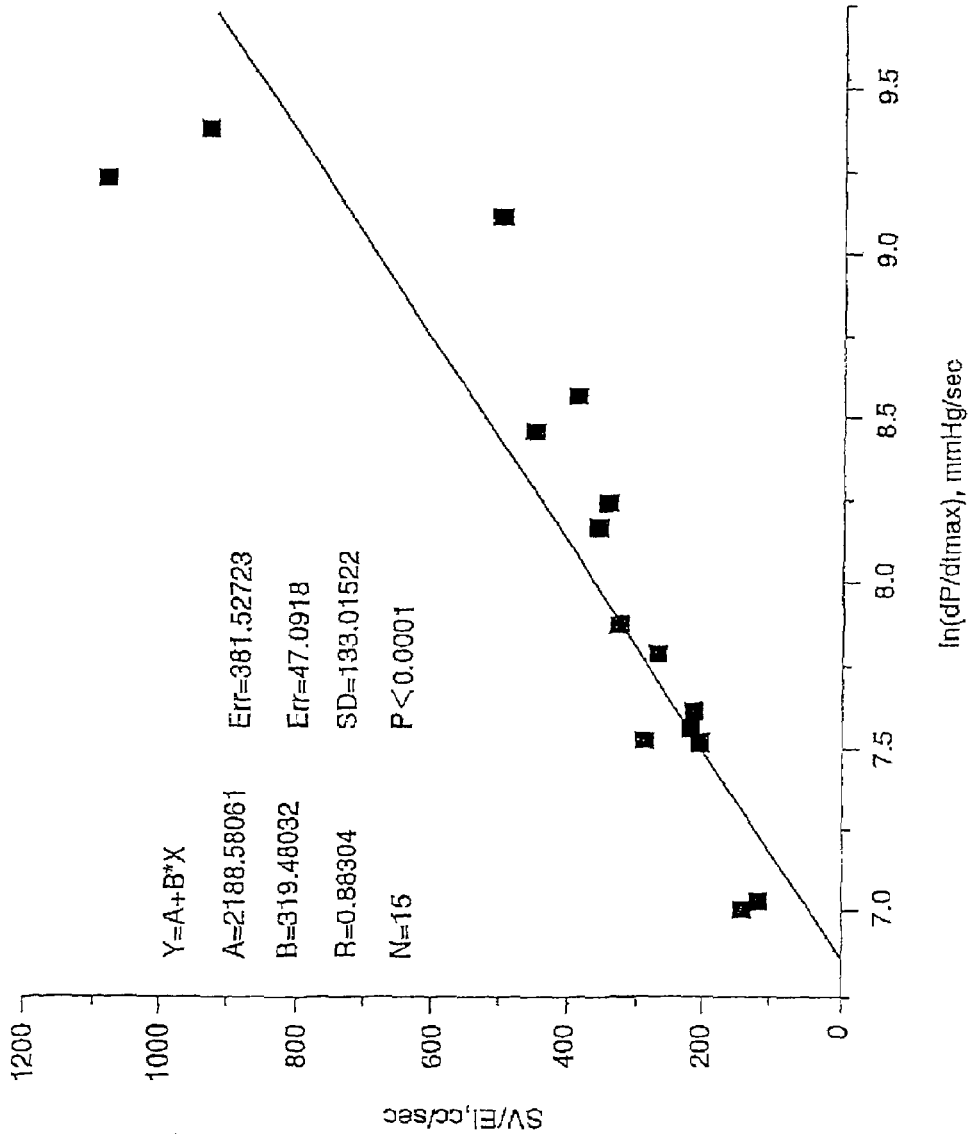
FIG. 15 is a graph illustrating average systolic outflow rate vs. Contractility for the second subject according to the first embodiment of the present invention.

FIG. 14 shows the correlation of the average systolic outflow rate, SV/EI as a function of the natural log of the maximum value of the first derivative of left ventricular pressure with respect to time, ln(dP/dtmax) in Pig 1. This relation shows a linear correlation coefficient, R of 0.9499 and a probability that the relation is due to random chance, (P value) of <0.0001. The same relation is shown for Pig 2 in FIG. 15. The value of R is 0.88304, and P<0.0001. Since SV/EI correlates linearly with exp(1/(E-M)) as shown in FIGS. 10 and 11, exp (1/(E-M)) must correlate linearly with respect to ln (dP/dtmax) as well.

Figure 16:
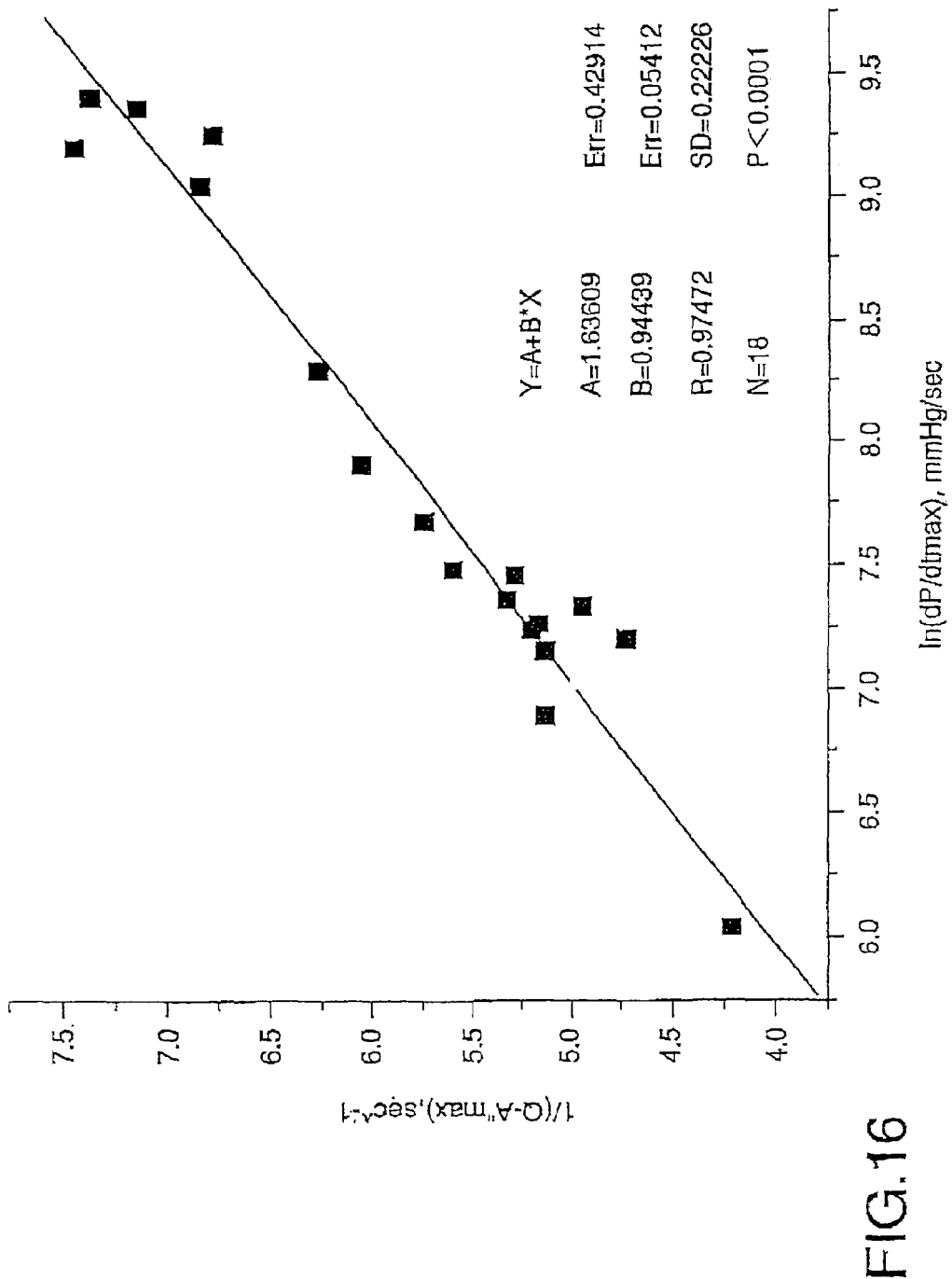
FIG. 16 is a graph illustrating 1/(Q-A"max) the first subject according to the first embodiment of the present invention.
Figure 17:
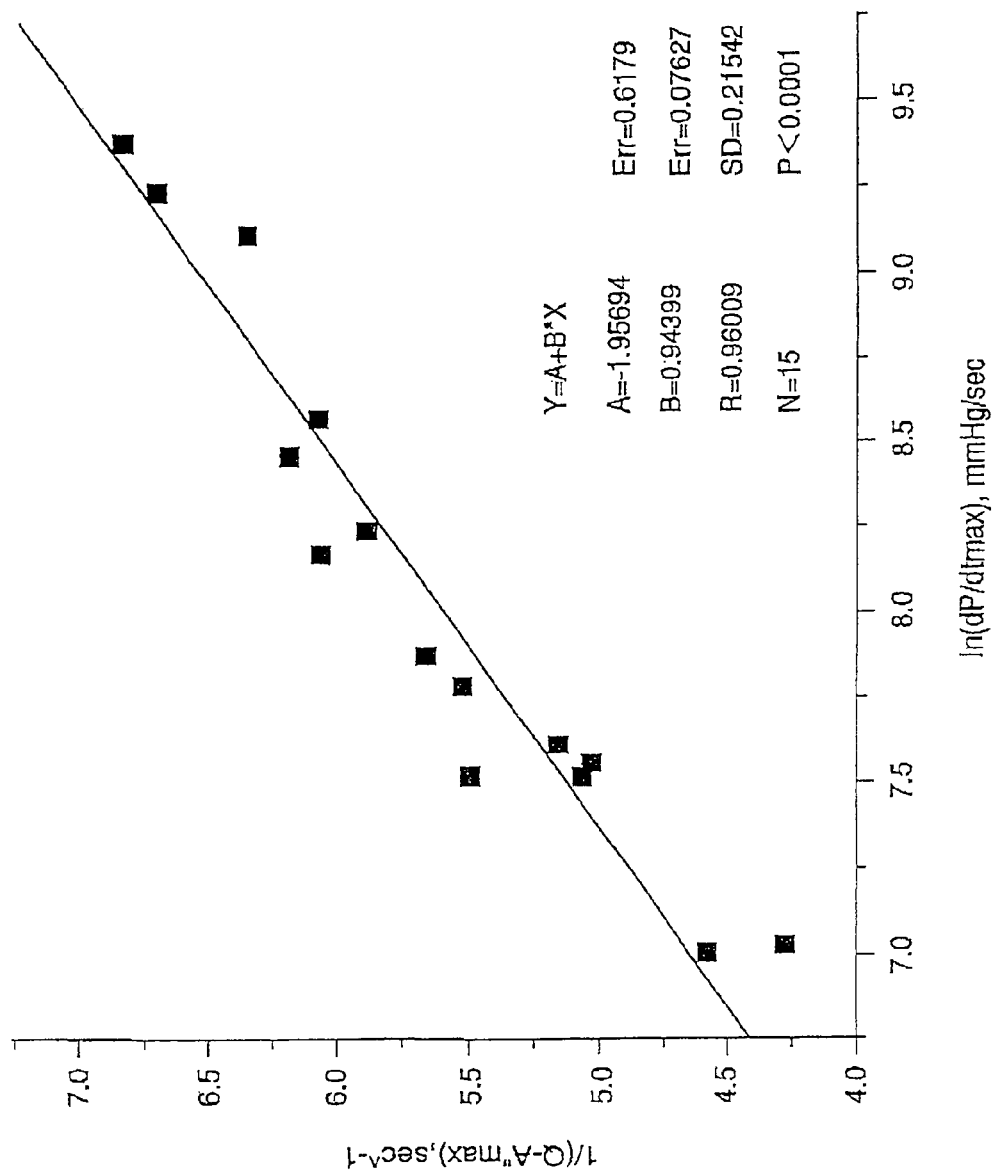
FIG. 17 is a graph illustrating 1/(Q-A"max) the second subject according to the first embodiment of the present invention.

This linear correlation between exp (1/E-M)) and dP/dtmax is further experimentally demonstrated respectively in FIGS. 16 and 17 for Pigs 1 and 2. FIG. 16 illustrates linear relation between 1/(Q-A"max) and ln(dP/dtmax) in the Pig 1 experiments. The linear correlation as shown in FIG. 16 has a correlation coefficient of R=0.97472, and a P value of <0.0001. For Pig 2, R is 0.96009, and P is less than 0.0001 as shown in FIG. 17. These data show, for the first time, the exponential relation between dP/dtmax and 1/(Q-A"max) unlike the relationship between dP/dtmax and Q-A implied by Jackson. (see Jackson, D. M., M.D, A Simple Non-Invasive Technique for Measuring Cardiac Contractility, [Letter]. Lancet 1974; ii: 1457). This exponential relationship between dP/dtmax and 1/(Q-A"max) provides a correlation that is necessary for the method of the present invention of converting the non-invasively measured parameters into the invasively measured parameters that are responsive to medicines.

Jackson spoke of "changes in the Q-A interval" and not in terms of the reciprocal of the Q-A interval, 1/(Q-A). His data are plotted in terms of Δ(Q-A) or the difference in (Q-A) compared to the baseline. 1/(Q-A) is a more physiologically meaningful quantity. The distance L from the aortic valve to the arterial pressure transducer catheter in the femoral artery stays constant throughout the experiment. Then, by definition, the quantity L/(Q-A) is the velocity of electromechanical transduction and propagation of the pulse wave down the arterial tree. We can call L/(Q-A) the Velocity of transduction and propagation or Vtp. Since L is a constant, 1/(Q-A) varies linearly with Vtp. In other words, $$Vtp = L[1/(Q-A)] \quad \text{Eq. 24}$$

So, 1/(Q-A) and by inference (1/(Q-A"max) give us a linear handle on the velocity of electromechanical transduction and elastic wave propagation.

Figure 18:
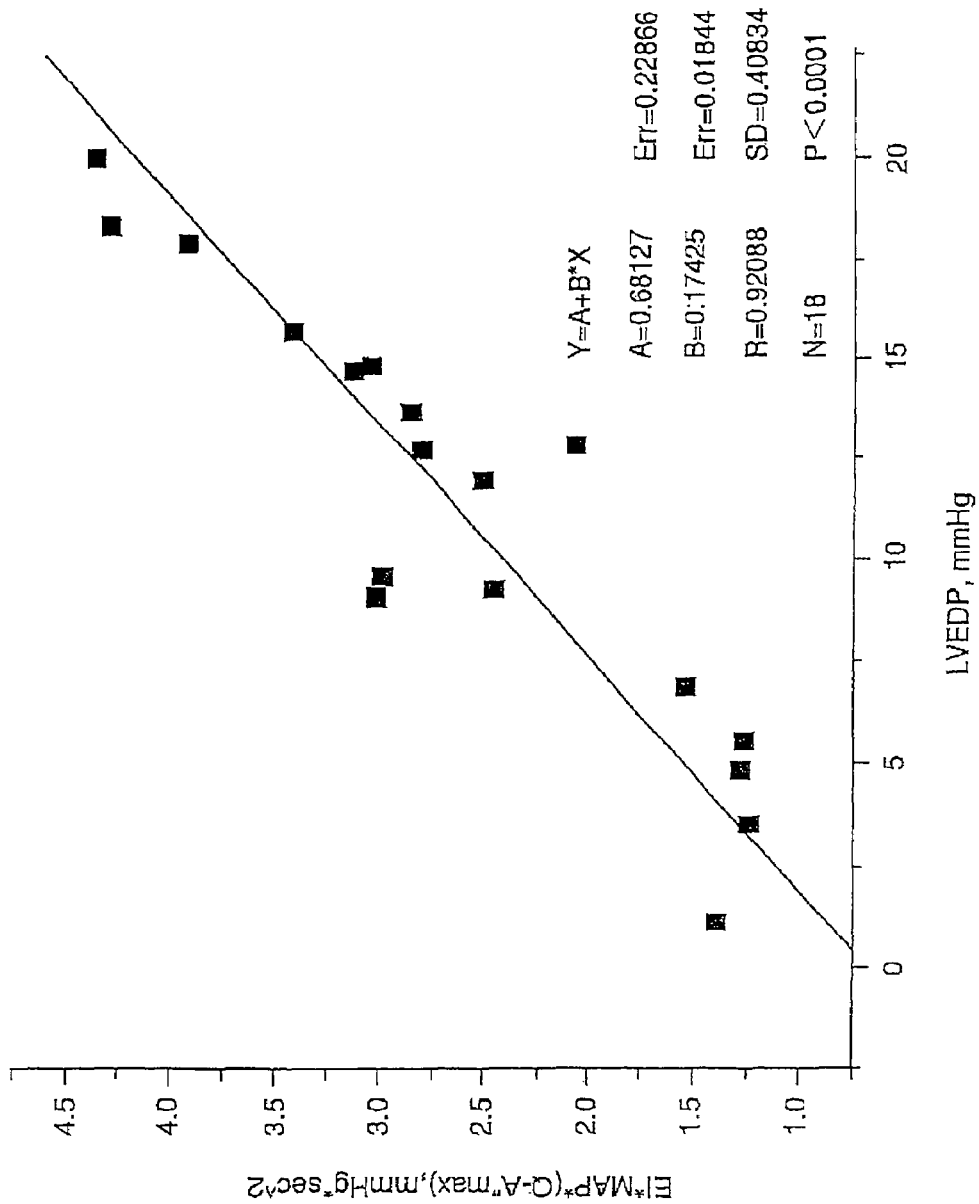
FIG. 18 is a graph illustrating [(Ejection Interval)*(Mean Arterial Pressure)*(Q-A"max)] as a function of left ventricular end-diastolic pressure for the first subject according to the first embodiment of the present invention.
Figure 19:
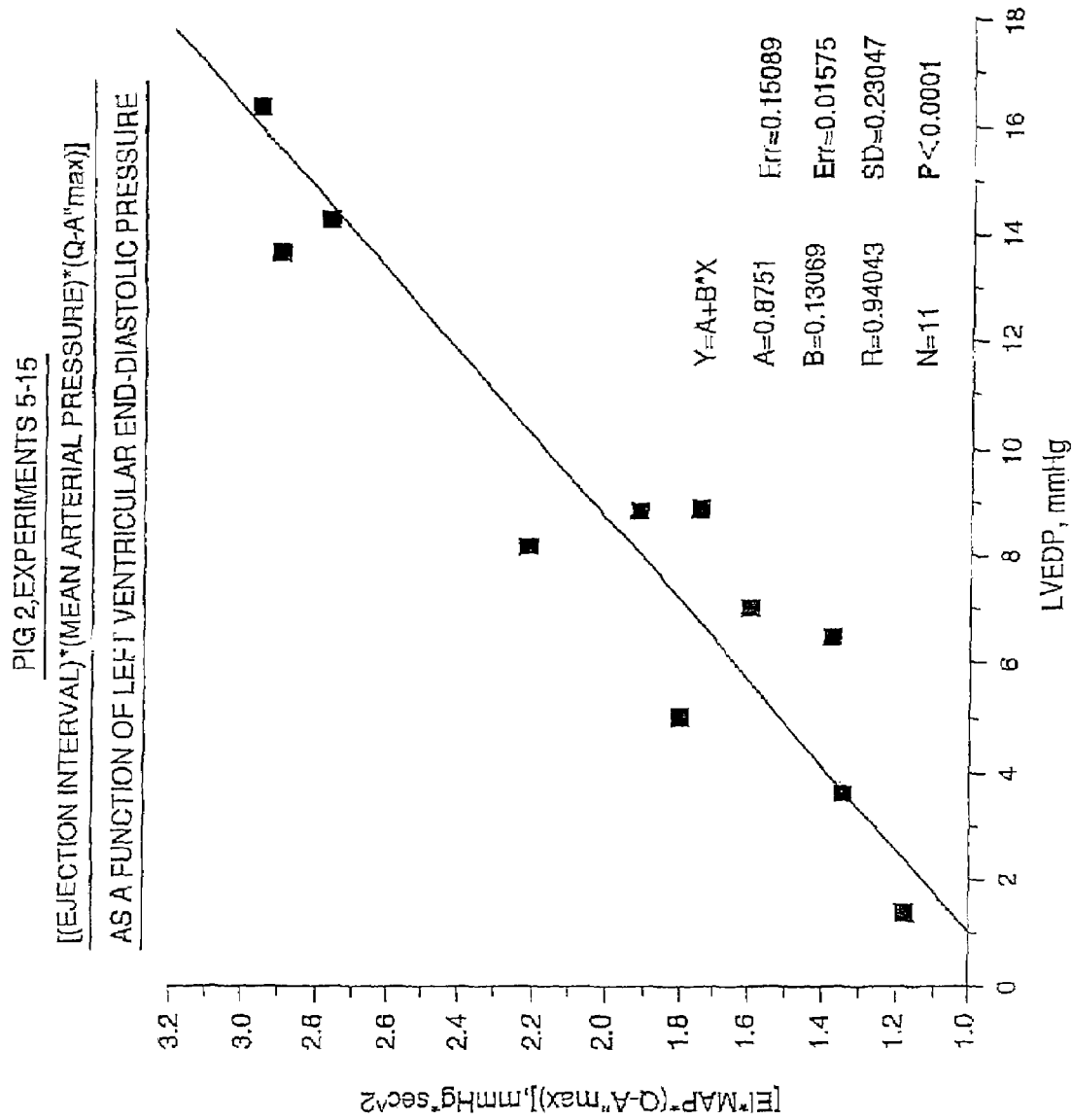
FIG. 19 is a graph illustrating [(Ejection Interval)*(Mean Arterial Pressure)*(Q-A"max)] as a function of left ventricular end-diastolic pressure for the second subject (Experiments 5-15) according to the first embodiment of the present invention.
Figure 20:
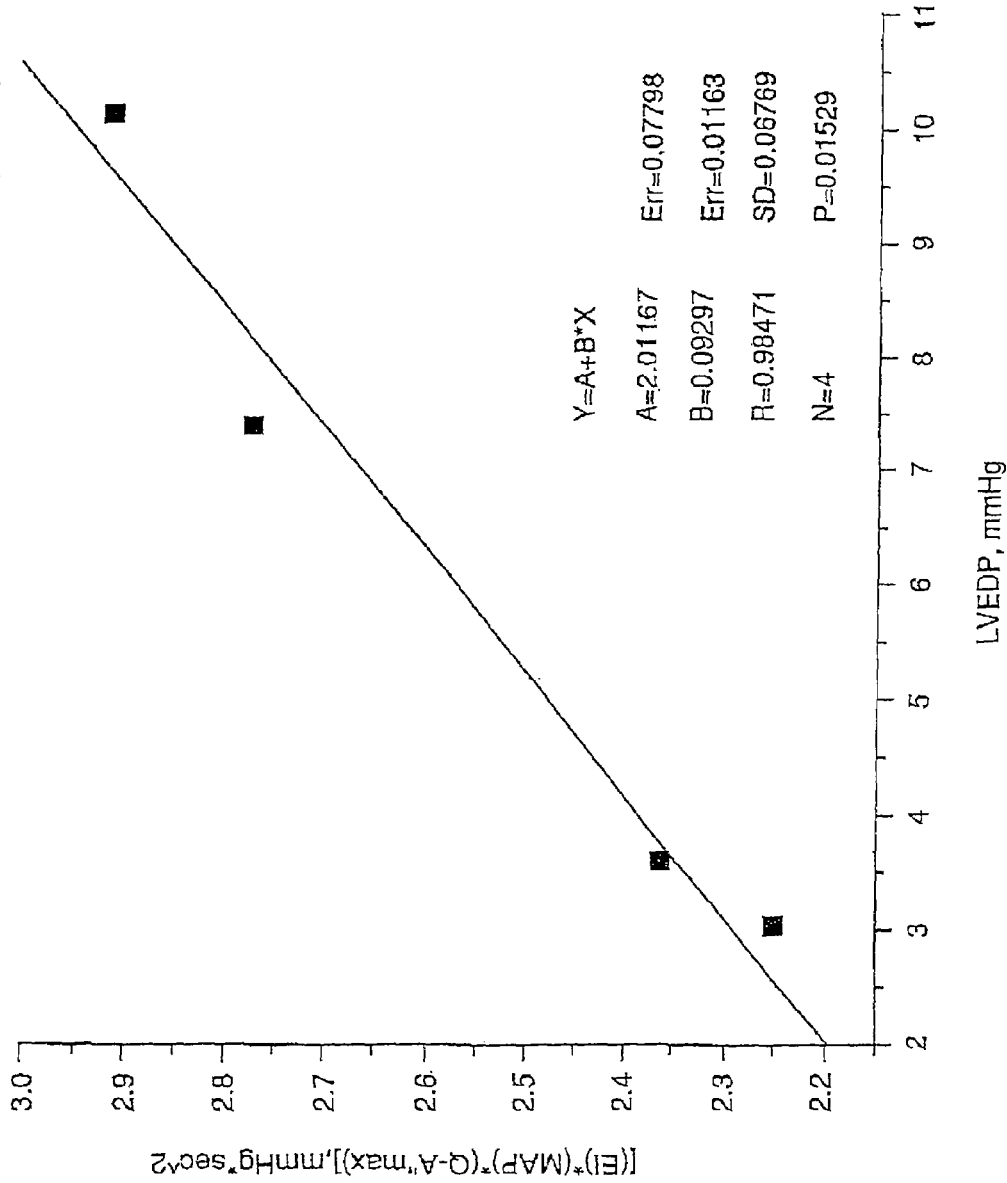
FIG. 20 is a graph illustrating [(Ejection Interval)*(Mean Arterial Pressure)*(Q-A"max)] as a function of left ventricular end-diastolic pressure for the second subject (Experiments 1-4) according to the first embodiment of the present invention.
Figure 21:
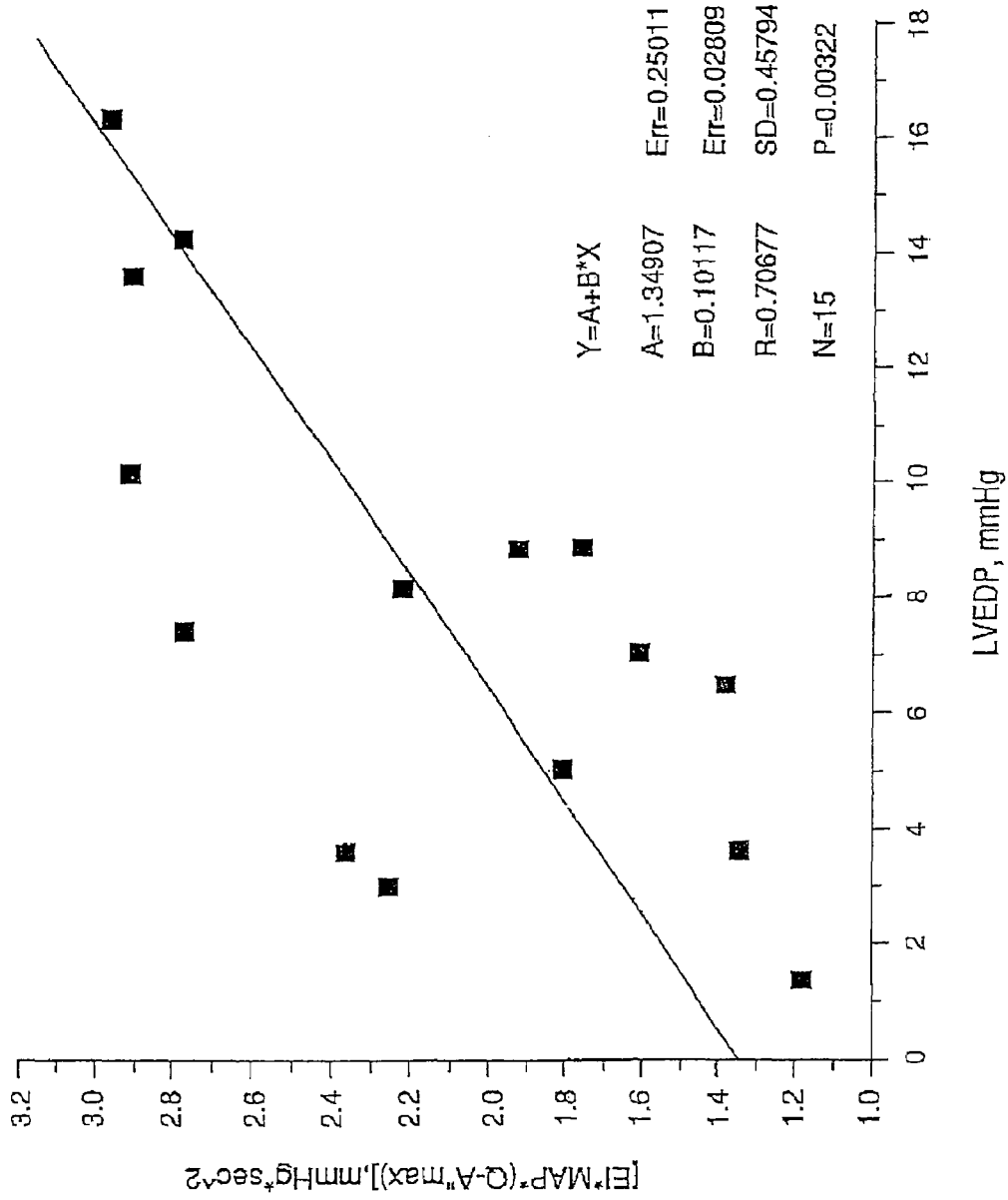
FIG. 21 is a graph illustrating [(Ejection Interval)*(Mean Arterial Pressure)*(Q-A"max)] as a function of left ventricular end-diastolic pressure for the second subject (All Experiments) according to the first embodiment of the present invention.

FIGS. 19, 20, and 21 describe certain experimental data from Pig 2. FIG. 18 shows the relation between LVEDP and (EI*MAP*(Q-A"max)) for Pig 1. The linear correlation coefficient R=0.92088, and P<0.0001 for FIG. 18. FIG. 19 describes certain data in the Pig 2 experiments, but only shows eleven of fifteen points. The points in FIG. 19 represent experiments 5 through 15, which were performed serially in time. For these 11 time-contiguous data points, R=0.94043, and P<0.0001. FIG. 20 shows data for the experiments 1 through 4 of Pig 2. These first four experiments yield R at 0.98471 and P at 0.01529. However, when all fifteen of the data points from Pig 2 are shown together as in FIG. 21, the correlation coefficient falls to 0.7067 with P at 0.0032.

Figure 22:
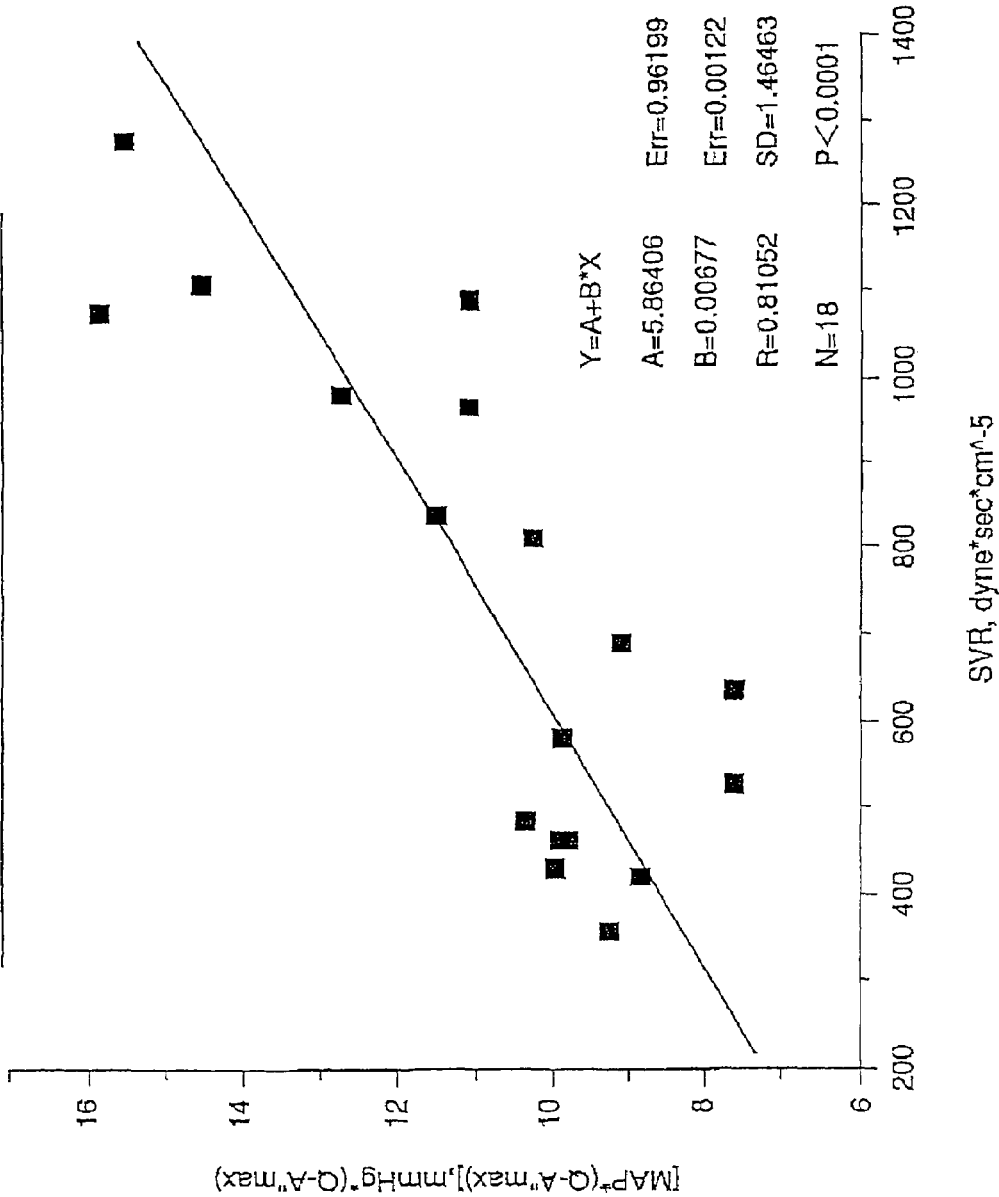
FIG. 22 is a graph illustrating [(Mean Arterial Pressure)*(Q-A"max)] as a function of Systemic Vascular Resistance for the first subject according to the first embodiment of the present invention.
Figure 23:
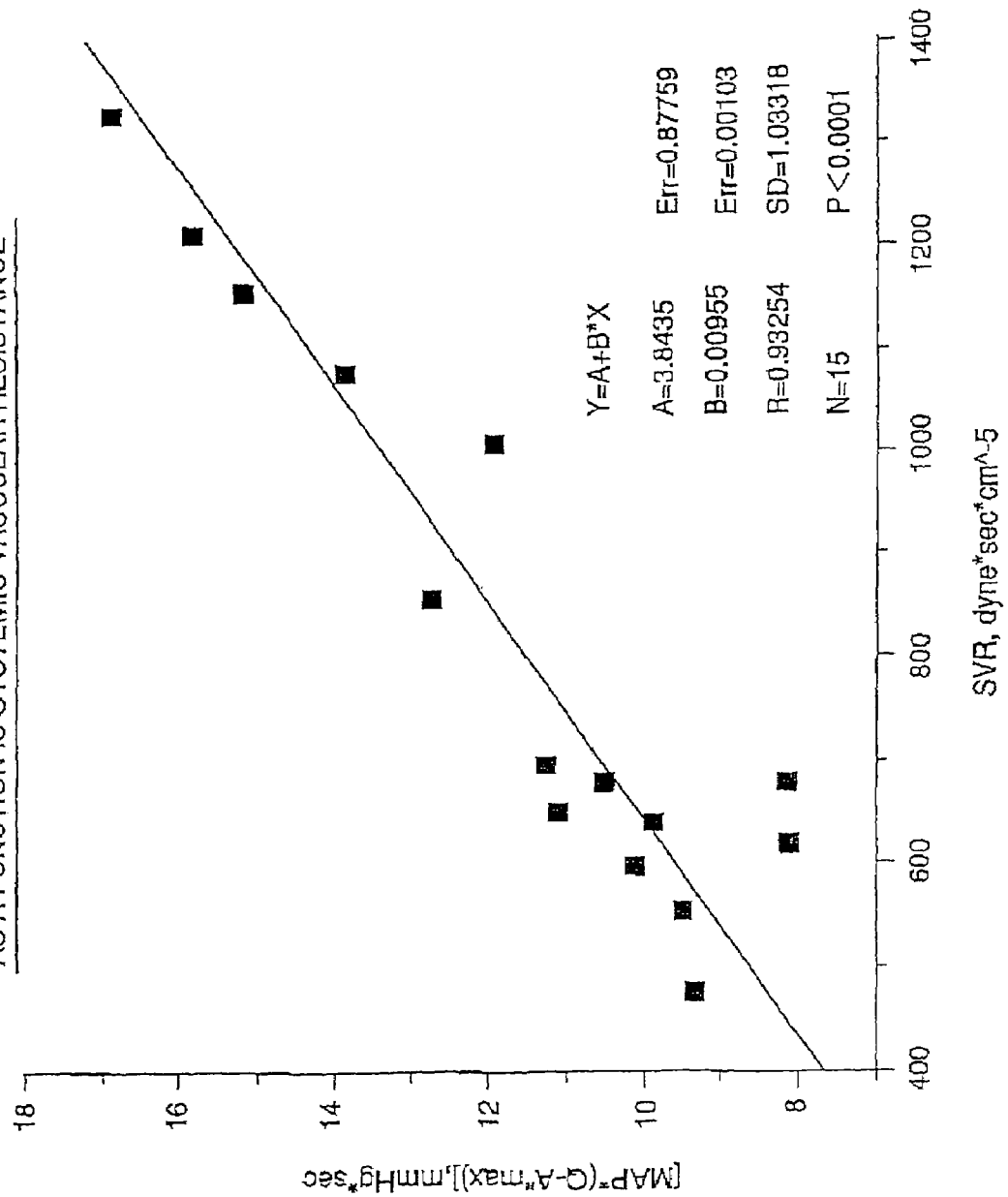
FIG. 23 is a graph illustrating [(Mean Arterial Pressure)*(Q-A"max)] as a function of Systemic Vascular Resistance for the second subject according to the first embodiment of the present invention.

FIGS. 22 and 23 respectively describe experimental data for Pig 1 and Pig 2. FIG. 22 presents the double product [MAP*(Q-A"max)] as a function of the Systemic Vascular Resistance, SVR. In the Pig 1 data, the correlation R=0.81052, and P<0.0001. In the Pig 2 data, R=0.93254, and P<0.0001.

In a second embodiment of the present invention, LVEDP, SVR and dP/dtmax are correlated with the non-invasively measured results according to Eqs. 19, 20 and 21. The correlations have led to the following processing results and conclusions. There are close correlations between the invasively measured parameters and the parameters derived from non-invasive measurement through another correlation method according to the present invention. An improved formulation is disclosed for a non-invasively derived analogue of Left Ventricular End-Diastolic Pressure (LVEDP). In diastole, the left ventricular pressure is an exponential function of left ventricular volume, and this relation holds at any point during the diastolic filling interval including end-diastole. Therefore, LVEDP is an exponential function of Left Ventricular End-Diastole Volume (LVEDV).

Let DI be the diastolic filling interval. To a reasonable approximation, $$DI = T - EI \quad \text{Eq. 25}$$

where T is the time period of the cardiac cycle. T is non-invasively obtained by measuring the time interval between R-waves in the EKG and is linearly proportional to the reciprocal of the heart rate (HR) in beats per minute. That is, $$T = (1/HR)*60 \text{ sec/min} \quad \text{Eq. 26}$$

This approximation ignores the time required for isovolumic contraction and relaxation. Since these intervals are relatively small fractions of any cardiac cycle, the approximation is a useful one for the present invention. In addition to the method of obtaining DI as shown in Eq. 26, DI may be obtained by a 1 MHz Doppler ultrasound device placed on the surface of the patient's chest just over the left ventricle. Diastolic filling has a characteristic low velocity blood flow that causes an analogously low Doppler frequency shift. The duration of this characteristic low frequency Doppler shift substantially serves as an accurate measure of DI. DI starts when the mitral valve opens, and DI ends when the mitral valve slams shut. The Doppler device is relatively expensive and has the advantage for use with obese patients. In some situations, DI is also optionally obtained with an ordinary stethoscope or phonocardiogram. An ordinary stethoscope or phonocardiogram indicates that DI ends as it is marked by the first heart sound of the 'lub' in the two sounds of the 'lub-dub'. In patients with certain pathology, an 'opening snap' of the mitral valve is audible in the stethoscope. Perhaps a phonocardiogram shows when the mitral valve opens in most patients. Alternatively, the above mentioned fiberoptic sensor that is placed upon the precordium of the chest obtains DI by measuring the duration of the low frequency vibrations in the amplitude of the fiberoptic light signal which are due to diastolic filling. Preferably, DI used in the present invention is derived according to Eq. 25

Figure 24:
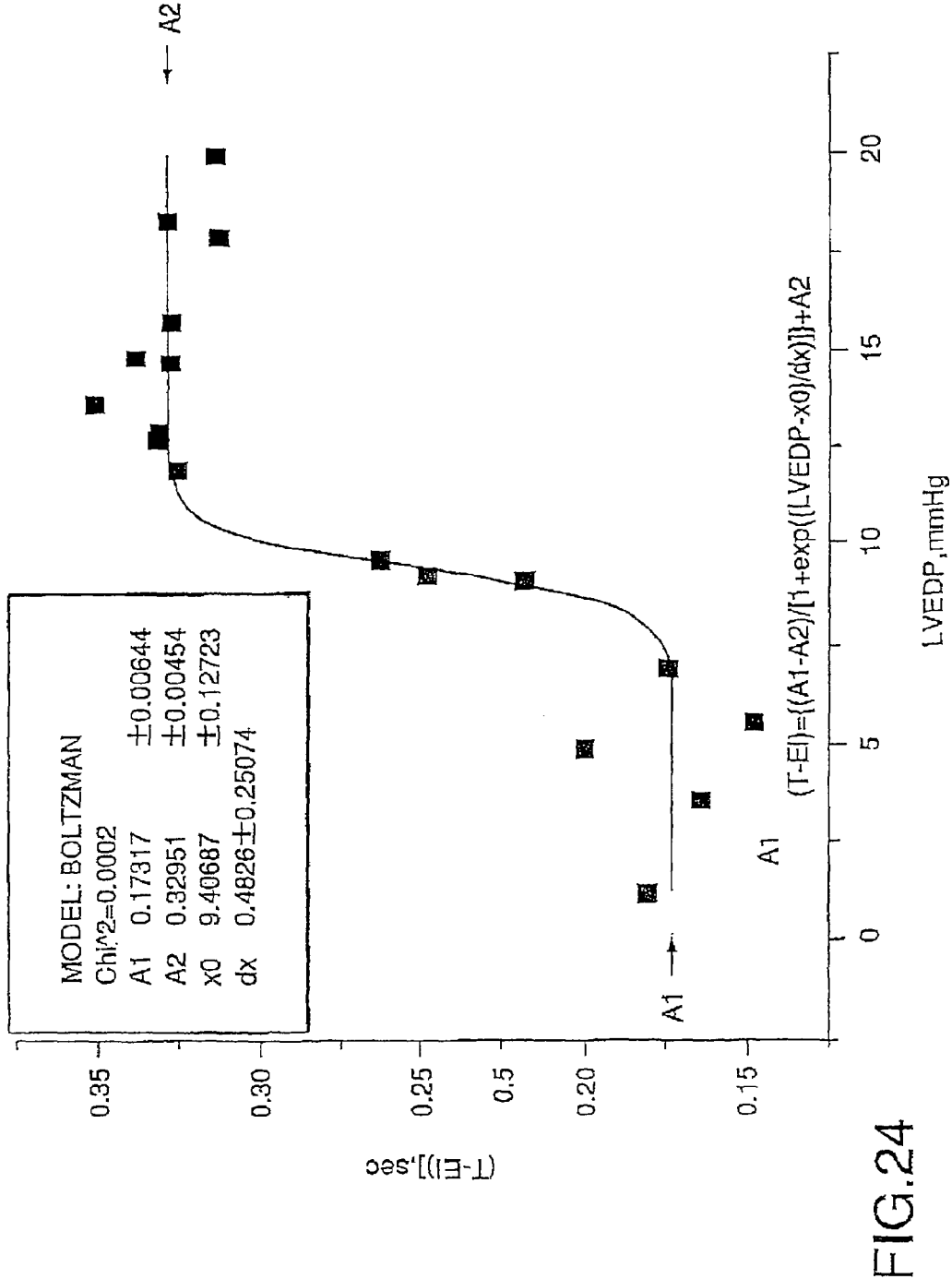
FIG. 24 is a graph illustrating the Sigmoidal relation between the filling interval (T−EI) and LVEDP for the first subject according to the second embodiment of the present invention.
Figure 25:
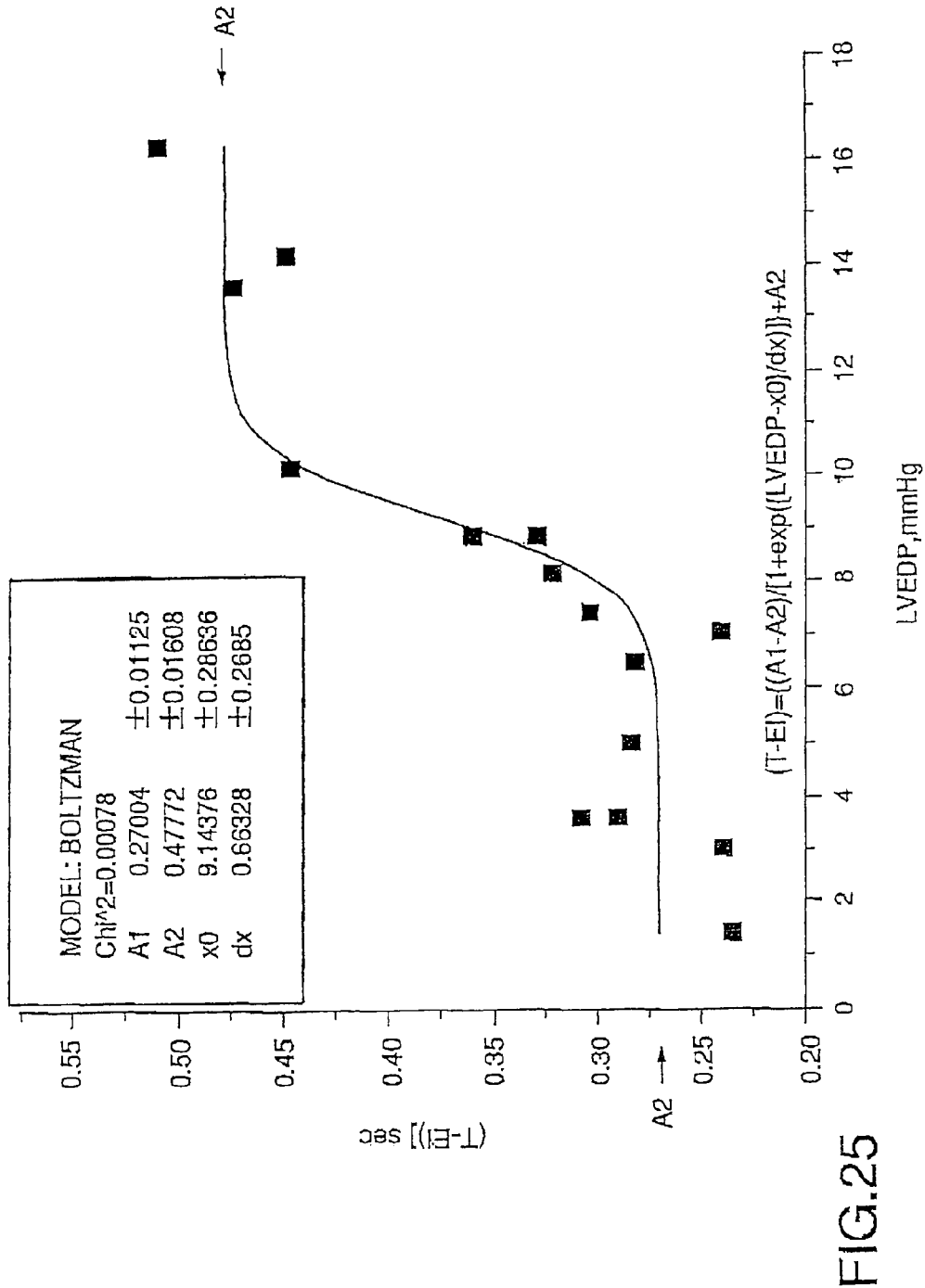
FIG. 25 is a graph illustrating the Sigmoidal relation between the filling interval (T−EI) and LVEDP for the second subject according to the second embodiment of the present invention.

The relation between LVEDP and the quantity DI=T-EI is shown for Pig 1 in FIG. 24 and for Pig 2 in FIG. 25. The relation is sigmoid, and is given by the Boltzman equation $$(T-EI) = \{(A1-A2)/[1+\exp(\{LVEDP-x0\}/dx)]\} + A2 \quad \text{Eq. 27}$$

where A1 and A2 are asymptotes, A2>A1. The quantity (T-EI) at x=x0 is the average value of the two asymptotes, and 'dx' is a proportionality constant which decreases with the steepness of the sigmoid rise.

The data in FIGS. 24 and 25 represents a full range of Contractility and SVR. The data in FIGS. 24 and 25 shows excellent agreement with Eq. 27. By fitting these data with Eq. 27, we obtain a Chi-Square of 0.0002 for the fitting of the Pig 1 data and a Chi-Square of 0.00078 for the Pig 2 data. The remarkably good agreement between Eq. 27 and the experimental data shows a relationship between LVEDP and exactly one non-invasively measurable time interval. When EI or T by itself is plotted as a function of LVEDP, a similar sigmoid distribution results. But the Chi-Square values for the difference DI=T-EI as a function of LVEDP are lower than for either quantity alone. Ordinarily, when two quantities are subtracted, their errors would add. In this case, the error actually decreases when (T-EI) is used in preference to either EI or T alone. The sigmoid relation between DI and LVEDP represents a completely new correlation between two parameters in mammalian hemodynamics.

Preferably, the above sigmoid relation is used to achieve a better accuracy when LVEDP is near x0 and T-EI is not near one of its asymptote. More preferably, the predictively useful range of (T-EI) for predicting LVEDP is where LVEDP lies between 7-11 mmHg in both pig experiments. Interestingly, the inflection point in the sigmoid curve x0 is 9.40±0.127 for Pig 1, and x0 is 9.14±0.286 for Pig 2. These values of x0 for the two pigs are equal within the limits of experimental error. It is anticipated that with a large population of pigs, that the quantity x0 would lie in a steep bell curve distribution. As known in the relevant prior art, the above data from the pig experiments is a solid foundation for having the substantially similar correlation between the non-invasively measured data and the invasively measured data from humans.

In order for the sigmoid relation shown in FIGS. 24 and 25 to be more useful for predicting LVEDP, T-EI is preferably made linear or at least monotonically increasing with respect to LVEDP and contains no asymptotes. This is accomplished by multiplying (T-EI) by the product MAP*(Q-A"max), where MAP is Mean Arterial Pressure and (Q-A"max) is the time interval between the Q-wave on EKG and the time point of maximum value of the second derivative of arterial pressure with respect to time. In this example, the arterial pressure is measured in the femoral artery.

Figure 26:
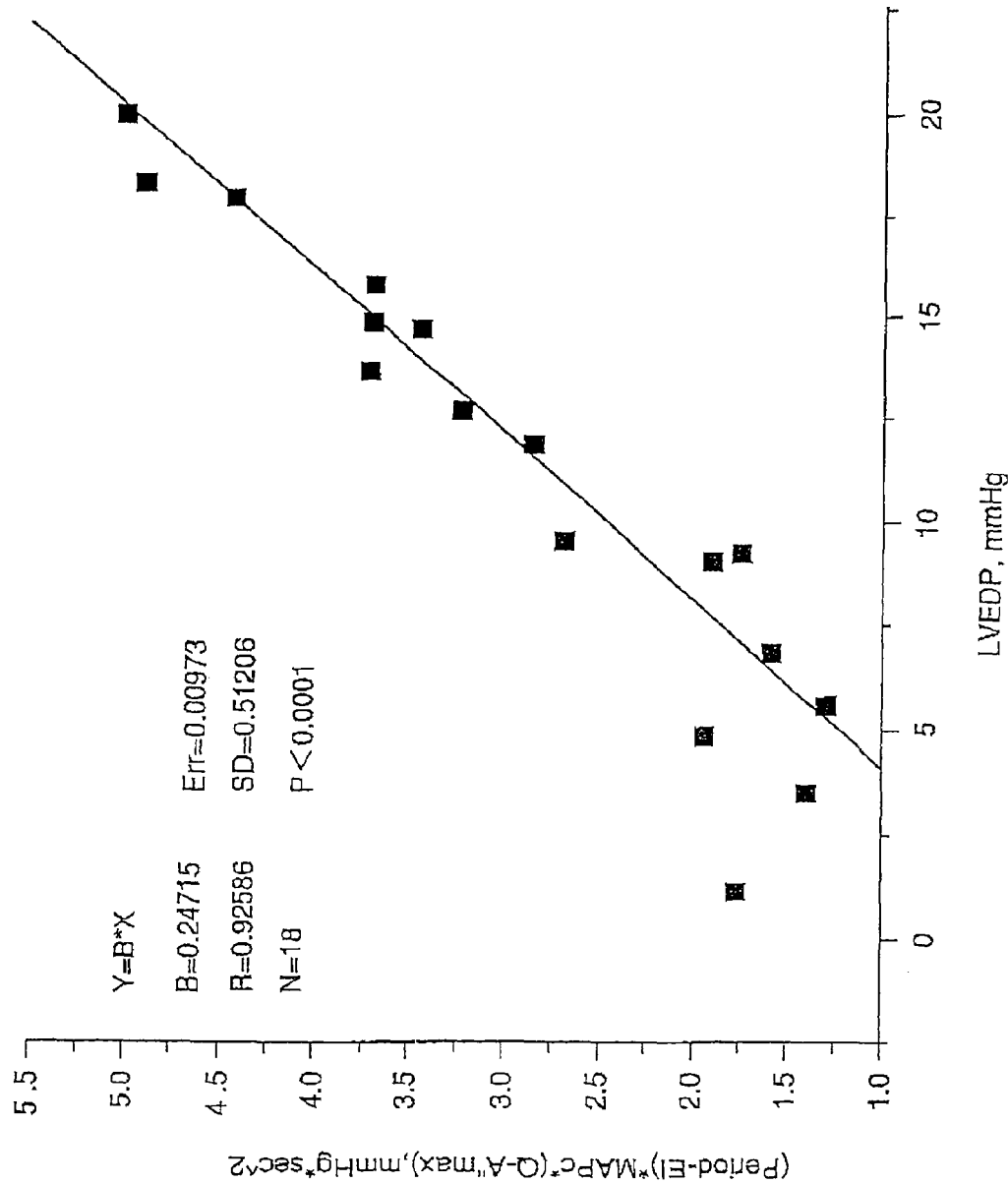
FIG. 26 is a graph illustrating LVEDP in terms of Period, EI, MAPc, and Q-A"max for the first subject according to the second embodiment of the present invention.
Figure 27:
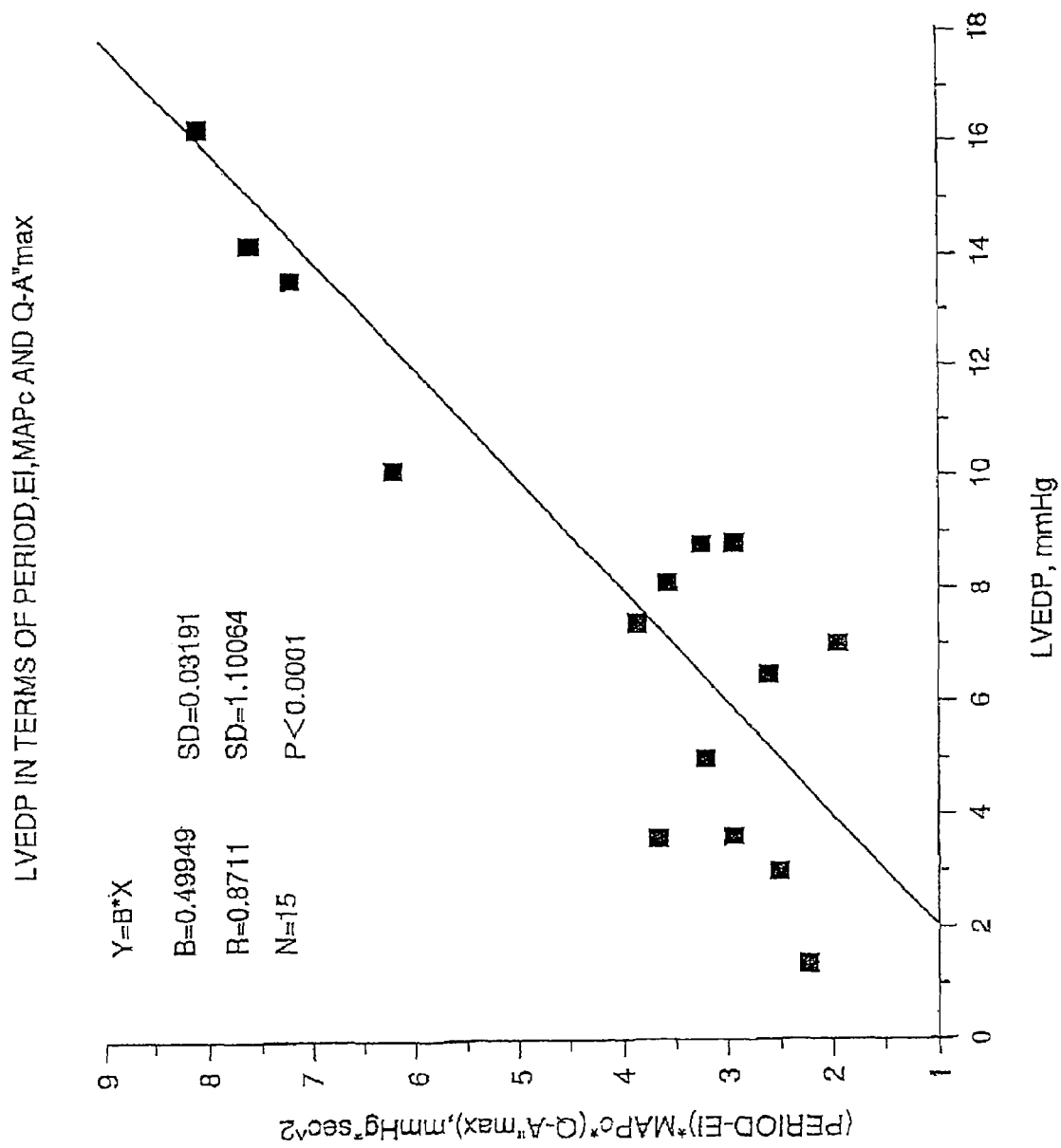
FIG. 27 is a graph illustrating LVEDP in terms of Period, EI, MAPc, and Q-A"max for the second subject according to the second embodiment of the present invention.

FIGS. 26 and 27 respectively show the quantity (T-EI) *MAP*(Q-A"max) as a function of LVEDP in Pig 1 and Pig 2. In Pig 1, the linear correlation coefficient R is 0.92586. In Pig 2, the linear correlation coefficient R equals to 0.8711.

This represents a great improvement over the linear correlation coefficient of EI*MAP*(Q-A"max) vs. LVEDP, where the linear correlation coefficient R equals to 0.70677. Therefore, (T−EI)*MAP*(Q-A"max) is an improved non-invasively measured correlate of LVEDP over EI*MAP*(Q-A"max).

Figure 28:
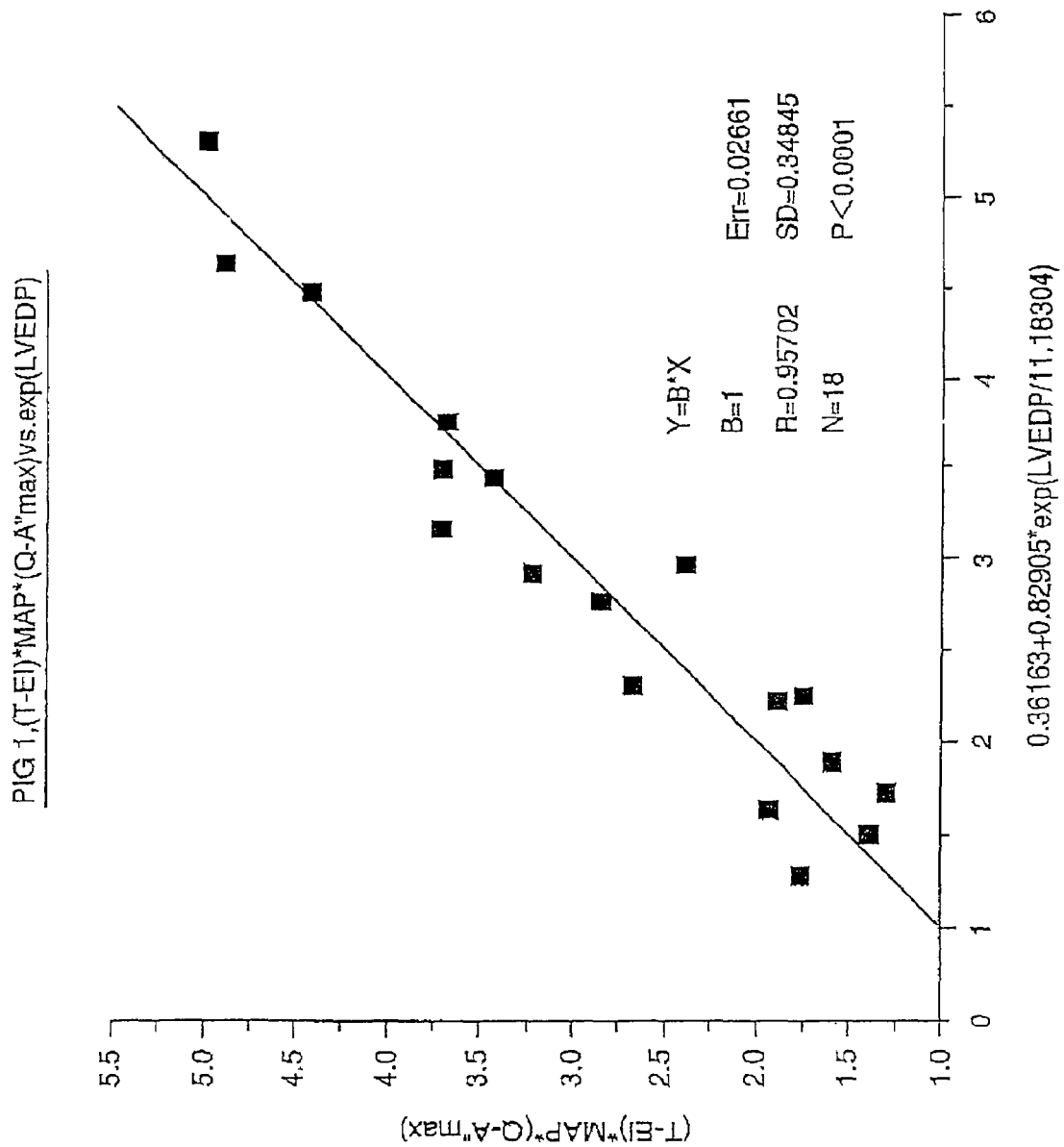
FIG. 28 is a graph illustrating the linear relationship between (T−EI)*MAP*(Q-A"max) and exp(LVEDP) for the first subject according to the second embodiment of the present invention.
Figure 29:
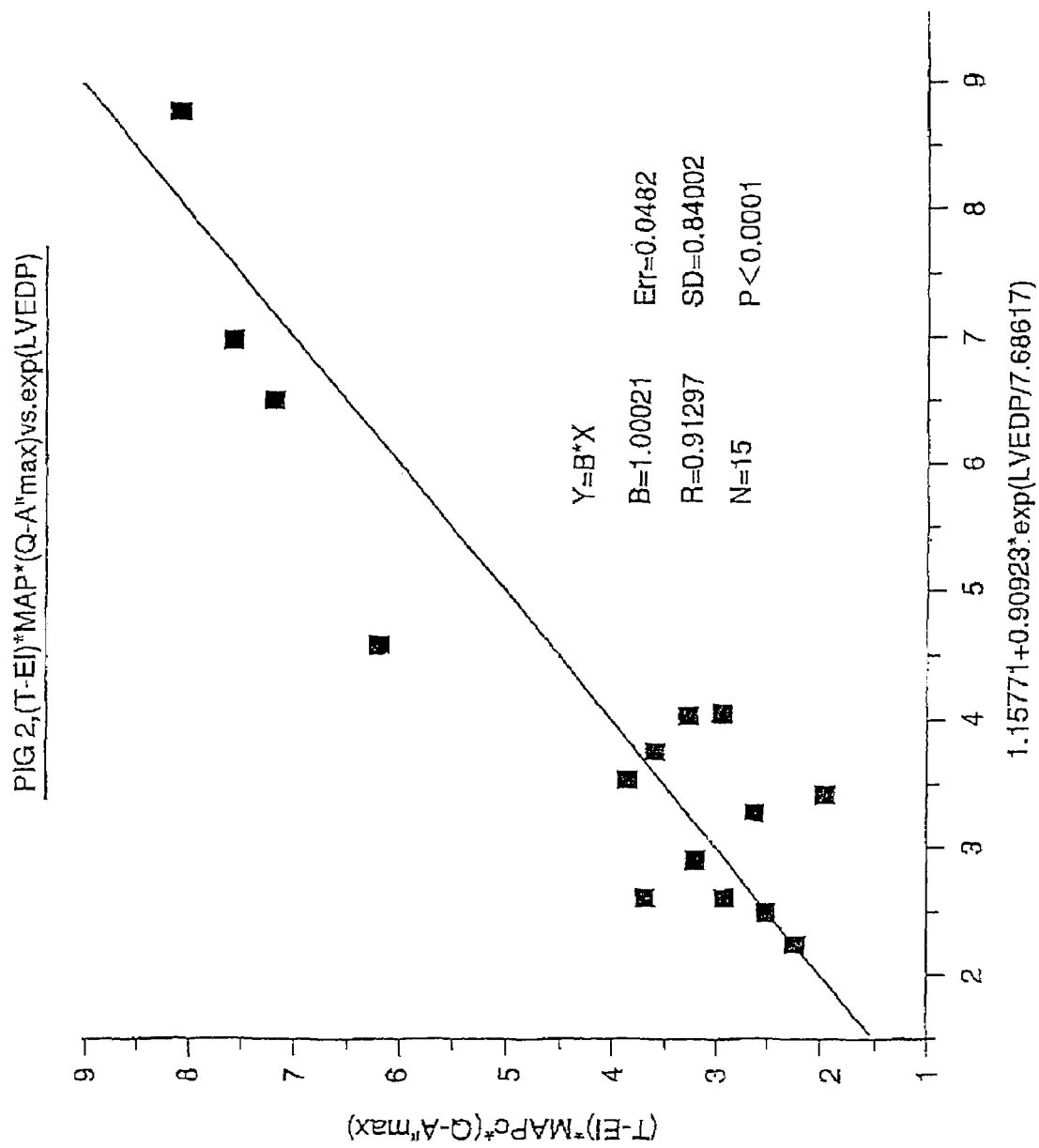
FIG. 29 is a graph illustrating the linear relationship between (T−EI)*MAP*(Q-A"max) and exp(LVEDP) for the second subject according to the second embodiment of the present invention.

The relations shown in FIGS. 26 and 27 are not perfectly linear. FIG. 26 in particular has a modest exponential component. If we removed the exponential character from the Pig 1 results as shown in FIG. 26 by plotting (T−EI)*MAP*(Q-A"max) against an exponential function of LVEDP, we would get an even better linear correlation R=0.95702 as shown in FIG. 28. Similarly, if we removed the exponential character from the Pig 2 results as shown in FIG. 27 by plotting (T−EI)*MAP*(Q-A"max) against exp(LVEDP), we would get an improved linear correlation of R=0.91297 as shown in FIG. 29. It is reasonable that more and better data will lead to better correlations.

In addition to the correlations described above, additional correlation has been developed between the non-invasively measured cardiac parameters and other cardiac parameters that are normally measured invasively or difficult to obtain.

1) Correlation Between SVRc and the Second Plurality of Non-Invasive cardiac Parameters.

An alternative approximation to the Afterload is SVRc. SVRc is the Systemic Vascular Resistance defined only over the ejection interval (EI). That is precisely the interval over which resistance to flow is offered by the resistance vessels at the arteriolar level of the circulation. By contrast, SVR is defined over the entire cardiac cycle. Let SV be the stroke volume in cc over the ejection interval EI in seconds. Then by Ohm's Law, $$SVRc=MAP/[SV/EI] \quad \text{Eq. 29}$$

We have already shown that the quantity [SV/EI] has a very high linear correlation with exp(1/Q-A"max), with R=0.97997 for Pig 1 and R=0.95425 for Pig 2. Substituting exp(1/Q-A"max) for [SV/EI] in Eq. 29 gives us $$SVRc \propto MAP/[exp(1/Q\text{-}A\text{"max})] \quad \text{Eq. 30}$$

where '∝' indicates a linearly proportional relationship.

There is a practical problem with using Eq. 30 as an index of Afterload. As the denominator becomes small relative to the numerator, the random error in the quotient MAP/exp(1/(Q-A"max) becomes magnified in such a way as to preclude deriving a continuous function at the right hand portion of the curve where (Q-A"max) becomes large (that is, as (Q-A"max) becomes large and exp(1/Q-A"max) tends toward 1). This problem is easily fixed simply by adding a constant K in the denominator. K must be sufficiently large that the denominator '[K+exp(1/Q-A"max)]' is on the same order of magnitude as the numerator, MAP over the physiologic range. We can write $$SVRc \propto MAP/[K+exp(1/Q\text{-}A\text{"max})] \quad \text{Eq. 31}$$

$$SVRc = A1*MAP/[K+exp(1/Q\text{-}A\text{"max})]+A2 \quad \text{Eq. 31a}$$

Where K, A1 and A2 are empirical proportionality constants. The units of K are $sec^{-1}$. For Pig 1, K=400 $sec^{-1}$, and for Pig 2, K=70 $sec^-$. Eq. 31 shows that SVRc can be derived from non-invasively measured results MAP, Q-A"max.

Figure 30:
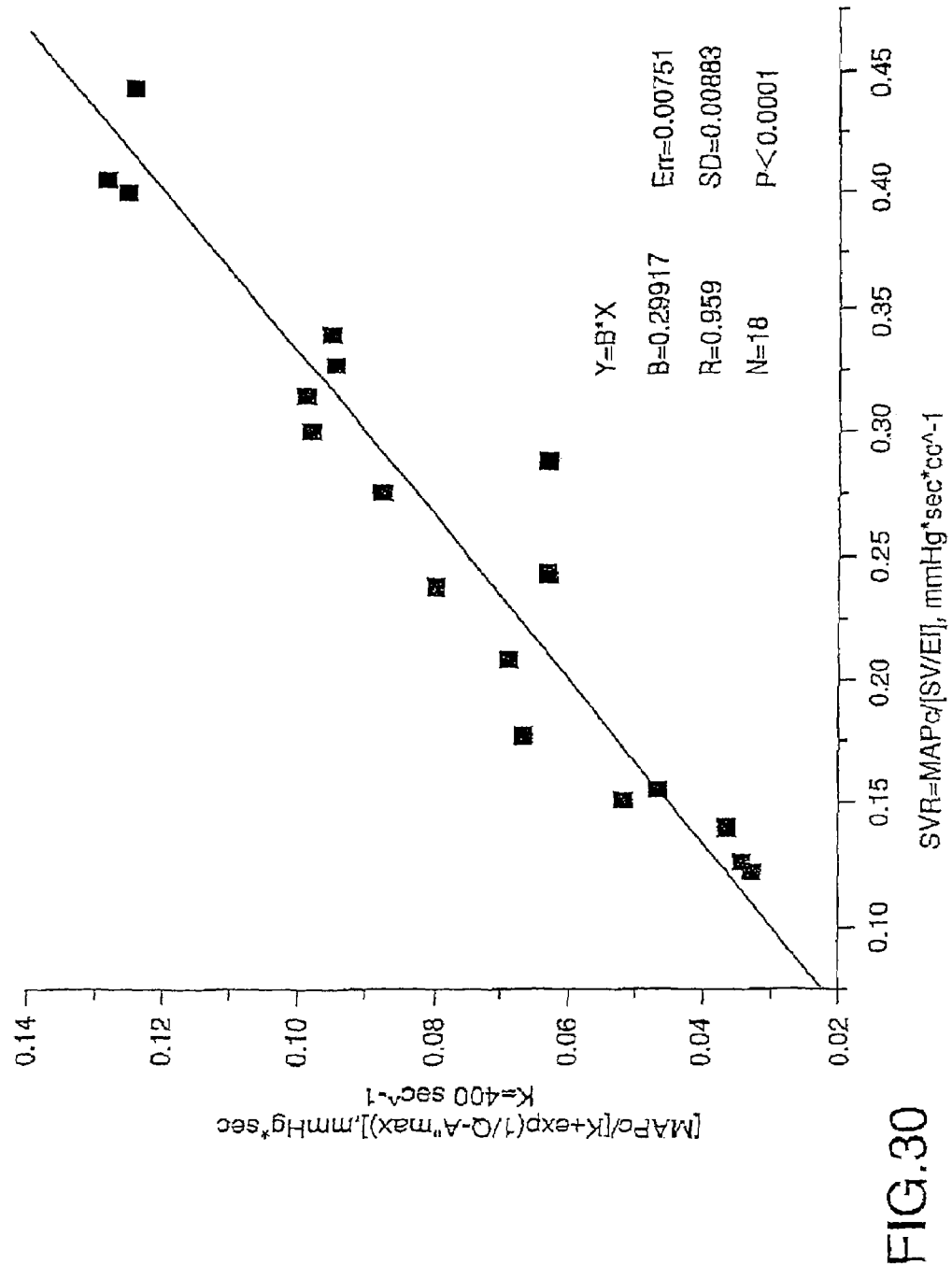
FIG. 30 is a graph illustrating SVRc in terms of MAPc and Q-A"max for the first subject according to the second embodiment of the present invention.
Figure 31:
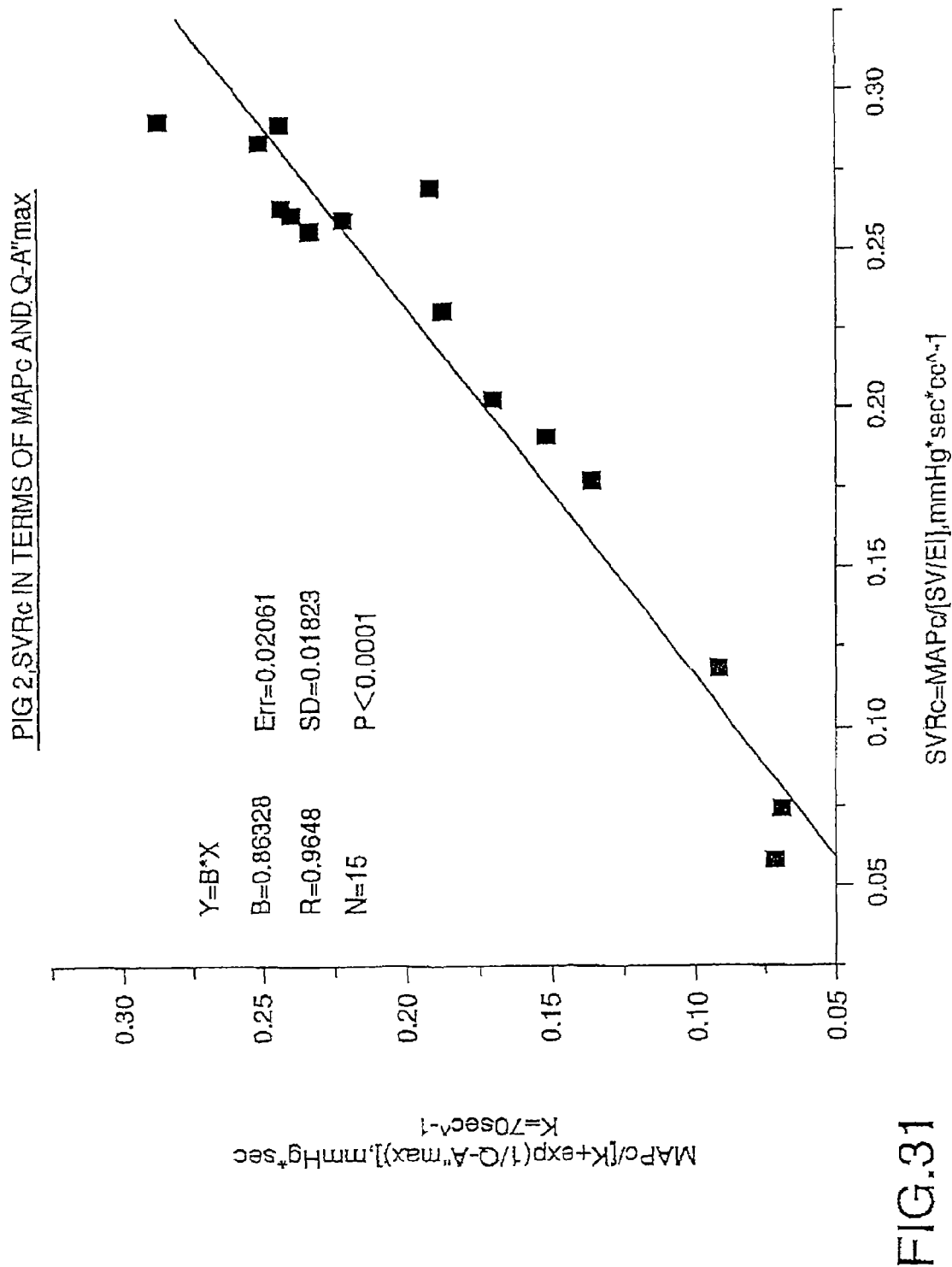
FIG. 31 is a graph illustrating SVRc in terms of MAPc and Q-A"max for the second subject according to the second embodiment of the present invention.

FIGS. 30 and 31 plot the invasively measured SVRc against MAP/[K+exp(1/Q-A"max)], which is essentially the SVRc derived non-invasively respectively for Pig 1 and Pig 2. The correlation coefficient R equals to 0.959 and 0.9648 respectively for Pig 1 and Pig 2. The above correlations strongly confirm that SVRc is indeed derived from MAP and Q-A"max, both of which are measured without invasion of the patient.

Figure 32:
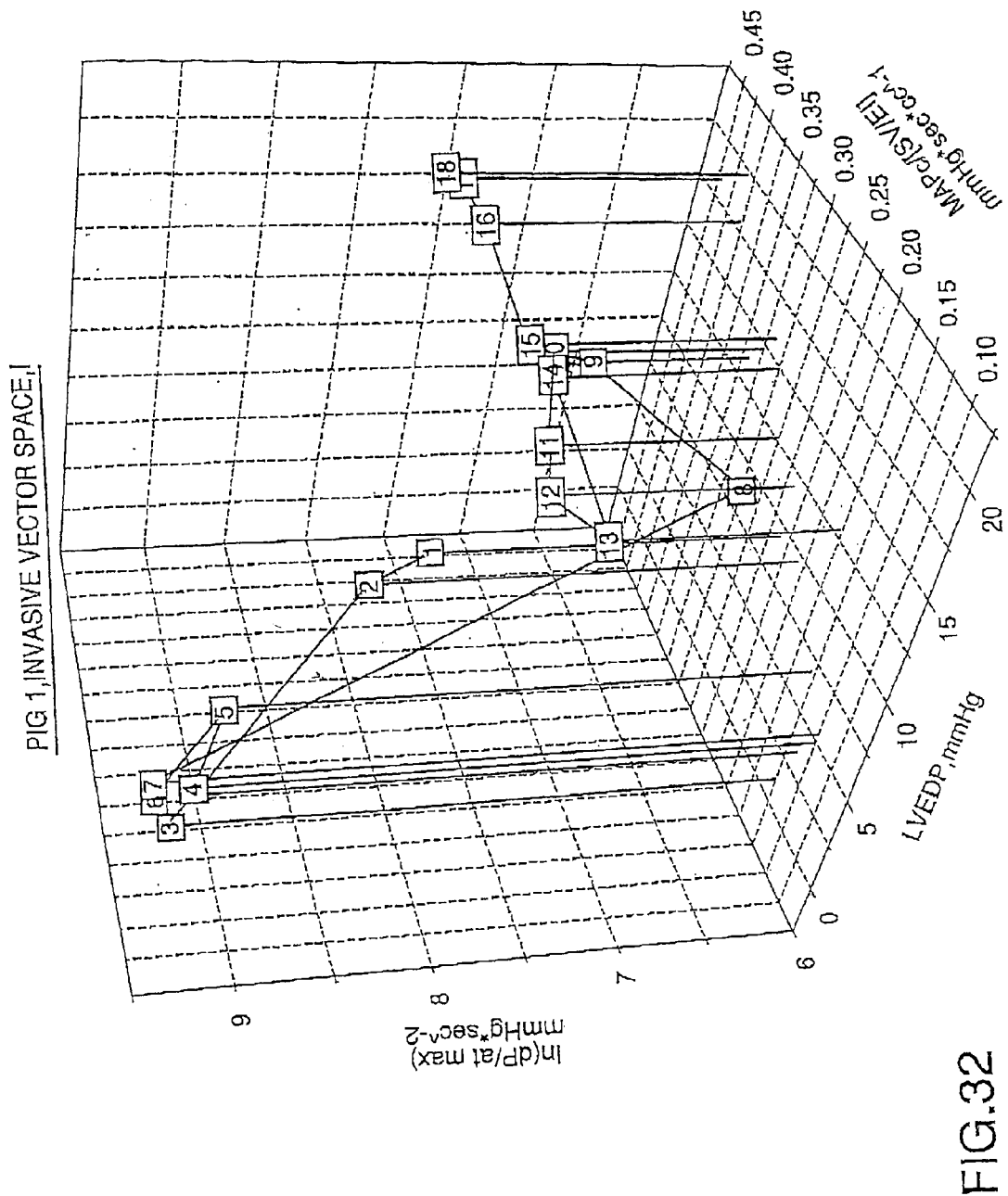
FIG. 32 is a graph illustrating an invasive hemodynamic vector space for the first subject according to the second embodiment of the present invention.
Figure 33:
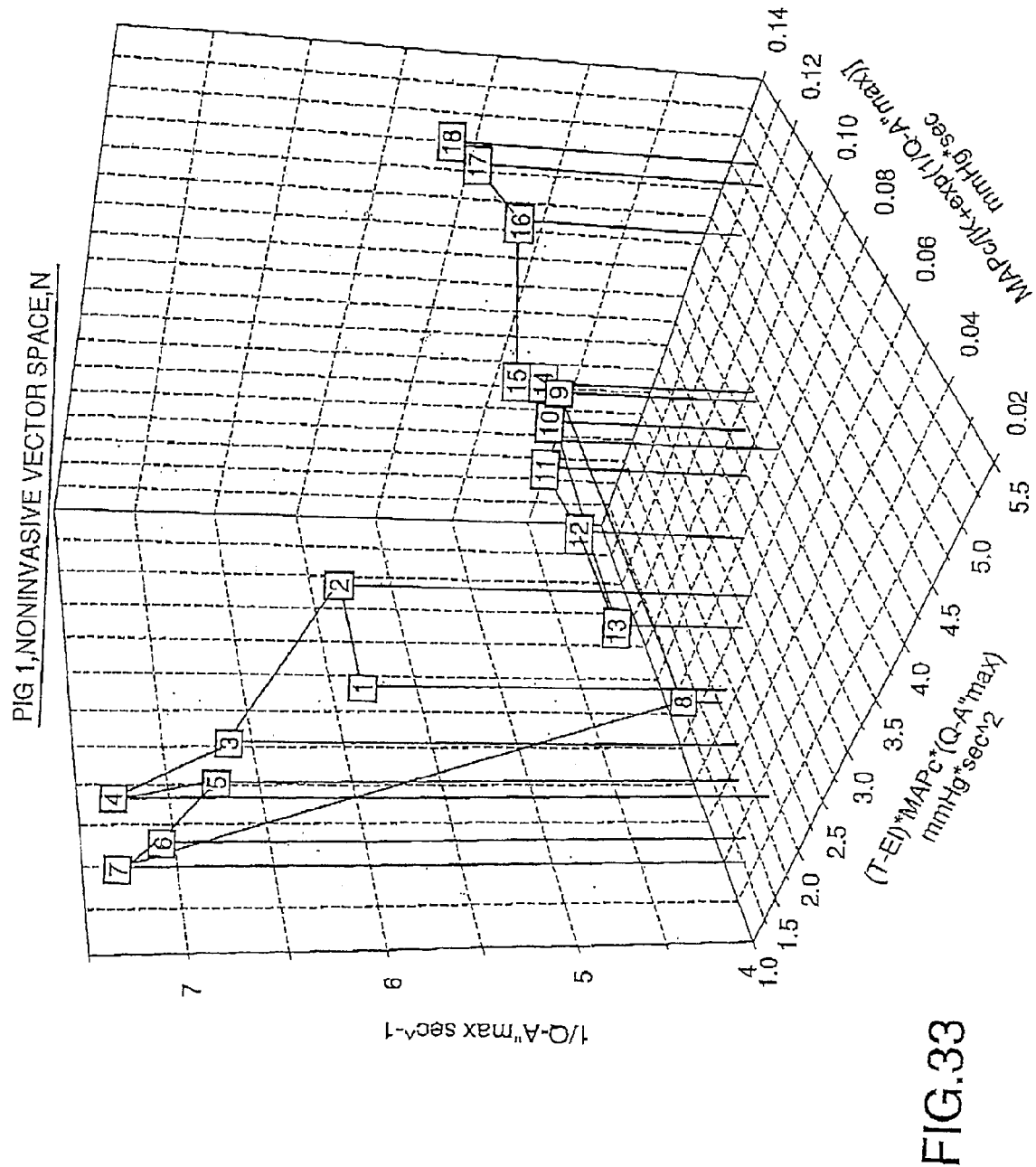
FIG. 33 is a graph illustrating a non-invasive hemodynamic vector space for the first subject according to the second embodiment of the present invention.
Figure 34:
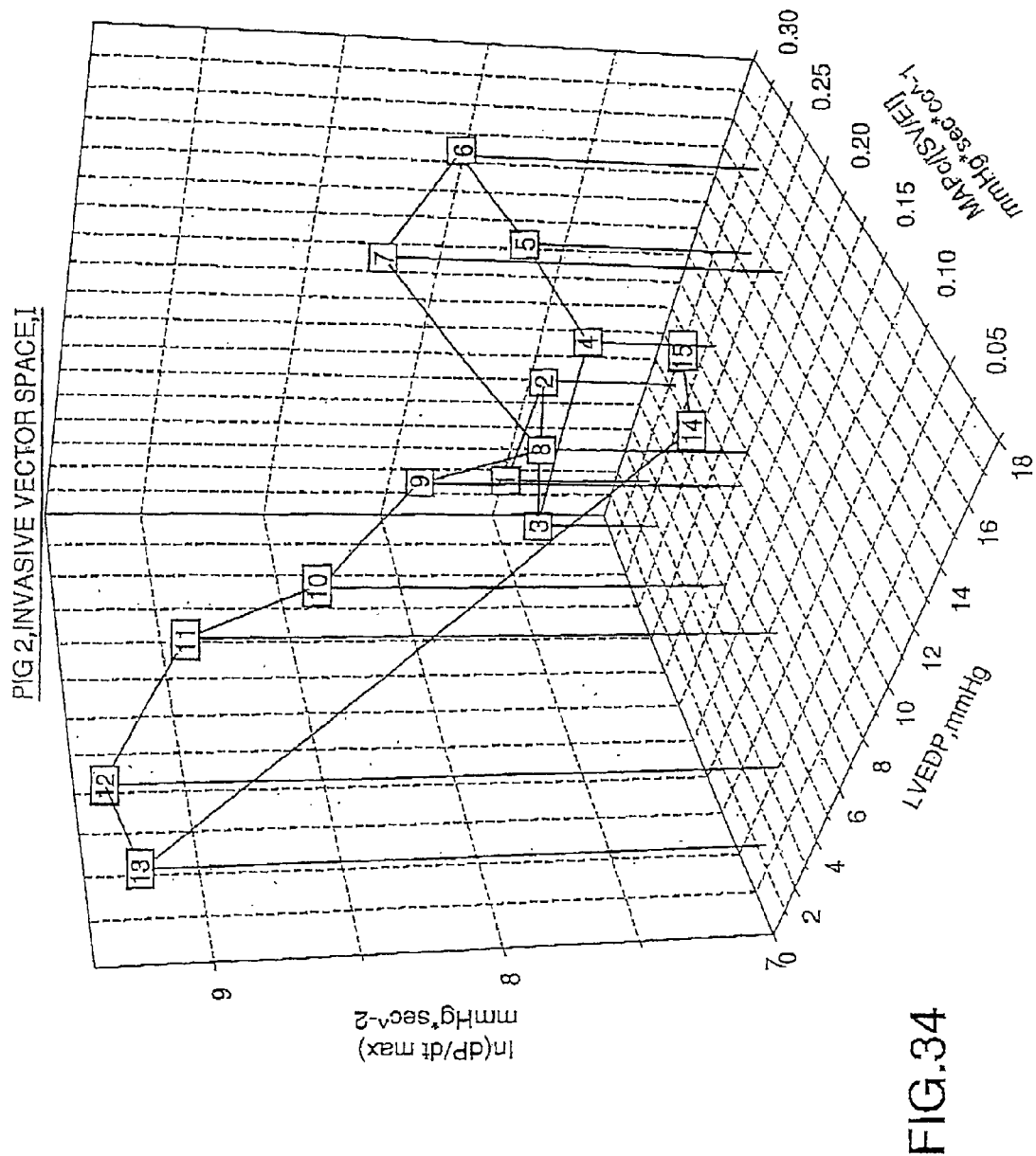
FIG. 34 is a graph illustrating a first embodiment of an invasive hemodynamic vector space for the second subject according to the second embodiment of the present invention.
Figure 35:
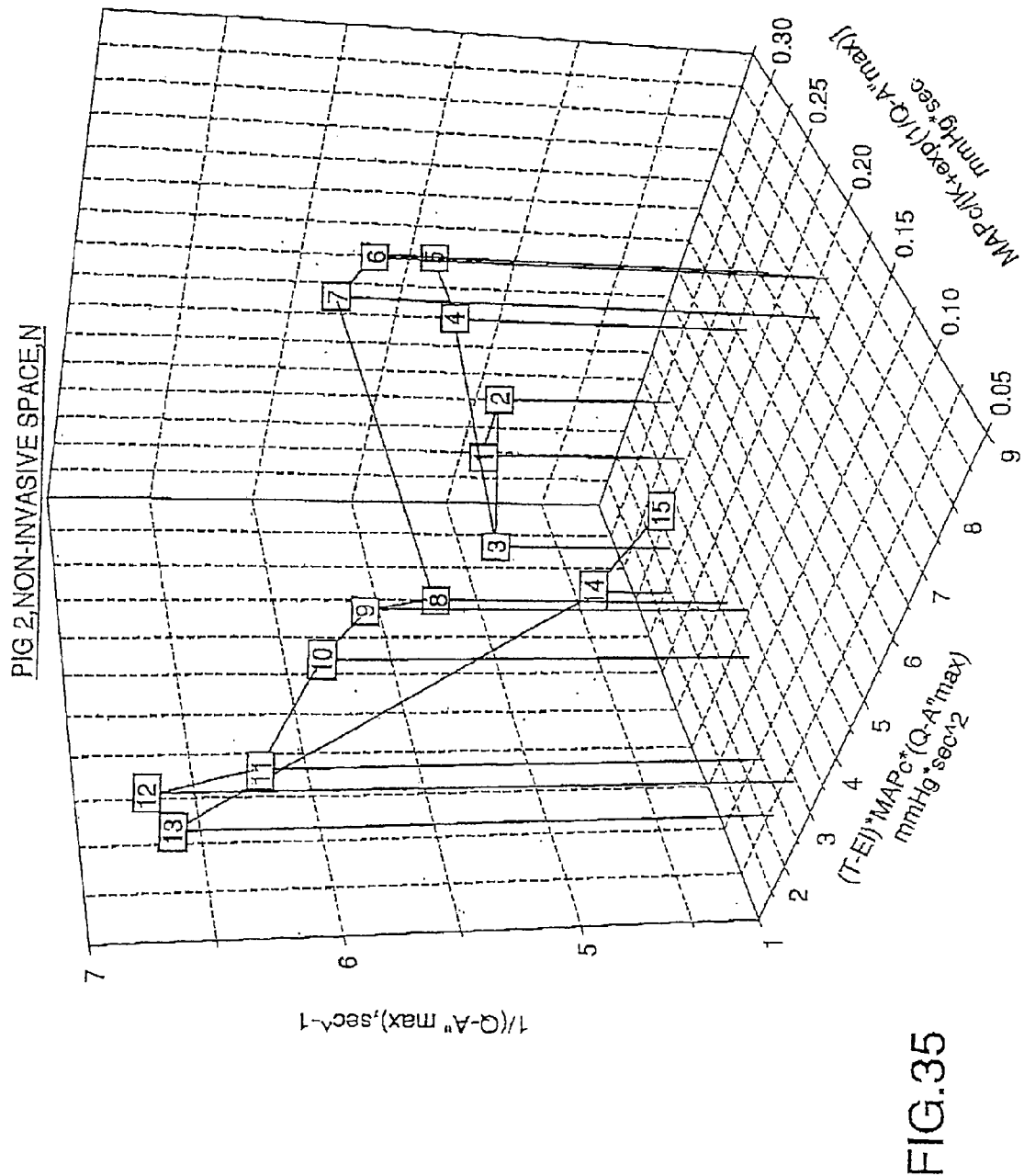
FIG. 35 is a graph illustrating a first embodiment of a non-invasive hemodynamic vector space for the second subject according to the second embodiment of the present invention.
Figure 36:
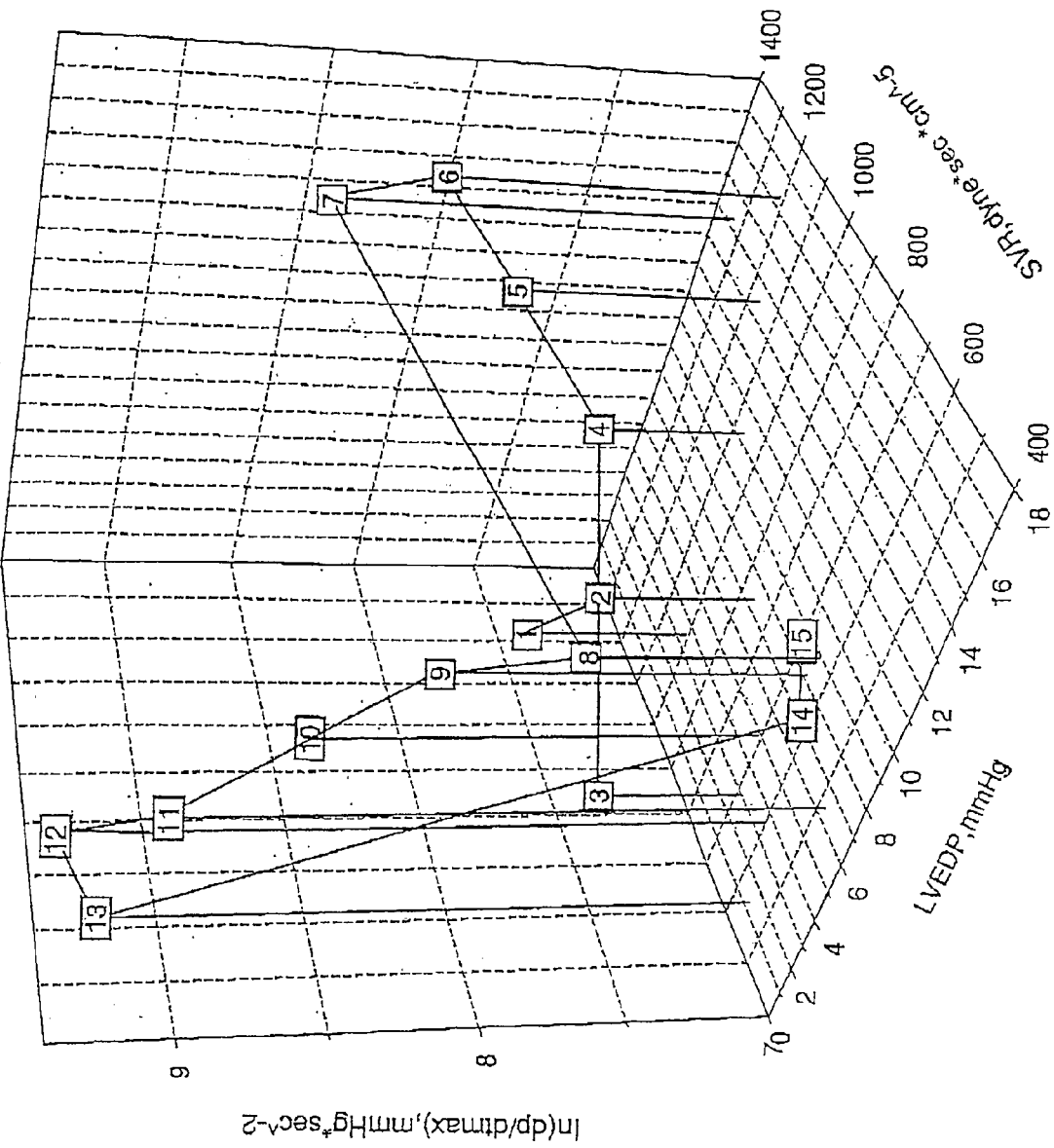
FIG. 36 is a graph illustrating a second embodiment of the invasive hemodynamic vector space for the second subject according to the second embodiment of the present invention.
Figure 37:
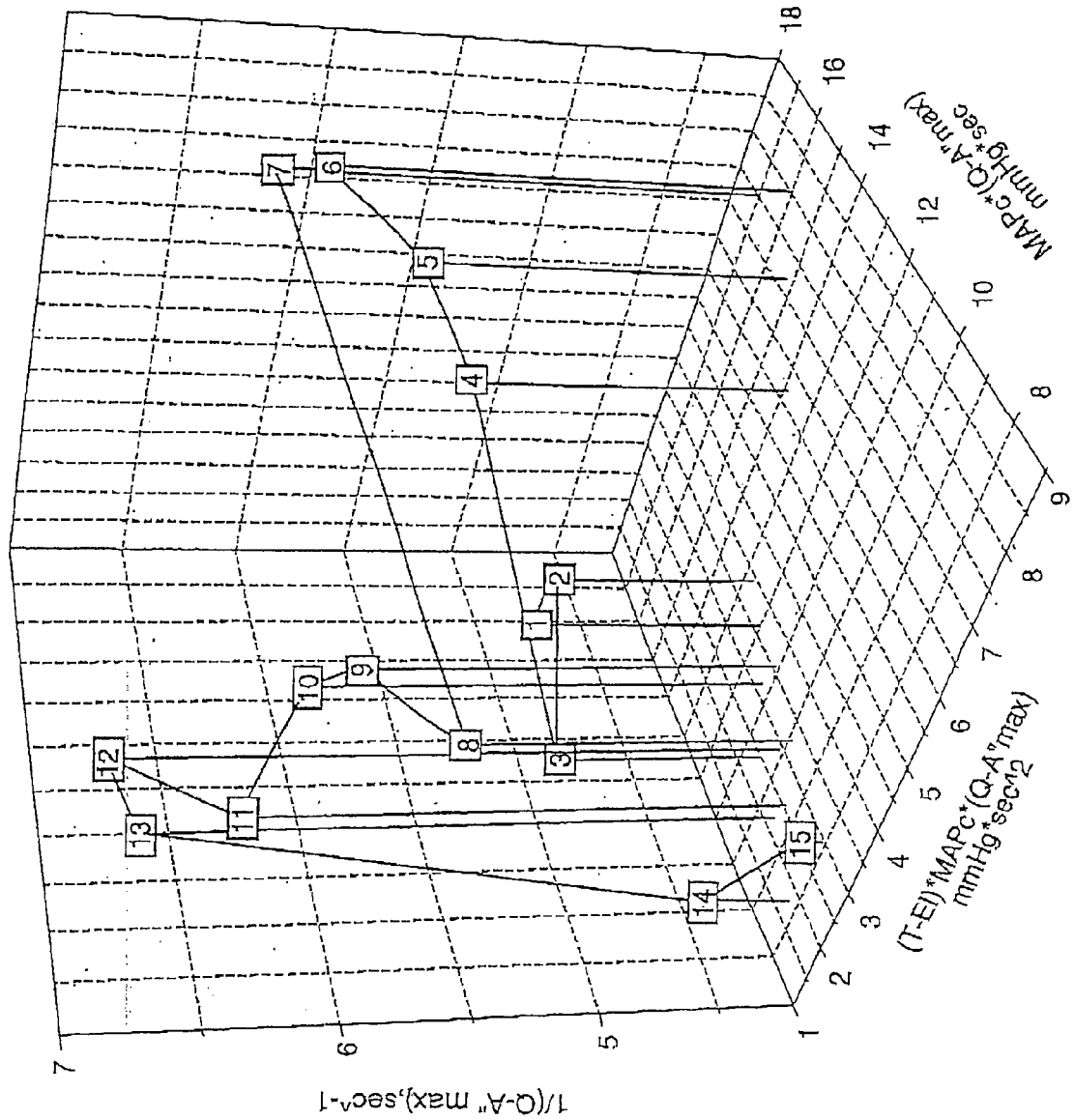
FIG. 37 is a graph illustrating a second embodiment of the non-invasive hemodynamic vector space for the second subject according to a second embodiment of the present invention.

To further confirm the practicality and effectiveness of the correlation in the second preferred embodiment according to the present invention, the vector trajectories in three dimensional hemodynamic invasive vector space are compared with vector trajectories in the Non-Invasive Space. The invasive spaces are shown in FIGS. 32, 34, and 36. Non-invasive spaces are shown in FIGS. 33, 35, and 37. Each of pairs of FIGS. 32 and 33; 34 and 35; 36 and 37 describes the same events in the same pig with a vector obtained either invasively or non-invasively. Therefore, in another embodiment, the plurality of invasive cardiac analogues are represented by LVEDP, SVRc and dP/dtmax, which are respective approximation to P, A and C. Among the plurality of invasive cardiac analogues, SVRc is defined by Eq. 31a.

FIGS. 32 and 33 represent experimental data for Pig 1. In FIG. 32, the invasive Afterload is represented on the 'y' axis as SVRc=MAP/[SV/EI], that is the mean arterial pressure divided by the average systolic ejection rate. In FIG. 33, the non-invasive Afterload is represented on the 'y' axis by SVRc $\alpha$ MAP/[K+exp(1/Q-A"max)]. Also in FIG. 33, the non-invasive Preload is represented as [(T−EI)*MAP*(Q-A"max)]. The homology between FIGS. 32 and 33 is striking and clearly visualized by a skilled person in the art.

FIGS. 34 and 35 represent experimental data for Pig 2. In FIG. 34, the invasive Afterload is represented on the 'y' axis as SVRc=MAP/[SV/EI], that is the mean arterial pressure divided by the average systolic ejection rate. In FIG. 35, the non-invasive Afterload is represented on the 'y' axis by SVRc $\alpha$ MAP/[K+exp(1/Q-A"max)]. Also in FIG. 35, the non-invasive Preload is represented as [(T−EI)*MAP*(Q-A"max)]. The homology between FIGS. 34 and 35 is striking and clearly visualized by a skilled person in the art.

FIGS. 36 and 37 also represent experimental data for Pig 2. In FIG. 36, the invasive Afterload is represented on the 'y' axis as SVR obtained from the Swan-Ganz data. In FIG. 37, the non-invasive Afterload is represented on the 'y' axis by MAP*(Q-A"max), which is the non-invasive analogue of SVR. The non-invasive Preload is represented as [(T−EI)*MAP*(Q-A"max)]. The homology between FIGS. 36 and 37 is striking and is visualized by a skilled person in the art.

2) An Improved Index of Left Ventricular Ischemia

The average compliance CP of the left ventricle over the diastolic filling interval is $$CP = \Delta V/\Delta P \quad \text{Eq. 32}$$

where $\Delta V$ is just the stroke volume SV. In the steady state, the volume of blood filling the left ventricle equals the volume of blood ejected from it. But since SV $\alpha$ EI*(exp(1/Q-A"max)) as shown previously, we substitute SV for $\Delta V$ in the numerator of Eq. 32. $\Delta P$ in diastole is the Left Ventricular End-Diastolic Pressure (LVEDP) minus the LV Pressure at the end of isovolumic relaxation (Peivr). Thus, $\Delta P$=LVEDP−Peivr. Since Peivr is always going to be a very low number or close to zero, for practical purposes, we can ignore it. Assuming that Peivr is near zero, and substituting EI*exp(1/Q-Amax) for $\Delta V$ and (T−EI)*MAP*(Q-A"max) for $\Delta P$ in Eq. 32, we get $$CP \propto [EI*exp(1/Q\text{-}A\text{"max})]/[(T-EI)*MAP*(Q\text{-}A\text{"max})] \quad \text{Eq. 33}$$

Rearranging terms, we get $$CP \propto [EI/(T-EI)]*[\exp(1/Q\text{-}A''\max)/(MAP*Q\text{-}A''\max)] \quad \text{Eq. 34}$$

$$\text{or} \quad CP = A3*[EI/(T-EI)]*[\exp(1/Q\text{-}A''\max)/(MAP*Q\text{-}A''\max)] + A4 \quad \text{Eq. 34a}$$

where A3 and A4 are empirical proportionality constants.

In an ischemic event, there should be a sudden decrease in the value of the average compliance CP that precedes the onset of regional wall motion abnormalities on 2-D echocardiography, which in turn will precede the onset of S-T segment changes on EKG. The above diagnostic feature of the average compliance CP would make non-invasive left ventricular diastolic compliance measurement far superior and more sensitive to any diagnostic tool that is now available for ischemia detection and treatment efficacy monitoring. Therefore, a preferred method of predicting an ischemic event according to the present invention detects ischemic events well ahead of other currently available monitors by measuring T, EI, MAP and Q-A"max. Therefore, in another aspect, the present invention provides a method, a system and a correlation to derive at least one clinically useful cardiac parameter or invasive cardiac analogue from a plurality of predetermined non-invasively measured parameters such as T, EI, MAP, Q-D"(t)max, and Q-A"max. The clinically useful cardiac parameters include CP, which is useful in predicting an ischemic event; and P, A, C, analogues thereof and approximations thereof, which are useful in monitoring a patient's cardiac state and in determining the need of cardiac medicines such as dobutamine, nitroglycerine, phenylephrine, fluids, diruetics, pressors, afterload reducers, anesthetics, inotropes and negative inotropes.

Although the inventor does not want to limit the predictability of $[EI/(T-EI)]*[\exp(1/Q\text{-}A''\max)/(MAP*Q\text{-}A''\max)]$ according to the present invention to a particular theory, a possible explanation for detecting an ischemic event is as follows. An acute ischemic event typically does not manifest itself in exactly one cardiac function parameter. Rather, it is a rapidly emerging gestalt that affects all four parameters including heart rate, Preload, Afterload, and Contractility in a characteristic way over a characteristic time course. During an ischemic event, myocardial oxygen demand exceeds the supply. Now, there is not enough ATP being created by the oxygen requiring respiratory enzymes for the oxidation of glucose substrate. The missing ATP is needed to break the cross-links that form between actin and myosin fibrils as a result of muscle contraction. Muscle relaxation is an energy-requiring and oxygen-requiring process. Without sufficient oxygen, the actin-myosin cross-links remain in place at the end of diastole. The remaining, unbroken cross-links cause the left ventricle muscle to stiffen during filling. In other words, left ventricular diastolic compliance decreases.

Concomitant with the ischemic event is a decrease in Contractility. At same time, stroke volume and cardiac output fall. Afterload increases as the organism responds to sympathetic nerve signals by increasing the systemic vascular resistance (SVR) by selectively constricting smooth muscular arterioles. The increase in SVR compensates in part for the fall in vital end-organ perfusion pressure caused by the fall in cardiac output. By globally increasing SVR by selective vasoconstriction of blood flow to non-critical organ systems such as the gut, liver and muscles, more of the falling and increasingly scarce global cardiac output can be shunted to the brain, heart, and lungs. In short order, Preload increases causing the Starling mechanism of the myocardium to come into play, which compensates for the decrease in stroke volume by increasing it. This increase in Preload occurs simply because, with a decrease in contractility, a smaller fraction of the Left Ventricular End-diastolic Volume is ejected with each stroke, causing blood volume to accumulate in the Left Ventricle with diastolic filling, thereby increasing LVEDP. This distension of the left ventricle in diastolic filling is precisely what we mean by an increase in Preload. With an ischemic event, a choreographed increase in LVEDP, an increase in SVR, and a decrease in Contractility occur almost simultaneously.

Now, referring to Eq. 34, the right hand member contains the term exp(1/(Q-A"max)) in the numerator, which is proportional to Contractility. Therefore, if the compliance CP suddenly decreases, Eq. 34 tells us that Contractility also linearly decreases. The right hand member of Eq. 34 contains [(T-EI)*MAP*(Q-A"max)], which is proportional to Preload, in the denominator. Therefore, by Eq. 34, the compliance CP varies inversely with Preload. If the compliance CP suddenly decreases due to ischemia, Preload inversely increases. The right hand member of Eq. 34 contains the expression [exp(1/Q-A"max)/MAP], which is proportional to (1/SVRc). SVRc then, by Eq. 34, varies inversely with diastolic compliance CP. So if CP were to decrease suddenly due to ischemia, SVRc would increase. But these changes in LVEDP, dP/dtmax, and SVRc that are described by Eq. 34 in the event of a sudden decrease in LV compliance are precisely the choreographed changes in Preload, Afterload, and Contractility that occur in the event of ischemia. In summary, if the compliance CP of the Left Ventricle declines suddenly due to ischemia, this entails an increase in LVEDP, an increase in SVRc, and a sudden decrease in Contractility, which is consistent with our physiological knowledge. What is significant here is that this particular piece of physiologic knowledge can be shown to be a purely logical consequence of the definition of average diastolic compliance, CP, and Eq. 34, which is a relation between average diastolic compliance and a plurality of pre-determined non-invasive cardiac parameters. These non-invasive parameters, in turn, determine the locus of a point in the non-invasive hemodynamic vector space, 'N'.

Another approach to the problem of finding a non-invasively measured index of cardiac ischemia, that is calculated and displayed in real-time, is as follows. We define a vector function of three mutually orthogonal variables, $$Xi = \{LVEDP, SVRc, 1/(\ln(dP/dt\max))\} \quad \text{Eq. 36}$$

We then express the above vector in terms of its non-invasive correlates, $$Xn = \{[(T-EI)*MAP*(Q\text{-}A''\max)], [MAP/(K+\exp(1/Q\text{-}A''\max))], (Q\text{-}A''\max)\} \quad \text{Eq. 37}$$

Then we find the norm of the above vector, that is, the square root of the dot product of the vector with itself. This will gives us an ischemia function 'I', which will abruptly increase during an episode of ischemia, where $$I = \{(T-EI)^2*MAP^2*(Q\text{-}A''\max)^2 + MAP^2/\{K+\exp(1/Q\text{-}A''\max)\}^2 + (Q\text{-}A''\max)^2\}^{1/2} \quad \text{Eq. 38}$$

While there have been described what are believed to be the preferred embodiments of the present invention, those skilled in the art will recognize that other and further changes and modifications may be made thereto without departing from the spirit of the invention, and it is intended to claim all such changes and modifications as fall within the true scope of the invention.

I claim:

1. A system for retrofitting existing non-invasive cardiac parameter measuring devices to generate invasive cardiac analogues, comprising:

an interface unit for receiving predetermined non-invasive cardiac parameters of a subject from the existing non-invasive cardio monitoring devices; and a conversion unit connected to said interface unit for converting the non-invasive cardiac parameters into a plurality of the invasive cardiac analogues based upon a set of predetermined conversion equations, wherein said conversion unit outputs the predetermined invasive cardiac analogues including preload as denoted by P, afterload as denoted by A and contractility as denoted by C.

2. The system for retrofitting existing non-invasive cardio monitoring devices according to claim 1 wherein the existing non-invasive cardiac parameter measuring devices measure the predetermined non-invasive cardiac parameters from a human.

3. The system for retrofitting existing non-invasive cardio monitoring devices according to claim 1 wherein the existing non-invasive cardiac parameter measuring devices measure the predetermined non-invasive cardiac parameters from an animal.

4. The system for retrofitting existing non-invasive cardio monitoring devices according to claim 1 wherein the existing non-invasive cardiac parameter measuring unit further comprises a heart rate monitor for measuring heart rate as denoted by HR, a vibration sensing device for measuring an ejection interval as denoted by EI and a mechanical event M of an electrical-mechanical interval as denoted by E-M, a blood pressure measuring device for measuring mean arterial pressure as denoted by MAP and an electrocardiogram measuring device for measuring an electrical event E of the electrical-mechanical interval.

5. The system for retrofitting existing non-invasive cardio monitoring devices according to claim 4 wherein said vibration sensing device comprises at least one of a Doppler ultrasound device and a fiber optic device.

6. The system for retrofitting existing non-invasive cardio monitoring devices according to claim 4 wherein said conversion unit determines the P, the A and the C based upon the predetermined conversion equations including $P = k1(EI*MAP*E-M) + c1,$ $A = k2(MAP*E-M) + c2,$ and $\ln(C) k3(1/E-M) + c3$ where k1, k2, c1, c2 and c3 are empirical proportionality constants.

7. The system for retrofitting existing non-invasive cardio monitoring devices according to claim 4 wherein said conversion unit determines the P, the A and the C based upon the predetermined conversion equations including $P = k1'((T-EI)*MAP*E-M) + c1',$ $A = k2'(MAP*E-M) + c2',$ and $\ln(C) = k3'(1/E-M) + c3'$ where k1', k2', k3', c1', c2' and c3' are empirical proportionality constants for a particular one of the subjects and T is a time period of the cardiac cycle for the particular one of the subjects.

8. The system for retrofitting existing non-invasive cardio monitoring devices according to claim 7 wherein the M in the E-M is defined as a time when a second derivative with respect to time, M"(t), reaches a maximum value.

9. The system for retrofitting existing non-invasive cardio monitoring devices according to claim 8 wherein said non-invasive cardiac parameter measuring unit measures an electrical event in determining the E-M, the electrical event being selected from the group consisting of a Q-wave as denoted by Q, a R-wave as denoted by R, a S-wave as denoted by S and an artificial ventricular pacemaker spike.

10. The system for retrofitting existing non-invasive cardio monitoring devices according to claim 8 wherein said non-invasive cardiac parameter measuring unit measures an electrical event in determining the E-M interval by double differentiating an EKG voltage curve which corresponds to ventricular depolarization, V(t), with respect to time and defining the electrical event as a time when V"(t) reaches a maximum positive value.

11. The system for retrofitting existing non-invasive cardio monitoring devices according to claim 8 wherein said non-invasive cardiac parameter measuring unit measures the mechanical event in determining the E-M, the mechanical event selected from the group consisting of a time of an arterial blood pressure upstroke as denoted by TA and a time of a flow velocity upstroke as denoted by TF.

12. The system for retrofitting existing non-invasive cardio monitoring devices according to claim 4 wherein said conversion unit determines the P, the A and the C based upon the predetermined conversion equations including $P = k1'(DI*MAP*E-M) + c1',$ $A = k2'(MAP*E-M) + c2',$ and $\ln(C) = k3'(1/E-M) + c3'$ where k1', k2', k3', c1', c2' and c3' are empirical proportionality constants for a particular one of the subjects and T is a time period of the cardiac cycle for the particular one of the subjects.

13. The system for retrofitting existing non-invasive cardio monitoring devices according to claim 4 wherein said conversion unit determines the P, the A and the C based upon the predetermined conversion equations including $P = k1'((T-EI)*MAP*E-M) + c1',$ $A = k2'*MAP/[K + \exp(1/E-M)] + c2',$ and $\ln(C) = k3'(1/E-M) + c3'$ where k1', k2', k3', c1', c2', c3', and K are empirical proportionality constants for a particular one of the subjects and T is a time period of the cardiac cycle for the particular one of the subjects.

14. The system for retrofitting existing non-invasive cardio monitoring devices according to claim 1 wherein the existing non-invasive cardiac parameter measuring unit further comprises a heart rate monitor for measuring heart rate as denoted by HR, a vibration sensing device for measuring an ejection interval as denoted by EI, a plethysmographic device for measuring a mechanical event M of an electrical-mechanical interval as denoted by E-M, a blood pressure measuring device for measuring mean arterial pressure as denoted by MAP and an electrocardiogram measuring device for measuring an electrical event E of the electrical-mechanical interval.

15. The system for retrofitting existing non-invasive cardio monitoring devices according to claim 1 further comprising a display unit connected to said conversion unit for displaying the invasive cardiac analogues in three dimensional coordinate space that is defined by a first axis indicative of the P, a second axis indicative of the A and a third axis indicative of the C.

16. The system for retrofitting existing non-invasive cardio monitoring devices according to claim 15 wherein said display unit additionally displays a three dimensional object defining a safe zone indicative of a safe hemodynamic state.

17. The system for retrofitting existing non-invasive cardio monitoring devices according to claim 16 wherein said display unit displays the first axis, the second axis, the third axis and the safe zone respectively in a predetermined color.

18. The system for retrofitting existing non-invasive cardio monitoring devices according to claim 16 wherein said display unit additionally displays a vector cross product indicative an amount of physiologic stress.

19. The system for retrofitting existing non-invasive cardio monitoring devices according to claim 1 further comprising a determination unit connected to said conversion unit for determining a fitness level of the subject based upon the invasive cardiac analogues.

20. The system for retrofitting existing non-invasive cardio monitoring devices according to claim 1 further comprising a determination unit connected to said conversion unit for determining management of an anesthetic-related procedure of the subject based upon the invasive cardiac analogues.

21. The system for retrofitting existing non-invasive cardio monitoring devices according to claim 1 further comprising a determination unit connected to said conversion unit for determining an abnormal cardiac condition of the subject based upon the invasive cardiac analogues.

22. The system for retrofitting existing non-invasive cardio monitoring devices according to claim 1 further comprising a data communication unit connected to the existing non-invasive cardiac parameter measuring devices at one location for transferring the non-invasive cardiac parameters to said interface unit at another location before converting the non-invasive cardiac parameters into the invasive cardiac analogues.

23. The system retrofitting existing non-invasive cardio monitoring devices according to claim 22 wherein said data communication unit transfers the non-invasive cardiac parameters to said interface unit via the Internet.

24. The system for retrofitting existing non-invasive cardio monitoring devices according to claim 22 wherein said data communication unit transfers the non-invasive cardiac parameters to said interface unit via telecommunication.

25. The system for retrofitting existing non-invasive cardio monitoring devices according to claim 1 wherein the existing non-invasive cardio monitoring devices are all portable.

* * * * *